(12) United States Patent
Greenlee et al.

(10) Patent No.: US 6,894,063 B2
(45) Date of Patent: May 17, 2005

(54) SUBSTITUTED UREA NEUROPEPTIDE Y Y5 RECEPTOR ANTAGONISTS

(75) Inventors: William J. Greenlee, Teaneck, NJ (US); Ying Huang, East Brunswick, NJ (US); Joseph M. Kelly, Parlin, NJ (US); Stuart W. McCombie, Caldwell, NJ (US); Andrew W. Stamford, Chatham Township, NJ (US); Yusheng Wu, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/096,390

(22) Filed: Mar. 12, 2002

(65) Prior Publication Data

US 2003/0114517 A1 Jun. 19, 2003

Related U.S. Application Data

(63) Continuation-in-part of application No. 09/950,908, filed on Sep. 12, 2001, now abandoned.
(60) Provisional application No. 60/232,255, filed on Sep. 14, 2000.

(51) Int. Cl.[7] .................... A61K 31/445; A61K 31/435; A61K 31/41; C07D 421/00; C07C 281/00
(52) U.S. Cl. .................... 514/315; 514/277; 514/359; 514/210.01; 514/212.01; 546/195; 564/37; 540/1; 540/484; 548/400
(58) Field of Search .................... 514/315, 359, 514/277, 210.01, 212.01; 546/195; 540/1, 484; 548/400; 564/37

(56) References Cited

U.S. PATENT DOCUMENTS

| 4,405,644 A | 9/1983 | Kabbe et al. |
| 4,623,662 A | 11/1986 | De Vries |
| 6,355,635 B1 * | 3/2002 | Elliott et al. .............. 514/231.5 |

FOREIGN PATENT DOCUMENTS

| EP | 1 249 233 A1 | 10/2002 | | |
| WO | WO 97/19682 | 6/1997 | .......... | A61K/31/18 |
| WO | WO 98/35957 | 8/1998 | .......... | C07D/401/04 |
| WO | WO 99/64394 | 12/1999 | .......... | C07C/321/02 |

OTHER PUBLICATIONS

Stanley, et al. "Neuropeptide Y injected in the paraventricular hypothalamus: A powerful stimulant of feeding behavior" Proc. Natl. Acad. Sci. 82:3940–3943(1985).

Billington, et al. "Effects of intracerebroventricular injection of neuropeptide Y on energy metabolism" Am. J. Physiol. 260:R321–R327 (1991).

Wahlestedt, et al. "Neuropeptide Y–related peptides and their receptors—are the receptors potential therapeutic drug targets?" Annu. Rev. Pharmacol. Toxicol. 32:309–352(1993).

Gerald, et al., "A receptor subtype involved in neuropeptide–Y–induced food intake" Nature 382:168–171 (1996).

Gehlert, D., "Minireview—Multiple Receptors for the Pancreatic Polypeptide (PP–Fold) Family: Physiological Implications" Proc. Soc. Exp. Biol. Med. 218:7–22(1998).

Michel, et al., "XVI. International Union of Pharmacology Recommendations for the Nomenclature of Neuropeptide Y, Peptide YY, and Pancreatic Polypeptide Receptors" Pharmacol. Rev. 50(1):143–150(1998).

Hwa, et al., "Activation of the NPY Y5 receptor both feeding and energy expenditure" American J. Physiological 277:(46):R1428–R1434(1999).

McNally JJ et al.: "N–Acylated alpha –(3–pyridylmethyl)–beta–aminotetralin antagonists of the human neuropeptide Y Y 5 receptor" Bioorganic & Medicinal Chemistry Letters, vol. 10, No. 15, Aug. 7, 2000, pp. 1641,–1643, XP004213213 ISSN: 0960–894X.

* cited by examiner

Primary Examiner—Shengjun Wang
(74) Attorney, Agent, or Firm—William Y. Lee

(57) ABSTRACT

A novel class of compounds such as antagonists of the neuropeptide Y Y5 receptor, methods of making such compounds, pharmaceutical compositions containing one or more such compounds, methods of preparing pharmaceutical formulations comprising one or more such compounds, and methods of treatment, prevention or amelioration of one or more diseases associated with the neuropeptide Y Y5 receptor are disclosed.

17 Claims, No Drawings

SUBSTITUTED UREA NEUROPEPTIDE Y Y5 RECEPTOR ANTAGONISTS

CROSS REFERENCE TO RELATED APPLICATIONS

This application is a Continuation-in-part of U.S. Ser. No. 09/950,908 filed on Sep. 12, 2001, now abandoned which claims the benefit of U.S. Provisional Application No. 60/232,255 filed on Sep. 14, 2000.

FIELD OF THE INVENTION

The present invention relates to neuropeptide Y Y5 receptor antagonists useful in the treatment of metabolic and eating disorders, pharmaceutical compositions containing the compounds, and methods of treatment using the compounds.

BACKGROUND OF THE INVENTION

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev., 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y5 receptor subtype. The isolation and characterization of the NPY Y5 receptor subtype has been reported (Gerald, C. et al., Nature, 1996, 382, 168; Gerald, C. et al. WO 96/16542). Additionally, it has been reported that activation of the NPY Y5 receptor by administration of the Y5—selective agonist [D-Trp$^{32}$]NPY to rats stimulates feeding and decreases energy expenditure (Gerald, C. et al., Nature, 1996, 382, 168; Hwa, J. et al., Am. J. Physiol., 277 (46), R1428, 1999).

Published PCT patent application WO 00/27845 describes a class of compounds, characterized therein as spiro-indolines, said to be selective neuropeptide Y Y5 receptor antagonists and useful for the treatment of obesity and the complications associated therewith. Known urea derivatives indicated as possessing therapeutic activity are described in U.S. Pat. No. 4,623,662 (antiatherosclerotic agents) and U.S. Pat. No. 4,405,644 (treatment of lipometabolism). Provisional application, U.S. Ser. No. 60/232,255 describes a class of substituted urea neuropeptide Y Y5 receptor antagonists.

SUMMARY OF THE INVENTION

The present invention relates to compounds represented by the structural formula I:

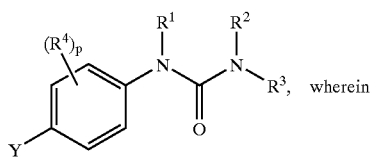

wherein

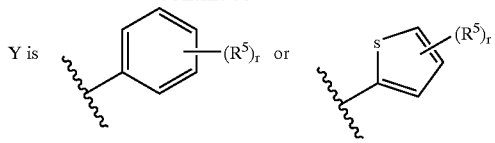

$R^1$ is hydrogen or $(C_1-C_6)$alkyl;
$R^2$ is hydrogen, $(C_1-C_6)$alkyl, $(C_3-C_9)$cycloalkyl or $(C_3-C_7)$cycloalkyl$(C_1-C_6)$alkyl;

$R^3$ is

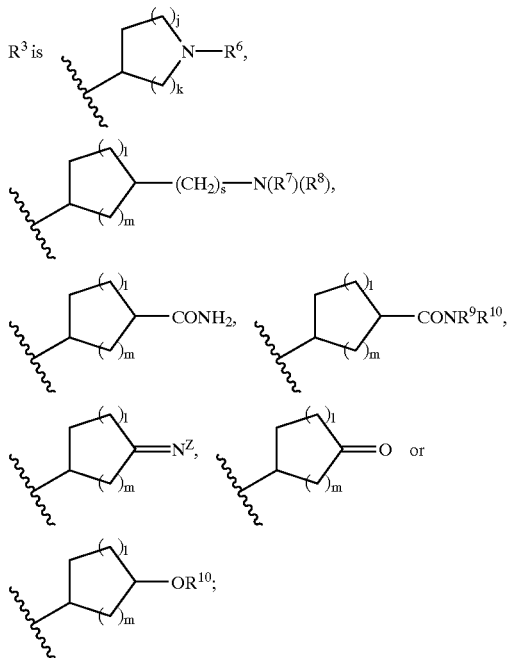

where
Z is $OR^{10}$ or $—N(R^9)(R^{10})$;
j is 0, 1 or 2;
k is 1 or 2;
l is 0, 1 or 2;
m is 0, 1 or 2;
p is 1, 2 or 3;
r is 1, 2 or 3;
and s is 0, 1, 2, 3, 4, 5 or 6;

$R^4$ is a subsituent independently selected from hydrogen, —OH, halogen, haloalkyl, $(C_1-C_6)$alkyl, $(C_3-C_7)$cycloalkyl, $(C_3-C_7)$cycloalkyl$(C_1-C_6)$alkyl, —CN, $(C_1-C_6)$alkylO—, $(C_3-C_7)$cycloalkylO—, $(C_1-C_6)$alkyl$(C_3-C_7)$cycloalkylO—, $(C_1-C_6)$alkylS—, $(C_3-C_7)$cycloalkylS—, $(C_1-C_6)$alkyl$(C_3-C_7)$cycloalkylS—, $—NR^9R^{10}$, $—NO_2$, $—CONR^9R^{10}$ and $—NR^2COR^{10}$;

$R^5$ is a substituent independently selected from hydrogen, halogen, —OH, haloalkyl, haloalkoxy, —CN, $—NO_2$, $(C_1-C_6)$alkyl, $(C_3-C_7)$cycloalkyl, $(C_3-C_7)$cycloalkyl$(C_1-C_6)$alkyl, $(C_1-C_6)$alkylO—, $(C_3-C_7)$cycloalkylO—, $(C_1-C_6)$alkyl$(C_3-C_7)$cycloalkylO—, $—CONH_2$ and $—CONR^9R^{10}$;

$R^6$ is $(C_1-C_6)$alkylSO$_2$—, $(C_3-C_7)$cycloalkylSO$_2$—, $(C_1-C_6)$alkyl$(C_3-C_7)$cycloalkylSO$_2$—, $(C_1-C_6)$haloalkylSO$_2$—, hydroxy$(C_2-C_6)$alkyl)SO$_2$—, (amino$(C_2-C_6)$alkyl)SO$_2$—, alkoxy$(C_2-C_6)$alkyl)SO$_2$—, alkylamino$(C_2-C_6)$alkyl)SO$_2$—, dialkylamino$(C_2-C_6)$ alkyl)SO$_2$—, arylSO$_2$—, heteroarylSO$_2$—, aryl(C$_2$-C$_6$-alkylSO$_2$—, R$^9$R$^{10}$NSO$_2$—, (C$_1$-C$_6$)alkylC(O)—, (C$_3$-C$_7$) cycloalkylC(O)—, (C$_3$-C$_7$)cycloalkyl(C$_1$-C$_6$)alkylC(O)—, arylC(O)—, heteroarylC(O)—, R$^9$R$^{10}$NC(O)—, —(S) CNR$^9$R$^{10}$, aryl, heteroaryl, —(CH$_2$)$_n$C(O)NR$^9$R$^{10}$, alkylS (NCN=)C—, R$^9$R$^{10}$N(NCN=)C—, (C$_1$-C$_6$)alkyl, (C$_3$-C$_7$)cycloalkyl, (C$_3$-C$_7$)cycloalkyl(C$_1$-C$_6$)alkyl, aryl (C$_1$-C$_6$)alkyl, heteroaryl(C$_1$-C$_6$)alkyl, or R$^9$OC(O)—;

R$^7$=hydrogen or alkyl;

R$^8$ is hydrogen, (C$_1$-C$_6$)alkyl, (C$_3$-C$_7$)cycloalkyl, (C$_3$-C$_7$)cycloalkyl(C$_1$-C$_6$)alkyl, aryl, heteroaryl, (C$_1$-C$_6$) alkylSO$_2$—, (C$_3$-C$_7$)cycloalkylSO$_2$—, (C$_1$-C$_6$)alkyl (C$_3$-C$_7$)cycloalkylSO$_2$—, (C$_1$-C$_6$)haloalkylSO$_2$— or arylSO$_2$—;

R$^9$ is hydrogen, (C$_1$-C$_6$)alkyl, (C$_3$-C$_7$)cycloalkyl, (C$_3$-C$_7$)cycloalkyl(C$_1$-C$_6$)alkyl, aryl(C$_1$-C$_6$)alkyl, aryl, acyl or heteroaryl; and, R$^{10}$ is hydrogen, (C$_1$-C$_6$)alkyl, (C$_3$-C$_7$)cycloalkyl, (C$_3$-C$_7$)cycloalkyl(C$_1$-C$_6$)alkyl, aryl(C$_1$-C$_6$)alkyl, aryl or heteroaryl;

or R$^9$ and R$^{10}$ taken together with the nitrogen atom form a 4–7 membered ring containing 1 or 2 heteroatoms selected from N, O or S with proviso that two O or S atoms are not adjacent to one another;

n=1 to 6;

or a pharmaceutically acceptable salt and/or hydrate thereof.

The present invention also relates to a method of treating metabolic and eating disorders, such as obesity and hyperphagia, and diabetes comprising administering to a mammal in need of such treatment an effective amount of a compound of formula I.

Another aspect of the invention is a pharmaceutical composition which comprises a compound of formula I in combination with a pharmaceutically acceptable carrier.

DETAILED DESCRIPTION

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

As used above, and throughout the specification, the following terms, unless otherwise indicated, shall be understood to have the following meanings:

"Patient" includes both human and other mammals.

"Mammal" means humans and other animals.

"Alkyl" means an aliphatic hydrocarbon group, which may be straight or branched and comprising 1 to 20 carbon atoms in the chain. Preferred alkyl groups contain 1 to 12 carbon atoms in the chain. More preferred alkyl groups contain 1 to 6 carbon atoms in the chain. Branched means that one or more lower alkyl groups such as methyl, ethyl or propyl, are attached to a linear alkyl chain.

"Lower alkyl" means a group having 1 to 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and alkylOC(O)—. Non-limiting examples of suitable alkyl groups include methyl, ethyl, n-propyl, isopropyl, n-butyl, and t-butyl.

"Alkenyl" means an aliphatic hydrocarbon group containing at least one carbon—carbon double bond and which may be straight or branched and comprising 2 to 15 carbon atoms in the chain. Preferred alkenyl groups have 2 to 12 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group containing at least one carbon—carbon triple bond and which may be straight or branched and comprising 2 to 15 carbon atoms in the chain. Preferred alkynyl groups have 2 to 12 carbon atoms in the chain; and more preferably 2 to 4 carbon atoms in the chain. Branched means that one or more lower alkyl groups such as methyl, ethyl or propyl, are attached to a linear alkynyl chain. "Lower alkynyl" means 2 to 6 carbon atoms in the chain, which may be straight or branched. Non-limiting examples of suitable alkynyl groups include ethynyl, propynyl, and 2-butynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising 6 to 14 carbon atoms, preferably 6 to 10 carbon atoms. The aryl group can be unsubstituted or optionally substituted on the ring with one or more substituents which may be the same or different, each being independently selected from the group consisting of alkyl, aryl, OCF$_3$, alkylOC(O)—, arylOC(O)—, CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ may be the same or different each being independently selected from the group consisting of hydrogen, alkyl, aryl, and aralkyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different, each being independently selected from the group consisting of hydrogen, alkyl, aryl, and aralkyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthlenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising 3 to 10 carbon atoms, preferably 5 to 10 carbon atoms. Preferred cycloalkyl rings contain 5 to 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above. The preferred halogen is fluoride. Specific examples, but non-limiting examples include a halo($C_1$–$C_6$)alkyl, —$CF_2CH_3$, —$CH_2F_3$ and $CF_3$.

"Cycloalkenyl" means a non-aromatic mono or multicyclic ring system comprising 3 to 10 carbon atoms, preferably 5 to 10 carbon atoms which contains at least one carbon—carbon double bond. Preferred cycloalkenyl rings contain 5 to 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising 3 to 10 ring atoms, preferably 5 to 10 ring atoms, in which one or more of the atoms in the ring system is an element other than carbon, for example nitrogen, oxygen or sulfur atom, alone or in combination, and which contains at least one carbon—carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2-dihydropyridyl, 1,4-dihydropyridyl, 1,2,3,6-tetrahydropyridyl and the like. Non-limiting examples of suitable oxaheterocyclenyl groups include 3,4-dihydro-2H-pyran, dihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl and the like.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of 5 to 6 ring atoms. The arylcycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of 5 to 6 ring atoms and the cycloalkyl consists of 5 to 6 ring atoms. The prefix aza, oxa or thia before heteroaryl means that at least a nitrogen, oxygen or sulfur atom is present respectively as a ring atom. The heteroarylcycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 4,5,6,7-tetrahydro-1H-benzimidazolyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl. "Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ group in which one or more of the hydrogen atoms on the nitrogen is replaced by an alkyl group as defined above.

"Arylamino" means an —$NH_2$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —$CH_3C(O)$—, $CH_3CH_2C(O)$— and the like.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$SO_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$SO_2$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by MCH, and thus producing the desired therapeutic effect.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by separating isomers of a compound of formula I or by synthesizing individual isomers of a compound of formula I.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

In a preferred group of compounds of formula 1, Y is

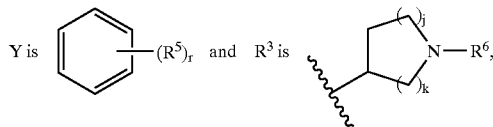

-continued

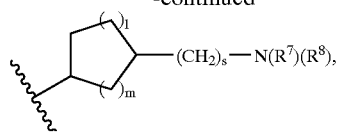

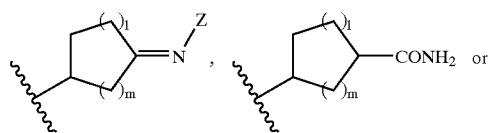

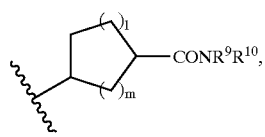

including, in particular, those compounds in which $R^5$ is a substitutent independently selected from hydrogen, halogen, haloalkyl and haloalkoxy and the sum of j and k is 1, 2 or 3.

In another preferred group of compounds of formula 1, Y is

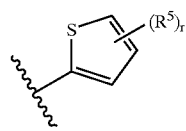 and $R^3$ is 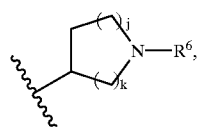, including, in particular, those compounds in which $R^5$ and $R^6$ each independently is 1 to 3 substituents independently selected from the group consisting of hydrogen, halogen, haloalkyl and haloalkoxy, preferably halo($C_1$–$C_6$)alkyl or halo($C_1$–$C_6$)alkoxy, more preferably $CH_3CF_2$—, $CF_3$ and $CF_3O$—, and the sum of j and k is 1, 2 or 3.

In another embodiment, Y is

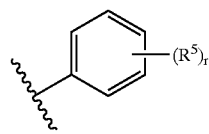

and $R^5$ is Cl, F, $CF_3$, $CF_3O$— and r is 1 or 2.

In another embodiment Y is

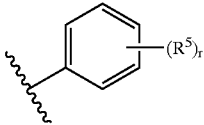

and $R^5$ is $CF_3$ and r is 1.

In another embodiment Y is

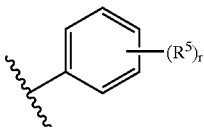

and $R^5$ is F and r is 1 or 2.

In another embodiment $R^3$ is

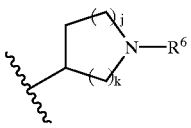

the sum of j and k is 1, 2 or 3 and $R^6$ is ($C_3$–$C_4$)cycloalkyl or heteroaryl.

The symbols

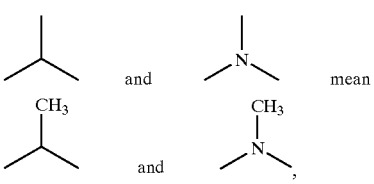

respectively.

Compounds of formula I may be produced by processes known to those skilled in the art as shown in the following reaction schemes and in the preparations and examples below.

Scheme 1

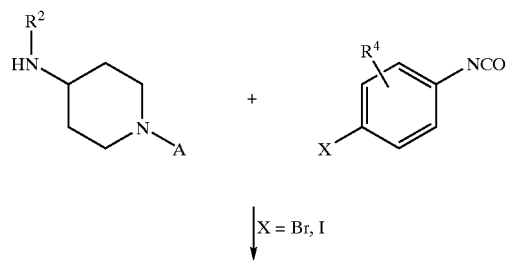

$X = Br, I$

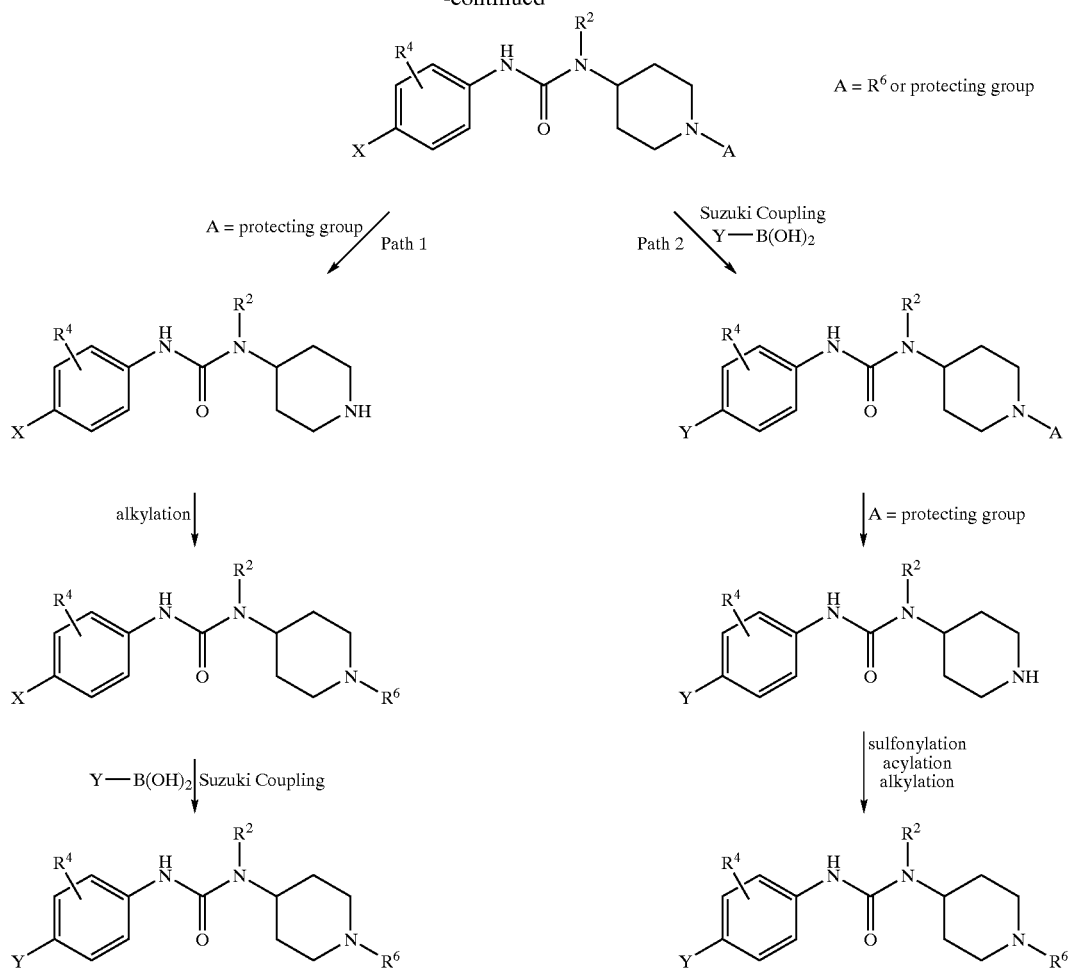

In Scheme 1, a 4-halophenyl isocyanate is condensed with an amino substituted cyclic amine derivative to give a 4-halophenyl urea derivative. Cleavage of the cyclic amine protecting group by methods known to those skilled in the art affords a cyclic amine derivative that can be derivatized, for example by alkylation (Path 1). Coupling of the product with, for example, an arylboronic acid, under palladium catalysis (Suzuki coupling) yields a biaryl urea derivative. Alternatively, the condensation product can be arylated, for example, by use of a Suzuki coupling reaction (Path 2). When A is a protecting group, deprotection affords an amine that can be derivatized by, for example, sulfonylation, acylation or alkylation.

Scheme 2

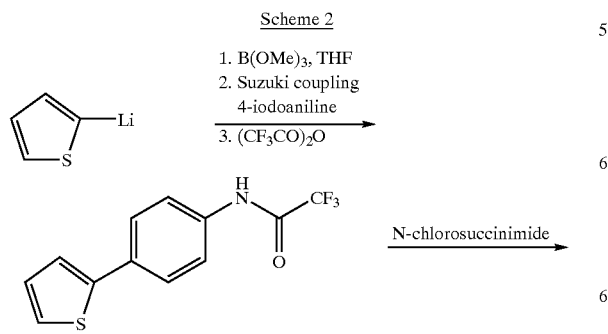

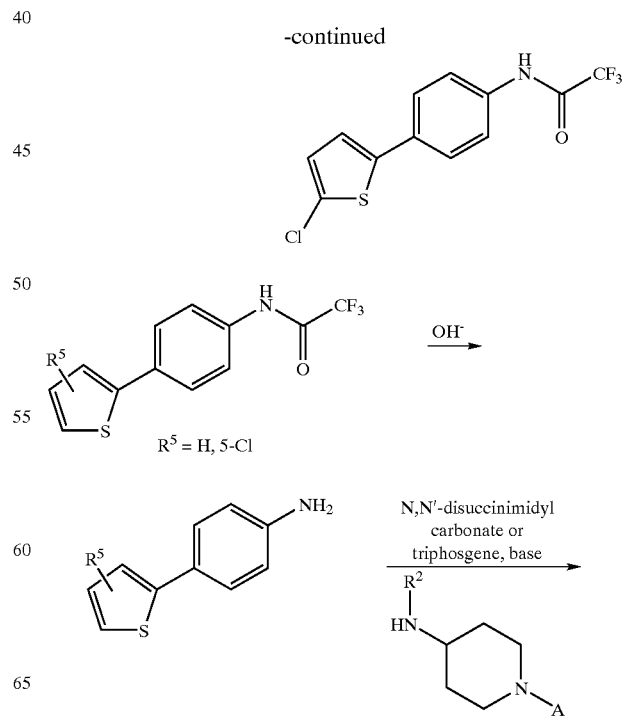

15
-continued

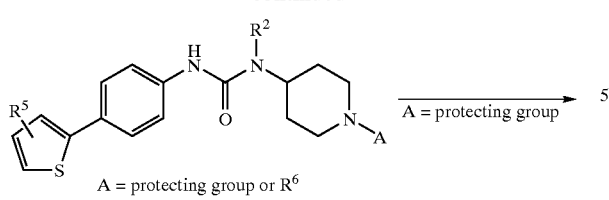

A = protecting group or R⁶

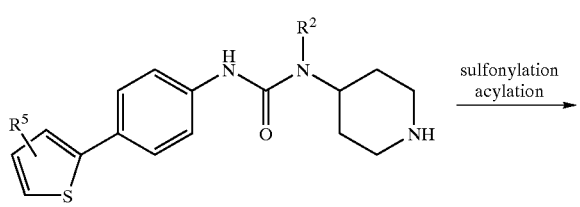

16
-continued

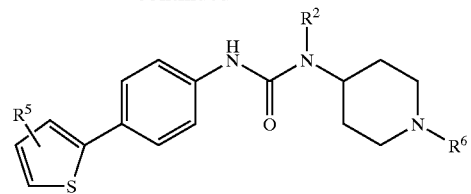

In Scheme 2, reaction of an aryl lithium, for example, 5-thienyl lithium, with trimethylborate and coupling of the resultant boronate with a 4-haloaniline under palladium catalysis yields a biaryl amine derivative. Protection of the amine with, for example, trifluoroacetic anhydride gives a trifluoroacetamide derivative that can be halogenated with an appropriate halogenating agent, for example N-chlorosuccinimide. The protecting group can be cleaved and the resultant amine can be reacted with, for example, N,N'-disuccinimidyl carbonate and an amino substituted cyclic amine derivative, for example an amino piperidine derivative, to give a substituted urea. Cleavage of the piperidine nitrogen protecting group gives an amine that can derivatized, for example, by sulfonylation or acylation.

Scheme 3

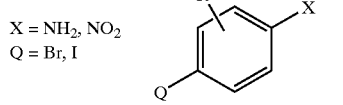

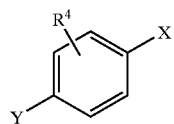

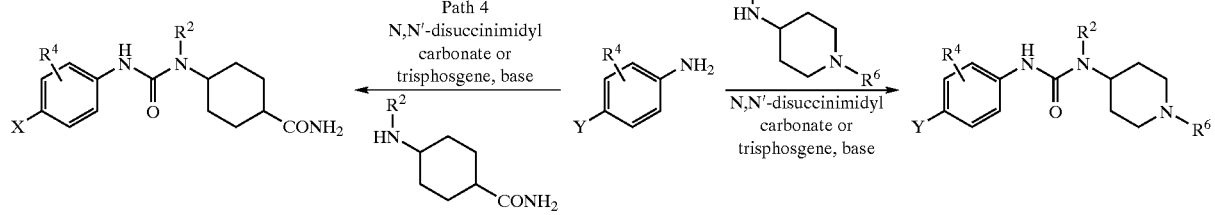

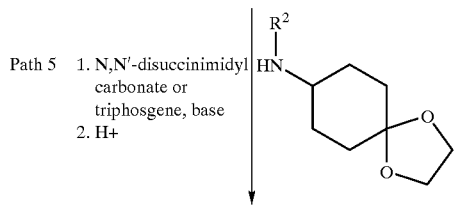

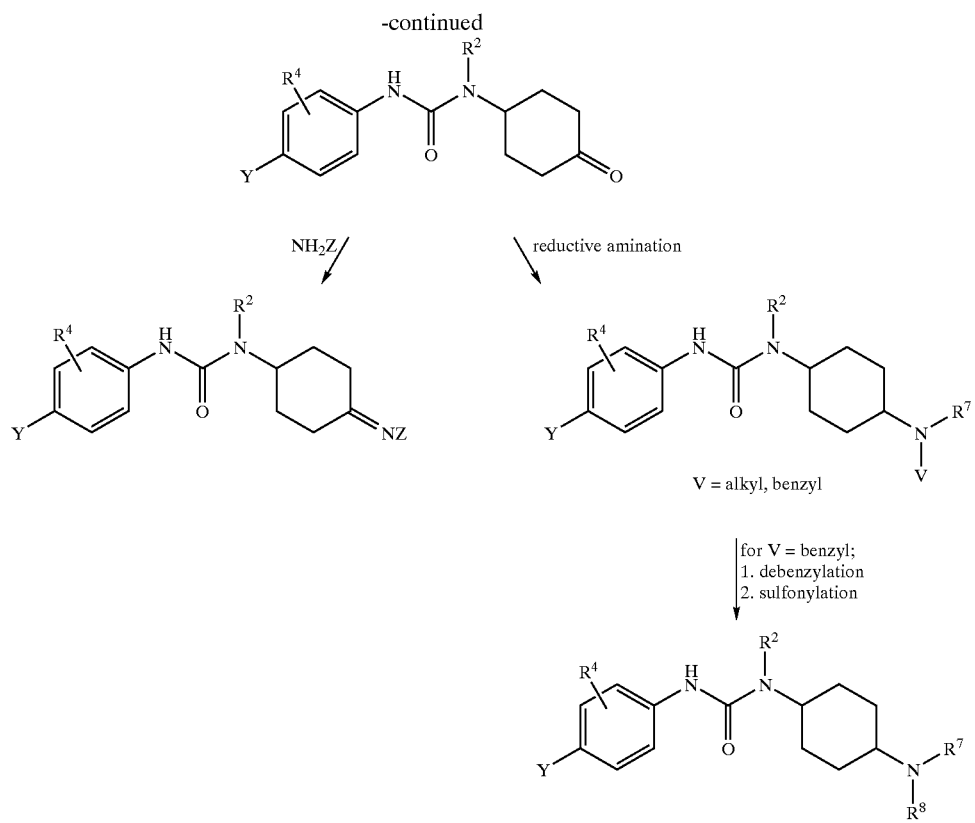

In Scheme 3, a 4-haloaniline or 4-halonitrobenzene derivative is arylated by use of, for example, a Suzuki coupling reaction. When X is a nitro group, the nitro group is subsequently reduced to an amine. The biaryl amine derivative can be converted to an isocyanate derivative, which can be condensed with an amino substituted cyclic amine derivative (Path 3). Alternatively, condensation with an amino substituted cycloalkyl derivative affords cycloalkyl urea derivatives (Paths 4 and 5). An appropriately functionalized cycloalkyl urea derivative can be further functionalized as shown, for example, in Path 5.

The compounds of formula I exhibit selective neuropeptide Y Y5 receptor antagonizing activity, which has been correlated with pharmaceutical activity for treating metabolic and eating disorders, such as obesity, hyperphagia, and diabetes.

Another aspect of this invention is a method of treating a mammal (e.g., human) having a disease or condition mediated by the neuropeptide Y Y5 receptor by administering a therapeutically effective amount of a compound of Formula I or a pharmaceutically acceptable salt of said compound to the mammal.

Another aspect of this invention is directed to a method of treating obesity comprising administering to a mammal in need of such treatment a therapeutically effective amount of a compound of Formula I or a pharmaceutically acceptable salt of said compound.

Another aspect of this invention is directed to a method for treating metabolic and eating disorders such as bulimia and anorexia comprising administering to a mammal a therapeutically effective amount of a compound of Formula I or a pharmaceutically acceptable salt of said compound.

Another aspect of this invention is directed to a method for treating hyperlipidemia comprising administering to a mammal a therapeutically effective amount of a compound of Formula I or a pharmaceutically acceptable salt of said compound.

Another aspect of this invention is directed to a method for treating cellulite and fat accumulation comprising administering to a mammal a therapeutically effective amount of a compound of Formula I or a pharmaceutically acceptable salt of said compound.

Another aspect of this invention is directed to a method for treating Type II diabetes comprising administering to a mammal a therapeutically effective amount of a compound of Formula I or a pharmaceutically acceptable salt of said compound.

In addition to the "direct" effect of the compounds of this invention on the neuropeptide Y Y5 receptor subtype, there are diseases and conditions that will benefit from the weight loss such as insulin resistance, impaired glucose tolerance, Type II Diabetes, hypertension, hyperlipidemia, cardiovascular disease, gall stones, certain cancers and sleep apnea.

This invention is also directed to pharmaceutical compositions, which comprise an amount of a compound of Formula I or a pharmaceutically acceptable salt of said compound and a pharmaceutically acceptable carrier therefor.

This invention is also directed to pharmaceutical compositions for the treatment of obesity which comprise an obesity treating amount of a compound of Formula, I or a pharmaceutically acceptable salt of said compound and a pharmaceutically acceptable carrier therefor.

Compounds of Formula I can be produced by processes known to those skilled in the art using either solution phase or solid phase synthesis as shown in the following reaction schemes, in the preparations and examples below.

The compounds of formula I display pharmacological activity in test procedures designed to demonstrate neuropeptide Y Y5 receptor antagonist activity. The compounds are non-toxic at pharmaceutically therapeutic doses. Following are descriptions of the test procedures.

cAMP Assay

HEK-293 cells expressing the Y5 receptor subtype were maintained in Dulbecco's modified Eagles' media (Gico-BRL) supplemented with 10% FCS (ICN), 1% penicillin-streptomycin and 200 µg/ml Geneticin® (GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 µl/well of assay buffer (HBSS supplemented with 4 mM $MgCl_2$, 10 mM HEPES, 0.2% BSA[HH]) containing 1 mM 3-isobutyl-1-methylxanthine ([IBMX] Sigma #I-587) with or without the antagonist compound of interest at 37° C. After 20 minutes the 1 mM IBMX-HH assay buffer (±antagonist compound) was removed and replaced with assay buffer containing 1.5 µM (CHO cells) or 5 µM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 µl ethanol. The tissue culture plates were agitated on a platform shaker for 15 minutes, after which the plates were transferred to a warm bath in order to evaporate the ethanol. Upon bringing all wells to dryness, the cell residues were resolubilized with 250 µl FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$$K_B = [B]/(1 - \{[A']/[A]\})$$

where

[A] is the $EC_{50}$ of the agonist (NPY) in the absence of antagonist,

[A'] is the $EC_{50}$ of the agonist (NPY) in the presence of antagonist, and [B] is the concentration of the antagonist.

NPY Receptor Binding Assay

Human NPY Y5 receptors were expressed in CHO cells. Binding assays were performed in 50 mM HEPES, pH 7.2, 2.5 mM $CaCl_2$, 1 mM $MgCl_2$ and 0.1% BSA containing 5–10 µg of membrane protein and 0.1 nM $^{125}$L-peptide YY in a total volume of 200 µl. Non-specific binding was determined in the presence of 1 µM NPY. The reaction mixtures were incubated for 90 minutes at room temperature then filtered through Millipore MAFC glass fiber filter plates which had been pre-soaked in 0.5% polyethleneimine. The filters were washed with phosphate-buffered saline, and radioactivity was measured in a Packard TopCount scintillation counter.

For the compounds of this invention, a range of neuropeptide Y5 receptor binding activity from about 0.2 nM to about 500 nM was observed. Compounds of this invention preferably have a binding activity in the range of about 0.2 nM to 250 nM, more preferably about 0.2 to 100 nM, and most preferably about 0.2 to 10 nM.

Yet another aspect of this invention are combinations of a compound of Formula I or a pharmaceutically acceptable salt of said compound and other compounds as described below.

Accordingly, another aspect of this invention is a method for treating obesity comprising administering to a mammal (e.g., a female or male human)

a. an amount of a first compound, said first compound being a Formula I compound or a pharmaceutically acceptable salt of said compound; and b. an amount of a second compound, said second compound being an anti-obesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a Formula I compound or a pharmaceutically acceptable salt of said compound a second compound, said second compound being an anti-obesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a Formula I compound or a pharmaceutically acceptable salt of said compound and a pharmaceutically acceptable carrier, vehicle or diluent in a first unit dosage form;

b. an amount of an anti-obesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a mammal (e.g., a female or male human)

a. an amount of a first compound, said first compound being a Formula I compound or a pharmaceutically acceptable salt of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a Formula I compound or a pharmaceutically acceptable salt of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a Formula I compound or a pharmaceutically acceptable salt of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The invention disclosed herein is exemplified by the following preparations and examples which should not be construed to limit the scope of the disclosure. Alternative mechanistic pathways and analogous structures may be apparent to those skilled in the art.

In the preparations and examples, the following abbreviations are used: room temperature (R.T.), phenyl(Ph), -t-butyloxycarbonyl(-Boc), methylamine (MeNH$_2$), sodium triacetoxyborohydride (NaBH(O Ac)$_3$)), ethyl acetate (EtOA$_c$), methanol (MeOH), triethylamine (Et$_3$ N), ether (Et$_2$O), tetrahydrofuran (THF), diisopropylethylamine (iPr$_2$NEt), 1,2-dimethoxyethane (DME), ethanol (EtOH) and preparative thin layer chromatography (PTLC).

Preparation 1

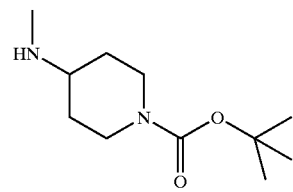

To a mixture of N-t-butoxycarbonyl4-piperidone (10.0 g, 50 mmol) and aqueous methylamine (40% w/w, 10 ml) in 1,2-dichloroethane (125 ml) was added NaBH(OAc)$_3$ (16.0 g, 75 mmol). The reaction mixture was stirred overnight, then 1 M NaOH (250 ml) was added and the whole was extracted with ether (700 ml). The organic layer was washed with sat'd NaCl, dried (MgSO$_4$), filtered, and concentrated to give the product (10.5 g, 97%) as an oil. $^1$H NMR (CDCl$_3$, 400 MHz) δ 4.09 (2H, m), 2.86 (2H, m), 2.55 (1H, m), 2.50 (3H, s), 1.90 (2H, m), 1.51 (9H, s), 1.30 (2H, m).

Preparation 2

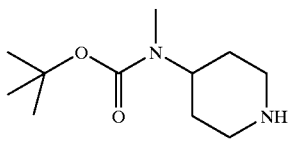

Step 1

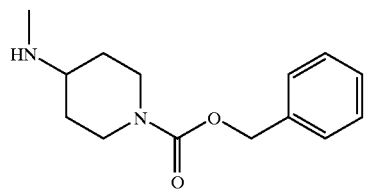

To a mixture of N-benzyloxycarbonyl-4-piperidone (10.70 g, 43.1 mmol) and aq. 40% MeNH$_2$ (6.67 g, 85.8 mmol) in CH$_2$Cl$_2$ (200 ml) at R.T. was added NaBH(OAc)$_3$ (27.25 g, 128.6 mmol). The reaction mixture was stirred at R.T. for 3 h then poured into sat'd NaHCO$_3$ and extracted with CH$_2$Cl$_2$ (3×200 ml). The combined organic layers were dried (Na$_2$SO$_4$), filtered and concentrated to give the product (10.63 g, 100%) that was used without further purification. $^1$H NMR (CDCl$_3$, 400 MHz) δ 7.34 (5H, m), 5.12 (2H, s), 4.19 (2H, b), 2.87 (2H, b), 2.72 (1H, m), 2.49 (3H, s), 1.92 (2H, b), 1.42 (2H, m). MS m/e 249 (M+H).

Step 2

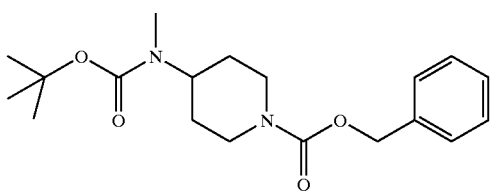

To the product of Step 1 (10.63 g, 42.9 mmol) in anhydrous CH$_2$Cl$_2$ (200 ml) at R.T. was added di-tert-butyl dicarbonate (11.30 g, 51.8 mmol) in portions. The reaction mixture was allowed to stir at R.T. for 5 h then poured into 1 N NaOH (50 ml)/CH$_3$OH (10 ml). The mixture was stirred for 15 min. and extracted with CH$_2$Cl$_2$ (3×200 ml). The combined organic layers were dried (Na$_2$SO$_4$), filtered, and concentrated. The residue was subjected to column chromatography (gradient 1:10 to 1:4 EtOAc/hexane) to give the product (13.00 g, 87%). $^1$H NMR (CDCl$_3$, 400 MHz) δ 7.33 (5H, m), 5.10 (2H, s), 4.19 (3H, m), 2.87 (2H, b), 2.68 (3H, s), 1.60 (4H, m), 1.44 (9H, s). MS m/e 349 (M+H).

Step 3

A mixture of the product of Step 2 (12.90 g, 37.0 mmol) and 10% Pd/C (1.29 g) in MeOH (300 ml) was stirred under an H$_2$ atmosphere. After 16 h the reaction mixture was filtered through celite and the filter pad was washed with MeOH. The combined filtrate and washings were concentrated to afford the product (7.80 g, 98.3%). $^1$H NMR (CDCl$_3$, 400 MHz) δ 4.19 (1H, b), 3.15 (2H, b), 2.74 (3H, s), 2.66 (2H, m), 1.63 (4H, m), 1.46 (9H, s). MS m/e 215 (M+H).

Preparation 3

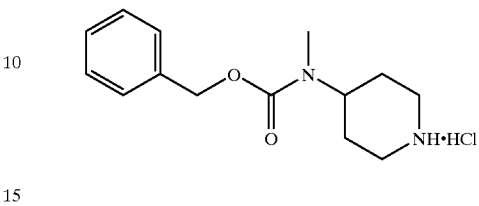

To a stirred solution of Preparation 1 (21.0 g, 83.7 mmol) and Et$_3$N (35 ml, 252 mmol) in CH$_2$Cl$_2$ (300 ml) was added benzyl chloroformate (18 ml, 126 mmol) dropwise. After 5 h, sat'd NH$_4$Cl (200 ml) was added, and the organic layer was washed with H$_2$O (150 ml) and sat'd NaCl (150 ml), dried (MgSO$_4$), filtered and concentrated. To the residue (32 g) was added 4N HCl in 1,4-dioxane (300 ml), and the mixture was stirred for 4 h. The reaction mixture was concentrated, acetone was added, and the reaction mixture was again concentrated. The solid residue was dissolved in MeOH (40 ml) and Et$_2$O was added. The resultant precipitate was collected, washed with Et$_2$O, and dried to give the product as a white solid (20.2 g, 85%). MS m/e 249 (M+H, free base).

EXAMPLE 1

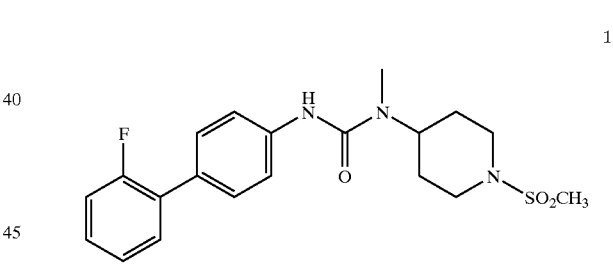

1

Step 1

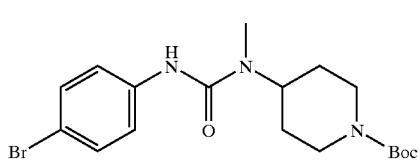

1-1-1

To a solution of Preparation 1 (7.0 g, 33 mmol) in CH$_2$Cl$_2$ (200 ml) was added 4-bromophenyl isocyanate (6.8 g, 35 mmol). The reaction mixture was stirred for 16 h, then H$_2$O (200 ml) was added, and the organic layer was dried (MgSO$_4$), filtered and evaporated. The residue was triturated with hexanes to give a white solid (11.0 g, 81%). MS (FAB) m/e 411 (M+H)$^+$.

Step 2

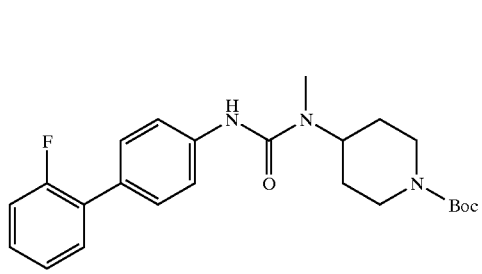
1-2-1

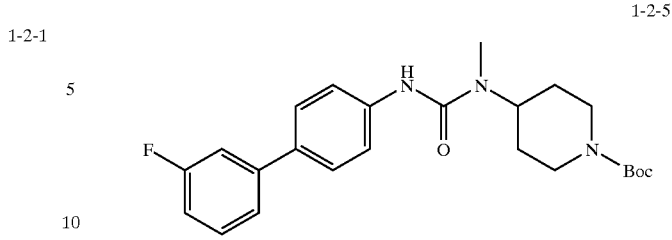
1-2-5

To a solution of the product of Step 1 (400 mg, 0.97 mmol) and Pd(dppf)Cl$_2$·CH$_2$Cl$_2$ (200 mg, 0.24 mmol) in toluene (10 ml) was added 2-fluorophenylboronic acid (250 mg, 1.43 mmol), Cs$_2$CO$_3$ (350 mg, 1.1 mmol), and H$_2$O (0.3 ml). The reaction mixture was heated in a 90° C. oil bath under N$_2$ for 1 h, then allowed to cool. The reaction mixture was partitioned between EtOAc (100 ml) and H$_2$O (50 ml). The organic layer was dried (MgSO$_4$), filtered and evaporated. Flash chromatography (3:7 acetone/hexane) of the residue afforded the product (400 mg, 97%). HRMS calc. for C$_{24}$H$_{31}$FN$_3$O$_3$ (M+H) 428.2349. Found 428.2343.

Coupling of the product of Step 1 with the appropriate boronic acid by essentially the same procedure gave:

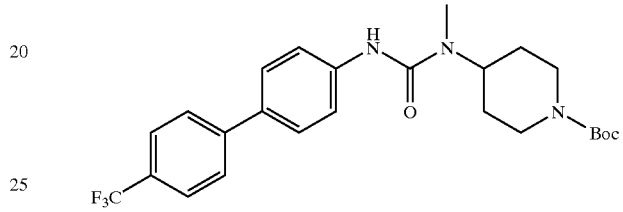
1-2-2

HRMS calc. for C$_{25}$H$_{31}$F$_3$N$_3$O$_3$ (M+H) 478.2318. Found 478.2313.

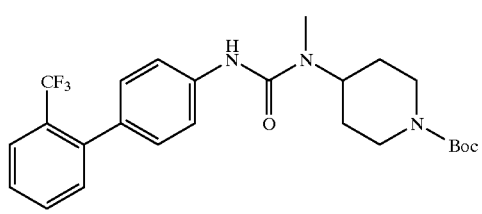
1-2-3

HRMS calc. for C$_{25}$H$_{31}$F$_3$N$_3$O$_3$ (M+H) 478.2318. Found 478.2313.

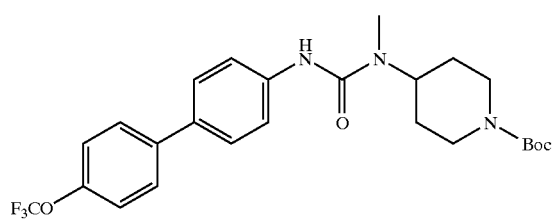
1-2-4

HRMS calc. for C$_{25}$H$_{31}$F$_3$N$_3$O$_4$ (M+H) 494.2260. Found 494.2267.

HRMS calc. for C$_{24}$H$_{31}$FN$_3$O$_3$ (M+H) 428.2343. Found 428.2349.

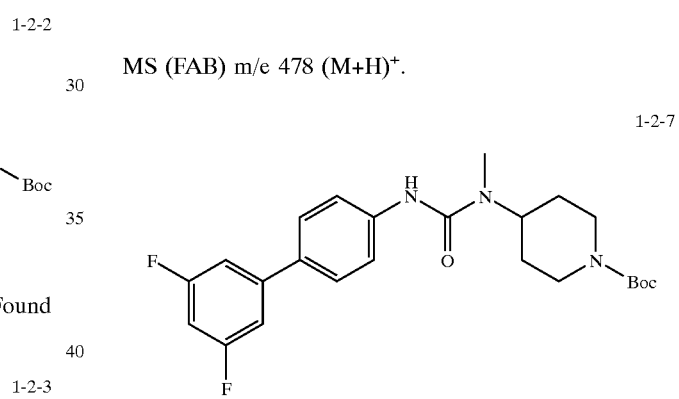
1-2-6

MS (FAB) m/e 478 (M+H)$^+$.

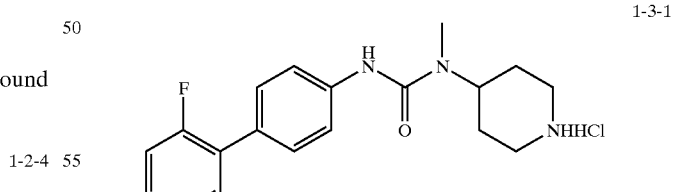
1-2-7

MS (FAB) m/e 446 (M+H)$^+$.

Step 3

1-3-1

To a solution of the product of Step 2 (100 mg, 0.23 mmol) in CH$_2$Cl$_2$ (5 ml) was added 4 M HCl in 1,4-dioxane (3 ml). After 16 h, the reaction mixture was concentrated. The residue was triturated with ether and the solid was collected, washed with ether, and air-dried to give the product (80 mg, 96%). HRMS calc. for C$_{19}$H$_{23}$FN$_3$O (M+H) 328.1825. Found 328.1823.

Treatment of the other products from Step 2 by essentially the same procedure gave:

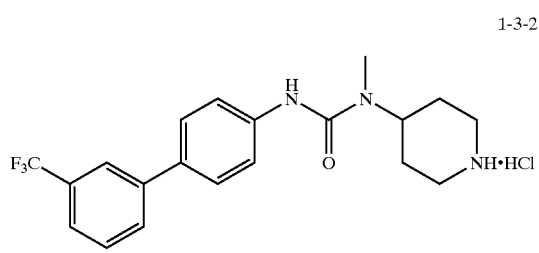

1-3-2

MS (ES) m/e 378 (M+H)$^+$.

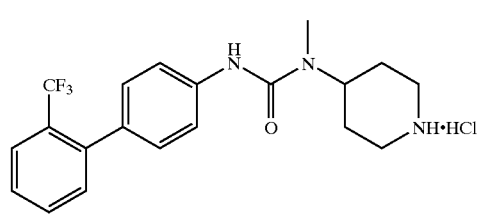

1-3-3

MS (FAB) m/e 378 (M+H)$^+$.

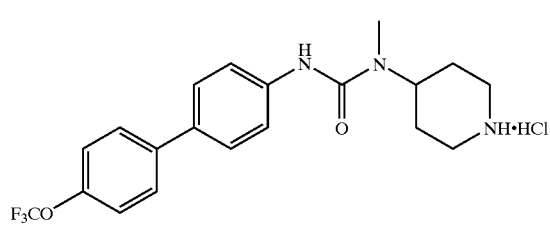

1-3-4

HRMS calc. for $C_{20}H_{23}F_3N_3O_2$ (M+H) 394.1742. Found 394.1747.

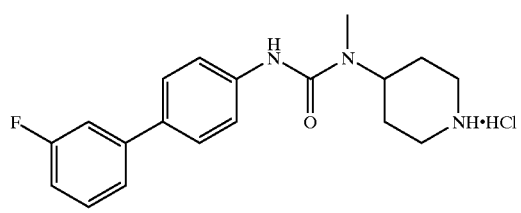

1-3-5

HRMS calc. for $C_{19}H_{23}FN_3O$ (M+H) 328.1825. Found 328.1823.

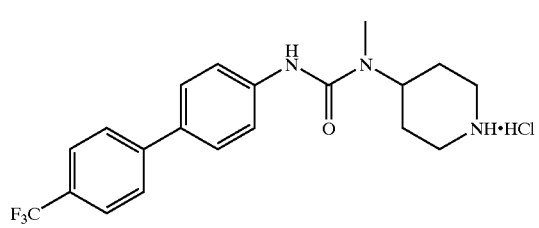

1-3-6

MS (ES) m/e 378 (M+H)$^+$.

1-3-7

HRMS calc. for $C_{19}H_{22}F_2N_3O$ (M+H) 346.1731. Found 346.1725.

Step 4

To a stirred solution of the product of Step 3 (20 mg, 0.055 mmol) and triethylamine (0.1 ml, 0.7 mmol) in CH$_2$Cl$_2$ (10 ml) was added methanesulfonyl chloride (0.1 ml, 0.1 mmol). After 16 h the reaction mixture was concentrated and the residue was subjected to PTLC (1:2 acetone/hexanes) to give a white solid (15 mg, 67%). HRMS calc. for $C_{20}H_{25}FN_3O_3S$ (M+H) 406.1601. Found 406.1599.

The following examples were prepared from the appropriate starting amine and sulfonyl chloride.

| Y | R$^6$ | MS (M + H) | Example |
|---|---|---|---|
| 2-F-phenyl | —SO$_2$CF$_3$ | 460 | 1A |
| 2-F-phenyl | —SO$_2$CH(CH$_3$)$_2$ | 434 | 1B |
| 3-CF$_3$-phenyl | —SO$_2$CH$_3$ | 456 | 1C |
| 2-CF$_3$-phenyl | —SO$_2$CH$_3$ | 456 | 1D |

-continued

| Y | R⁶ | MS (M + H) | Example |
|---|---|---|---|
| ![2-CF3-phenyl] | —SO₂CH(CH₃)₂ | 484 | 1E |
| ![2-CF3-phenyl] | —SO₂CF₃ | 510 | 1F |
| ![4-OCF3-phenyl] (F₃CO-) | —SO₂CH₃ | 472 | 1G |
| ![3-F-phenyl] | —SO₂CH₃ | 406 | 1H |
| ![3-F-phenyl] | —SO₂CF₃ | 460 | 1I |
| ![4-CF3-phenyl] (F₃C-) | —SO₂CH₃ | 456 | 1J |
| ![3,5-diF-phenyl] | —SO₂CH₃ | 424 | 1K |

EXAMPLE 2

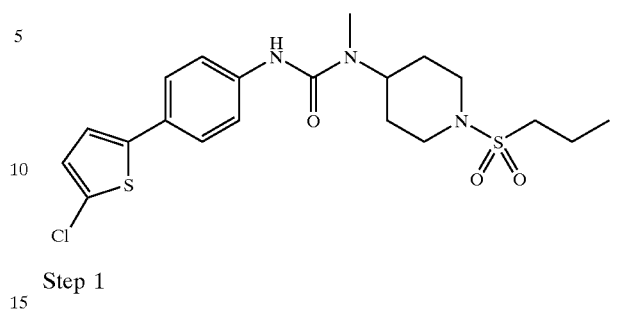

2

Step 1

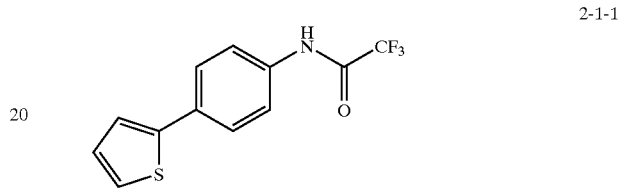

2-1-1

A stirred solution of 1 M 1-thienyllithium in THF (40 ml, 40 mmol) was cooled in a dry-ice/acetone bath under N₂. Triethylborate (8.5 ml, 50 mmol) was added, and the reaction mixture was allowed to warm to R.T. After 20 min., 4-iodoaniline (6.6 g, 30 mmol), Na₂CO₃ (4.5 g), H₂O (20 ml), and Pd(dppf)Cl₂.CH₂Cl₂ (750 mg, 0.9 mmol) were added. The reaction mixture was stirred under N2 until the exotherm was complete, then partitioned between Et₂O and H₂O. The Et₂O layer was washed with 1 N NaOH, dried (Na₂CO₃), and filtered through a pad of silica gel, eluting with Et₂O. The resultant brown solid was dissolved in CH₂Cl₂ (100 ml) and a solution of trifluoroacetic anhydride (8 ml, 57 mmol) in CH₂Cl₂ (100 ml) was added in portions with stirring. To the resultant suspension was added CH₂Cl₂ (450 ml) and the reaction mixture was stirred for 20 min. Water (200 ml) was added, followed by NaHCO₃ (7 g) in portions until CO₂ evolution ceased. The organic layer was stirred with MgSO₄ and DARCO, then filtered and concentrated to give a solid. The solid was dissolved in CH₂Cl₂ (50 ml) and to the stirred solution was added hexanes (100 ml). The solid was collected, washed with hexanes and dried to give the product (6.12 g, 75%). M.p. 213–216° C. Calcd for C₁₂H₈F₃NOS: C, 53.14; H, 2.58; N, 5.17. Found: C, 53.06; H, 2.85; N, 4.90%.

Step 2

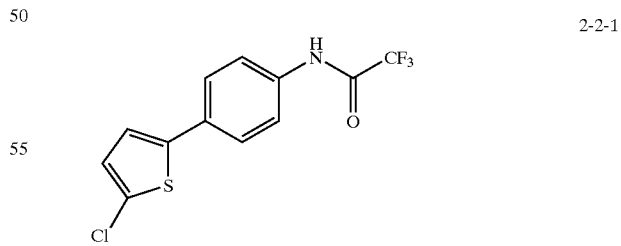

2-2-1

To a solution of the product of Step 1 (19.0 g, 70 mmol) in DMF (150 ml) was added N-chlorosuccinimide (10.1 g, 76 mmol) and trifluoroacetic acid (1.5 ml), and the reaction mixture was stirred under N₂ for 2 days. Water (500 ml) was added and the resultant solid was collected, washed with water and dried to give the product (20.6 g, 96%). M.P. 198–200° C. Calcd for C₁₂H₇ClF₃NOS: C, 47.12; H, 2.29; N, 4.58. Found: C, 47.19; H, 2.15; N, 4.47%.

Step 3

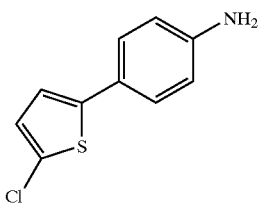

2-3-1

A mixture of the product of Step 2 (15.0 g, 49.1 mmol) and sodium hydroxide (19.6 g, 490 mmol) in MeOH (400 ml) and water (150 ml) was stirred at R.T. overnight. The mixture was concentrated in vacuo and the residue was partitioned between EtOAc and water. The organic layer was washed with water, brine, dried, and concentrated. The residue was purified by flash column (1:3 acetone/hexanes) to give the product (10.14 g, 98%). $^1$H-NMR (CDCl$_3$, 400 MHz) δ 7.32 (2H, m), 6.90 (1H, d, J=4.8 Hz), 6.83 (1H, d, J=4.8 Hz), 6.67 (2H, m), 3.76 (2H, b).

Step 4

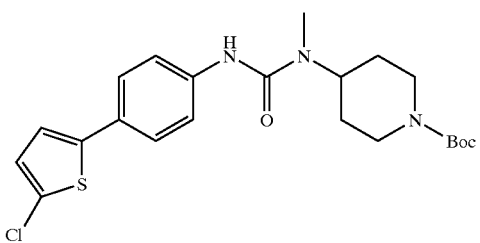

2-4-1

To a stirred, ice-cold solution of the product of Step 3 (2.0 g, 9.5 mmol) in THF (100 ml) was added pyridine (2.3 ml, 28 mmol) and N,N'-disuccinimidyl carbonate (2.44 g, 9.5 mmol). The reaction mixture was stirred at ice-bath temp. for 1.5 h, then Preparation 1 (2.04 g, 9.5 mmol) was added, and the reaction mixture was allowed to warm to R.T. After 16 h, the reaction mixture was concentrated, the residue was dissolved in EtOAc (200 ml) and washed with 2N HCl, sat'd NaHCO$_3$ and sat'd NaCl. The organic layer was dried (Na$_2$SO$_4$), filtered, and evaporated to afford the product (4.21 g, 98%) that was used directly in Step 5. HRMS calc. for C$_{22}$H$_{29}$ClN$_3$O$_3$S (M+H) 450.1618. Found 450.1623.

Step 5

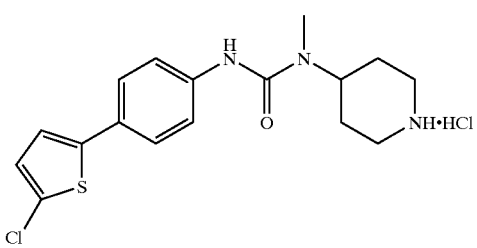

2-5-1

Reaction of the product of Step 4 (4.11 g, 9.13 mmol) with HCl by the procedure of Example 1, Step 3 afforded the product (3.71 g) that was used directly in Step 6. HRMS calc. for C$_{17}$H$_{21}$ClN$_3$OS (M+H) 350.1094. Found 350.1100.

Step 6

To a suspension of the product of Step 5 (50 mg, 0.13 mmol) in CH$_2$Cl$_2$ (3 ml) was added Et$_3$N (39 mg, 0.39 mmol) followed by n-propylsulfonyl chloride (20 mg, 0.14 mmol). The reaction mixture was stirred for 16 h. EtOAc (10 ml) was added and the mixture was washed with 2N HCl, sat'd NaHCO$_3$ and sat'd NaCl, dried (MgSO$_4$), filtered and concentrated. The residue was subjected to PTLC (3:97 MeOH/CH$_2$Cl$_2$) to give the product (37 mg, 62%). HRMS calc. for C$_{20}$H$_{27}$ClN$_3$O$_3$S$_2$ (M+H) 456.1182. Found 456.1179.

Reaction of the product of Step 5, 2-5-1, with the appropriate sulfonyl chloride in the presence of Et$_3$N gave the following examples.

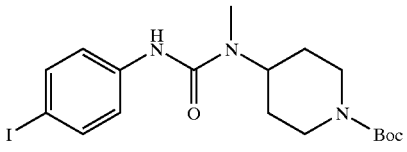

| R$^6$ | MS (M + H)+ | Example |
|---|---|---|
| —SO$_2$CH$_3$ | 428 | 2A |
| —SO$_2$CH$_2$CH$_3$ | 442 | 2B |
| —SO$_2$CH(CH$_3$)$_2$ | 456 | 2C |
| —SO$_2$CF$_3$ | 482 | 2D |
| —SO$_2$CH$_2$CF$_3$ | 496 | 2E |

EXAMPLE 3

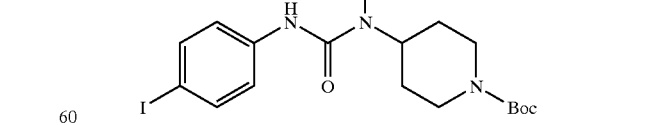

3

Step 1

3-1-1

Using the procedure of Example 1, Step 1, Preparation 1 (2.3 g, 107 mmol) was reacted with 4-iodophenyl isocyanate (2.6 g, 107 mmol). Purification by flash chromatography (2:98 MeOH/CH$_2$Cl$_2$) afforded a white solid.

Step 2

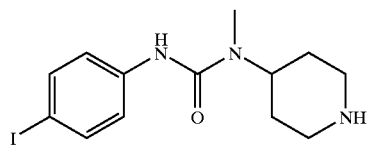

3-2-1

A mixture of the product of Step 1 (3.0 g, 6.7 mmol), 4M HCl in 1,4-dioxane (15 ml) and THF (15 ml) was stirred at ambient temp. for 5 h. The reaction mixture was concentrated to dryness, and H$_2$O (100 ml) and 3M NaOH (20 ml) was added to the residue. The whole was extracted with CH$_2$Cl$_2$ (3×100 ml). The combined organic extracts were dried (MgSO$_4$), filtered and evaporated. Flash chromatography (2:98 MeOH/CH$_2$Cl$_2$ then 10:90 (2M NH$_3$ in MeOH)/ CH$_2$Cl$_2$) gave a white solid (2.4 g, 100%). HRMS calc. for C$_{13}$H$_{19}$IN$_3$O (M+H) 360.0573. Found 360.0576.

Step 3

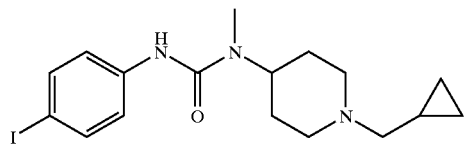

3-3-1

To a stirred ice-cold mixture of the product of Step 2 (2.4 g, 6.7 mmol) and cyclopropane carboxaldehyde (0.8 ml, 11 mmol) in CH$_2$Cl$_2$ (20 ml) was added NaBH(OAc)$_3$ (1.83 g, 10.8 mmol). The reaction mixture was allowed to warm to room temp. and stirred overnight. The reaction mixture was cooled in ice and 3M NaOH (5 ml) was added. After 0.5 h the mixture was extracted with CH$_2$Cl$_2$ (3×100 ml), dried (MgSO$_4$), filtered and evaporated. The residue was triturated with CH$_2$Cl$_2$/hexanes (1:10) to afford a white solid (2.4 g, 87%). HRMS calc. for C$_{17}$H$_{25}$IN$_3$O (M+H) 414.1038. Found 414.1042.

Step 4

A vessel charged with the product of Step 3 (200 mg, 0.48 mmol), 4-trifluoromethoxybenzeneboronic acid (250 mg, 1.21 mmol), tris(dibenzylideneacetone)dipalladium (0) (50 mg, 0.05 mmol), CsCO$_3$ (0.8 g, 2.5 mmol) and toluene (10 ml) was refluxed under N$_2$ for 3 h. The reaction mixture was allowed to cool, then EtOAc (50 ml) and H$_2$O (25 ml) were added. Solids were removed by filtration and the EtOAc layer was dried (Na$_2$SO$_4$), filtered, and evaporated. The residue was subjected to PTLC (3:7 acetone/hexanes then 10:90 (2M NH$_3$ in MeOH)/CH$_2$Cl$_2$) to give a pale yellow solid (50 mg, 23%). HRMS calc. for C$_{24}$H$_{29}$F$_3$N$_3$O$_2$ (M+H) 448.2212. Found 448.2215.

Using appropriate starting materials and essentially the same procedure, the following compounds were prepared:

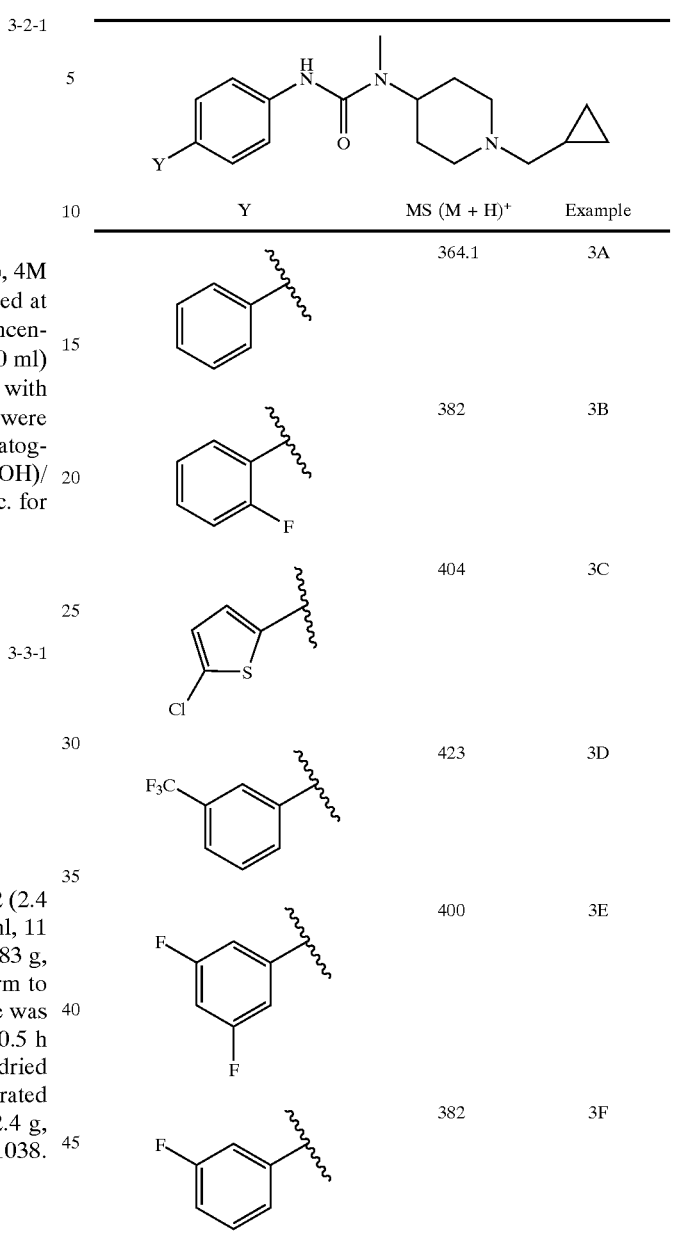

| Y | MS (M + H)$^+$ | Example |
|---|---|---|
| phenyl | 364.1 | 3A |
| 2-fluorophenyl | 382 | 3B |
| 5-chlorothien-2-yl | 404 | 3C |
| 3-trifluoromethylphenyl | 423 | 3D |
| 3,5-difluorophenyl | 400 | 3E |
| 3-fluorophenyl | 382 | 3F |

EXAMPLE 4

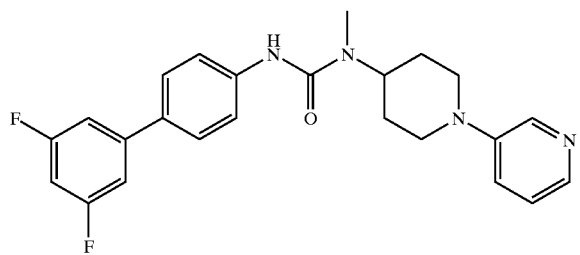

4

Step 1

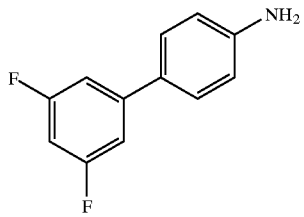
4-1-1

To an N$_2$-purged mixture of 4-bromonitrobenzene (20.0 g, 99.0 mmol), 3,5-difluorophenylboronic acid (23.4 g, 148 mmol) and Cs$_2$CO$_3$ (38.7 g, 119 mmol) in toluene (600 ml) and H$_2$O (30 ml) was added Pd(dppf)Cl$_2$.CH$_2$Cl$_2$ (4.04 g, 4.95 mmol). The reaction mixture was heated at 90° C. for 2 h, allowed to cool to R.T., then filtered through celite. The whole was extracted with EtOAc (3×500 ml). The combined organic layers were dried (Na$_2$SO$_4$), filtered, and concentrated to give a solid. To a vigorously stirred ice-cold mixture of the solid in CH$_3$OH (1 L) and NiCl$_2$.6H$_2$O (61.0 g, 257 mmol) was added NaBH$_4$ (14 g, 370 mmol) in portions. After the addition was complete, the reaction mixture was poured into H$_2$O (100 ml), then filtered through celite and extracted with EtOAc (3×500 ml). The combined organic layers were dried (Na$_2$SO$_4$), filtered, and concentrated. The residue was dissolved in EtOAc, and 1 N HCl/Et$_2$O (300 ml) was added. The precipitate was washed with hexane, air-dried, and dissolved in H$_2$O. The solution was neutralized by addition of 1 N NaOH, then extracted with CH$_2$Cl$_2$ (3×1 L). The combined organic layers were dried (Na$_2$SO$_4$), filtered, and concentrated to give the product (19.0 g, 94%). $^1$H NMR (CDCl$_3$, 400 MHz) δ 7.38 (2H, m), 7.06 (2H, m), 6.75 (2H, m), 6.72 (1H, m), 3.81 (s, 2H). MS m/e 206 (M+H).

Using the appropriate substituted phenylboronic acid starting material and essentially the same procedure, the following compounds were prepared:

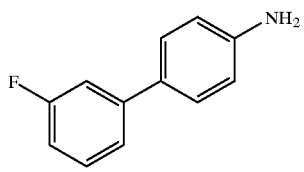
4-1-2

$^1$H NMR (CDCl$_3$, 400 MHz) δ 7.41–7.21 (5H, m), 7.33 (1H, m), 6.76 (2H, m), 3.76 (2H, b).

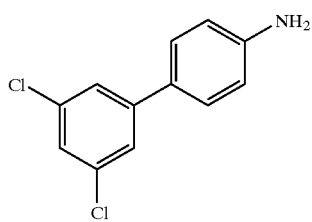
4-1-3

$^1$H NMR (CDCl$_3$, 400 MHz) δ 7.39 (2H, m), 7.24 (3H, m), 6.76 (2H, m), 3.80 (2H, b).

Additional arylamines were prepared from 4-iodoaniline according to the following procedure.

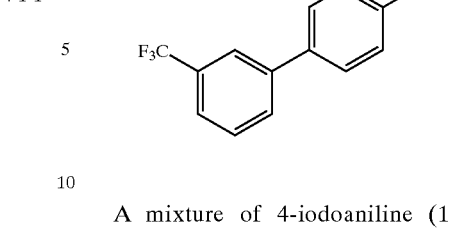
4-1-4

A mixture of 4-iodoaniline (1.00 g, 4.57 mmol), 3-trifluoromethylphenylboronic acid (1.30 g, 6.85 mmol) and Cs$_2$CO$_3$ (1.64 g, 5.02 mmol) in toluene (50 ml) and H$_2$O (3 ml) was purged with N$_2$ for 5 min. To the reaction mixture was added Pd(dppf)Cl$_2$.CH$_2$Cl$_2$ (746 mg, 0.91 mmol). The reaction mixture was heated at 90° C. for 5 h, then allowed to cool to R.T. and poured into cold water. The whole was extracted with CH$_2$Cl$_2$ (3×100 ml). The combined organic layers were dried (Na$_2$SO$_4$), filtered and evaporated. Purification of the residue by PTLC (EtOAc/hexane 1:2) gave the product (216 mg, 20%). $^1$H NMR (CDCl$_3$, 400 MHz) δ 7.77 (1H, m), 7.70 (1H, m), 7.51 (2H, m), 7.42 (2H, m), 6.78 (2H, m), 3.65 (2H, b).

Using the appropriate substituted phenylboronic acid starting material and essentially the same procedure, the following compounds were prepared.

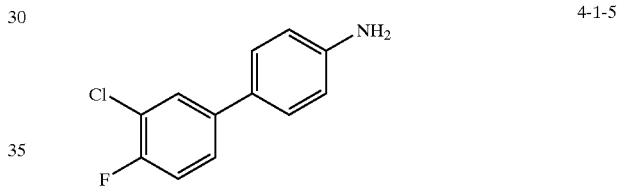
4-1-5

$^1$H NMR (CDCl$_3$, 400 MHz) δ 7.54 (1H, m), 7.34 (3H, m), 7.15 (1H, t, J=8.8 Hz), 6.75 (2H, m), 3.76 (2H, b).

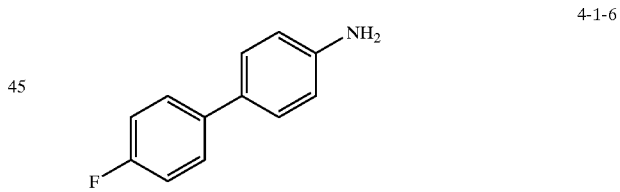
4-1-6

$^1$H NMR (CDCl$_3$, 400 MHz) δ 7.48 (2H, m), 7.35 (2H, d, J=6.4 Hz), 7.08 (2H, t, J=6.4 Hz), 6.76 (2H, d, J=6.4 Hz), 3.73 (2H, b). MS m/e 188 (M+H).

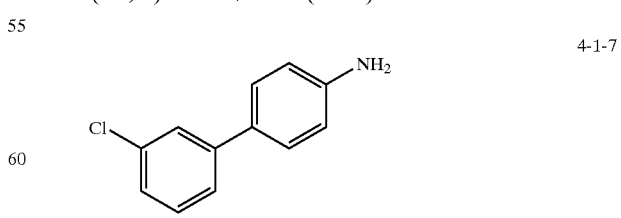
4-1-7

$^1$H NMR (CDCl$_3$, 400 MHz) δ 7.51 (1H, m), 7.41 (3H, m), 7.32 (1H, m), 7.23 (1H, m), 6.75 (2H, m), 3.78 (2H, b). MS m/e 204 (M+H).

Step 2

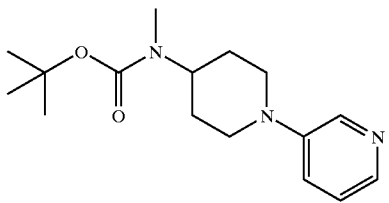

4-2-1

A stream of $N_2$ was passed through a mixture of the product of Preparation 2 (2.00 g, 9.33 mmol), 3-bromopyridine (2.95 g, 18.7 mmol) and 2-(di-tert-butylphosphino)biphenyl (0.139 g, 0.467 mmol) and NaOtBu (1.80 g, 18.7 mmol) in anhydrous toluene (10 ml). Pd(OAc)$_2$ (0.105 g, 0.467 mmol) was added and the reaction mixture was stirred at 110° C. for 24 h. The reaction mixture was allowed to cool to R.T. and poured into cold H$_2$O. The whole was extracted with CH$_2$Cl$_2$ (3×50 ml) and the combined organic layers were dried (Na$_2$SO$_4$), filtered, and concentrated. Purification of the residue by PTLC (1:20 CH$_3$OH/CH$_2$Cl$_2$) gave the product (1.47 g, 54%). $^1$H NMR (CDCl$_3$, 400 MHz) δ 8.29 (1H, s), 8.07 (1H, b), 7.17 (2H, m), 4.2 (1H, b), 3.74 (2H, m), 2.82 (2H, m), 2.74 (3H, s), 1.70 (4H, m), 1.45 (9H, s). MS m/e 292 (M+H).

Step 3

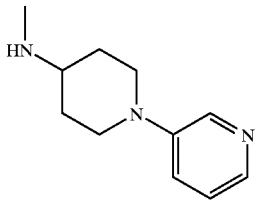

4-3-1

To the product of Step 2 (1.47 g, 5.05 mmol) was added 4M HCl/1,4-dioxane (20 ml). The reaction mixture was stirred at R.T. for 1.5 h and concentrated to afford the product in quantitative yield. $^1$H NMR (CD$_3$OD, 400 MHz) δ 8.46 (1H, s), 8.14 (2H, m), 7.86 (1H, s), 4.13 (2H, m), 3.40 (1H, b), 3.16 (2H, b), 2.75 (3H, s), 2.26 (2H, m), 1.76 (2H, m). MS m/e 192 (M+H).

Step 4

To a mixture of the product of Step 1 (4-1-1) (0.100 g, 0.487 mmol) and iPr$_2$NEt (0.43 ml, 2.44 mmol) in anhydrous toluene (10 ml) was added triphosgene (0.051 g, 0.171 mmol). The mixture was stirred at 120° C. for 2 h, then allowed to cool to R.T., and the product of Step 3 (4-3-1) (0.133 g, 0.585 mmol) was added. The reaction mixture was stirred at R.T. for 16 h, then poured into cold H$_2$O and extracted with CH$_2$Cl$_2$ (3×20 ml). The combined organic layers were dried (Na$_2$SO$_4$), filtered, and concentrated. The residue was purified by PTLC (1:20 CH$_3$OH/CH$_2$Cl$_2$) to give the product (0.114 g, 56%). $^1$H NMR (CDCl$_3$, 400 MHz) δ 8.33 (1H, d, J=2.4 Hz), 8.09 (1H, m), 7.49 (4H, m), 7.17 (2H, m), 7.06 (2H, m), 6.74 (1H, m), 6.51 (1H, s), 4.49 (1H, m), 3.77 (2H, m), 2.93 (3H, s), 2.91 (2H, m), 1.85 (4H, m). MS m/e 423 (M+H).

EXAMPLE 5

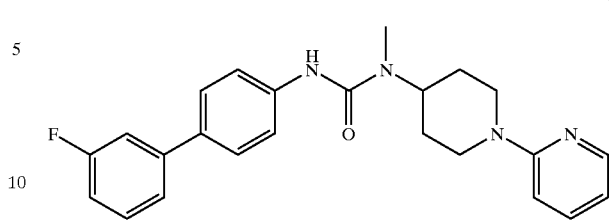

5

Step 1

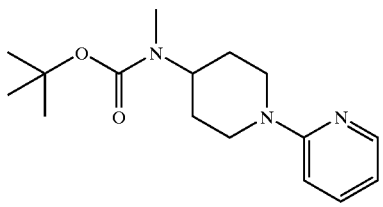

5-1-1

The product 5-1-1 was prepared in 57% yield from 2-bromopyridine and Preparation 2 by the procedure of Example 4, Step 2, except that 2-(di-tert-butylphosphino) biphenyl was replaced by 1,3-bis(diphenylphosphino) propane, and a reaction temperature of 80° C. instead of 110° C. was used. MS m/e 292 (M+H).

Step 2

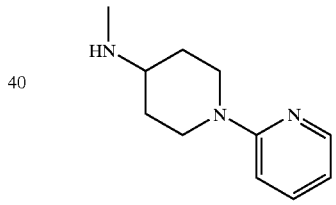

5-2-1

Treatment of the product of Step 1 with 4 N HCl/dioxane by the procedure of Example 4, Step 3 gave the product. MS m/e 192 (M+H).

Step 3

To a stirred ice-cold mixture of 4-1-2 (0.063 g, 0.339 mmol) and pyridine (0.14 ml, 1.69 mmol) in anhydrous THF (10 ml) was added N,N'-disuccinimidyl carbonate (0.087 g, 0.339 mmol). The reaction was stirred in an ice-bath for 25 min. then the product of Step 2, 5-2-1(0.100 g, 0.508 mmol), was added. The reaction was allowed to warm to R.T., stirred for 16 h, then poured into cold H$_2$O (20 ml). The whole was extracted with CH$_2$Cl$_2$ (3×20 ml), the combined organic layers were dried (Na$_2$SO$_4$), filtered, and concentrated. The residue was subjected to PTLC (1:20 CH$_3$OH/ CH$_2$Cl$_2$) to give the product (0.080 g, 58%). $^1$H NMR (CDCl$_3$, 400 MHz) δ 8.19 (1H, m), 7.52 (5H, m), 7.37 (2H, m), 7.27 (1H, m), 6.99 (1H, m), 6.69 (1H, d), 6.62 (1H, m), 6.45 (1H, s), 4.56 (1H, m), 4.42 (2H, m), 2.92 (2H, m), 2.88 (3H, s), 1.78 (4H, m). MS m/e 405 (M+H).

EXAMPLE 6

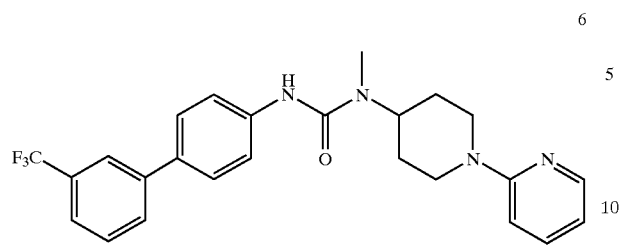

Reaction of 4-1-4, N,N'-disuccinimidyl carbonate and 5-2-1 by the procedure of Example 5, Step 3 afforded the product. MS m/e 455 (M+H).

EXAMPLE 7

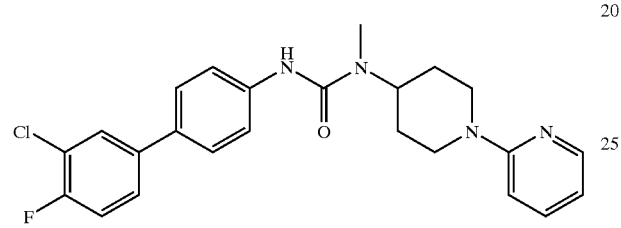

Reaction of 4-1-5, N,N'-disuccinimidyl carbonate and 5-2-1 by the procedure of Example 5, Step 3 afforded the product. MS m/e 473 (M+H).

EXAMPLE 8

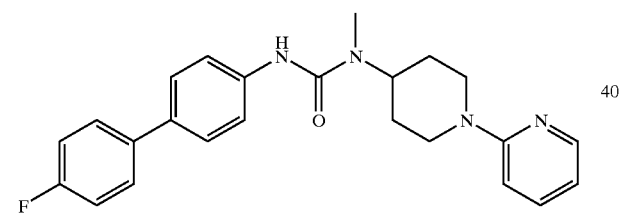

Reaction of 4-1-6, N,N'-disuccinimidyl carbonate and 5-2-1 by the procedure of Example 5, Step 3 afforded the product. MS m/e 405 (M+H).

EXAMPLE 9

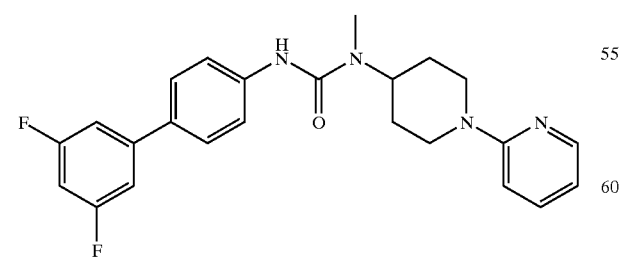

Reaction of 4-1-1, N,N'-disuccinimidyl carbonate and 5-2-1 by the procedure of Example 5, Step 3 afforded the product. MS m/e 423 (M+H).

EXAMPLE 10

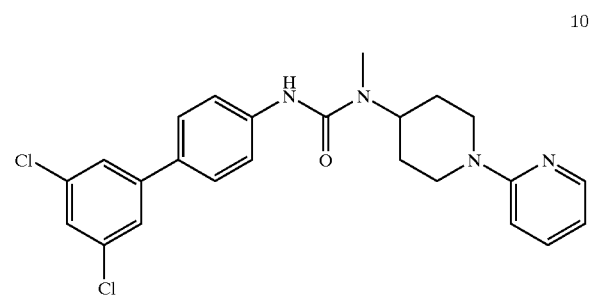

Reaction of 4-1-3, triphosgene and 5-2-1 by the procedure of Example 4, Step 4 afforded the product. MS m/e 455 (M+H).

EXAMPLE 11

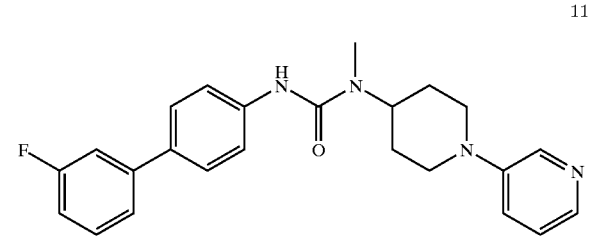

Reaction of 4-1-2, triphosgene and 4-3-1 by the procedure of Example 4, Step 4 afforded the product. MS m/e 405 (M+H).

EXAMPLE 12

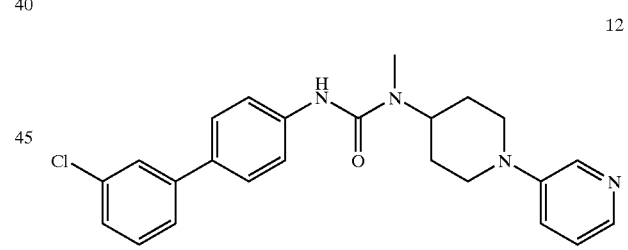

Reaction of 4-1-7, triphosgene and 4-3-1 by the procedure of Example 4, Step 4 afforded the product. MS m/e 421 (M+H).

EXAMPLE 13

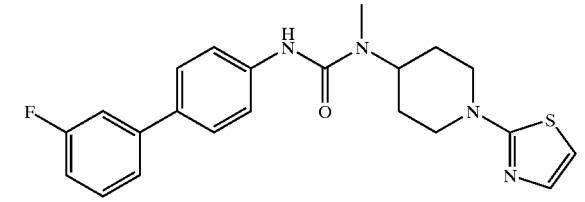

Step 1

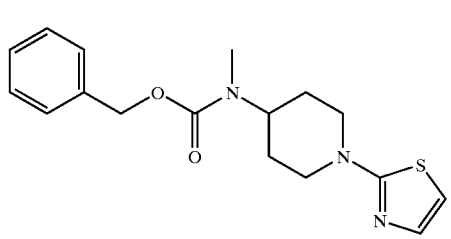

13-1-1

A mixture of Preparation 3 (2.75 g, 9.7 mmol), 2-bromothiazole (1.98 g, 12.1 mmol), and $K_2CO_3$ (3.5 g, 25 mmol) in DMF (40 ml) was heated at 160° C. for 20 h. The reaction mixture was concentrated and partitioned between $CH_2Cl_2$ and $H_2O$. The organic layer was washed with sat'd NaCl, dried ($MgSO_4$), filtered and concentrated. Flash chromatography (gradient; $CH_2Cl_2$ to 2:98 MeOH/$CH_2Cl_2$) gave the product (2.0 g, 62%). MS m/e 332.1 (M+H).

Step 2

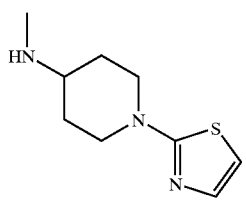

13-2-1

The product of Step 1 (2.0 g, 6.0 mmol) and 33% HBr in AcOH (40 ml) was stirred at R.T. for 2 h. The reaction mixture was evaporated and the residue was partitioned between 1 N NaOH and $CH_2Cl_2$. The organic layer was washed with sat'd NaCl, dried ($MgSO_4$), filtered and evaporated. Flash chromatography (gradient; 2:98 (2M $NH_3$ in MeOH)/$CH_2Cl_2$ to 15:85 (2M $NH_3$ in MeOH)/$CH_2Cl_2$) gave the product (0.94 g, 79%) as a yellow solid. $^1$H NMR (CDCl$_3$, 400 MHz) δ 7.04 (1H, d, J=4 Hz), 6.52 (1H, d, J=4 Hz), 3.96 (2H, m), 3.17 (1H, m), 2.99 (2H, m), 2.59 (3H, s), 2.16 (2H, m), 1.68 (2H, m). MS m/e 198 (M+H).

Step 3

Reaction of 4-1-2, triphosgene and 13-2-1 by the procedure of Example 4, Step 4 afforded the product. MS m/e 411 (M+H).

EXAMPLE 14

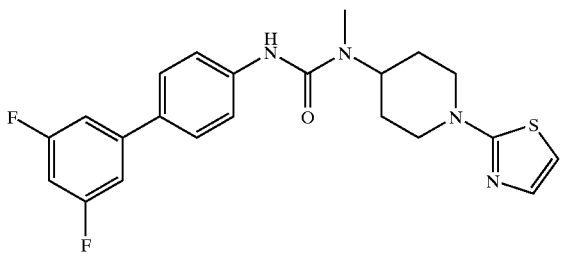

14

Reaction of 4-1-1, triphosgene and 13-2-1 by the procedure of Example 4, Step 4 afforded the product. MS m/e 429 (M+H).

EXAMPLE 15

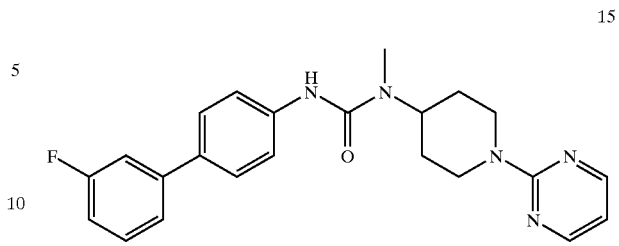

15

Step 1

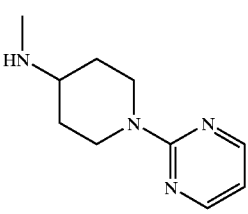

15-1-1

An $N_2$-purged mixture of 2-bromopyrimidine (400 mg, 2.52 mmol), Preparation 3 (510 mg, 1.79 mmol), Pd(OAc)$_2$ (18 mg, 0.08 mmol), sodium tert-butoxide (516 mg, 5.37 mmol), and (1,3-bis-diphenylphosphino)propane (29 mg, 0.07 mmol) in toluene (6 ml) was stirred at 70° C. in a sealed vessel for 16 h. The reaction mixture was allowed to cool to R.T., and 1 N NaOH (20 ml) was added. The whole was extracted with $CH_2Cl_2$ (3×20 ml), and the combined $CH_2Cl_2$ extracts were dried (MgSO$_4$), filtered, and evaporated. The residue was subjected to PTLC (2:98 MeOH/$CH_2Cl_2$) to give the product (464 mg, 79%). MS m/e 327 (M+H).

Step 2

15-2-1

The product of Step 1 (464 mg, 1.43 mmol) and 10% Pd/C (59 mg) in EtOH (20 ml) was stirred under 1 atm. of $H_2$ for 16 h. The catalyst was removed by filtration through celite and the filter pad was washed with EtOH. The combined filtrate and washings were evaporated. The residue was subjected to PTLC (5:95 (2M $NH_3$ in MeOH)/$CH_2Cl_2$) to give the product (464 mg, 79%). $^1$H NMR (CDCl$_3$, 400 MHz) δ 8.28 (2H, m), 6.44 (1H, m), 4.66 (2H, m), 2.99 (2H, m), 2.65 (1H, m), 2.47 (3H, s), 1.96 (2H, m), 1.33 (2H, m). MS m/e 193 (M+H).

Step 3

Reaction of the product of Step 2 (15-2-1) with 4-1-2 with triphosgene by the procedure of Example 4, Step 4 gave the product. MS (m/e) 406 (M+H).

EXAMPLE 16

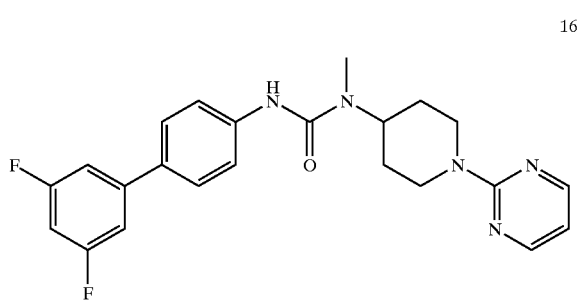

Reaction of the product of Example 15, Step 2 (15-2-1) and 4-1-1 with triphosgene by the procedure of Example 4, Step 4 gave the product. MS (m/e) 424 (M+H).

EXAMPLE 17

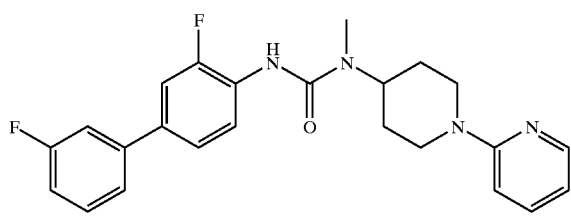

Step 1

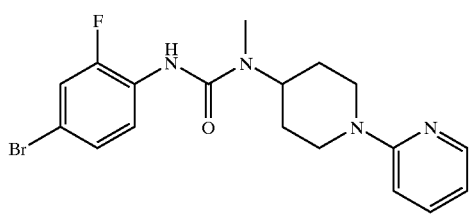

Reaction of the product of Example 5, Step 2 with 4-bromo-2-fluorophenylisocyanate by the procedure of Example 1, Step 1 gave the product. $^1$H NMR (CDCl$_3$, 400 MHz) δ 8.18 (1H, m), 7.47 (1H, m), 7.38 (2H, m), 7.30 (2H, m), 6.68 (1H, m), 6.61 (1H, m), 4.49 (1H, m), 4.43 (2H, m), 2.91 (2H, m), 2.85 (3H, s), 1.71 (4H, m). MS m/e 391 (M+H). Step 2

Reaction of the product of Step 1 with 3-fluorophenylboronic acid by the procedure of Example 4, Step 1 gave the product. MS m/e 423 (M+H).

EXAMPLE 18

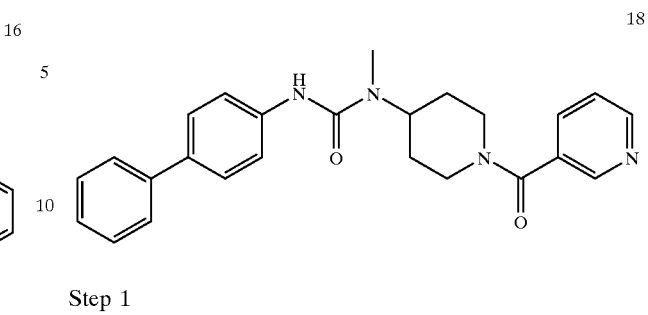

Step 1

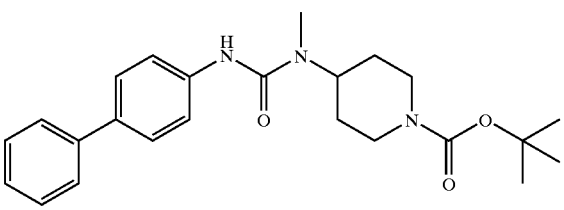

A mixture of 4-biphenyl isocyanate (3.00 g, 15.4 mmol) and Preparation 1 (5.33 g, 25.0 mmol) in CH$_2$Cl$_2$ (100 ml) was stirred at R.T. for 16 h. The mixture was washed with water (25 ml), 3N HCl (25 ml), and brine (50 ml). The organic portion was dried (MgSO$_4$), filtered, concentrated, and purified by column chromatography (gradient; CH$_2$Cl$_2$ to 1:99 CH$_3$OH/CH$_2$Cl$_2$) to give the product (6.11 g, 97%). MS (ES) m/e 410 (M+H)$^+$.
Step 2

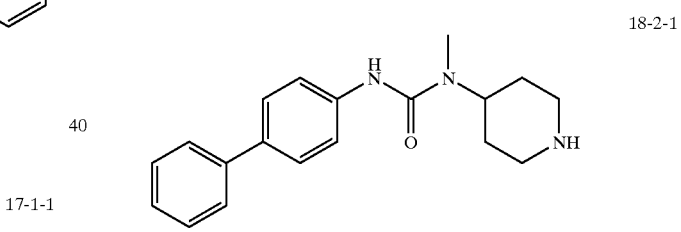

A mixture of the product of Step 1 (6.11 g, 14.9 mmol) and 4N HCl/dioxane (100 ml) was stirred at R.T. for 5 h. The volatiles were evaporated and the residue was triturated with ether. The precipitate was collected, dissolved in water (200 ml), basified to pH 14, and extracted with CH$_2$Cl$_2$ (300 ml). The organic portion was dried and concentrated to give the product (4.39 g, 92%). MS (ES) m/e 310 (M+H)$^+$.
Step 3

A solution of the product of Step 2 (80 mg, 0.26 mmol), nicotinoyl chloride hydrochloride (54 mg, 0.30 mmol), and triethylamine (90 µl, 0.64 mmol) in CH$_2$Cl$_2$ (2 ml) was stirred at R.T. for 16 h. The mixture was diluted with CH$_2$Cl$_2$ (50 ml) and extracted with 3N NaOH (5 ml). The organic layer was washed with water (15 ml), dried, (MgSO$_4$), filtered, and concentrated. The residue was subjected to PTLC (4:96 CH$_3$OH/CH$_2$Cl$_2$) to give the product (90 mg, 84%). $^1$H NMR (CDCl$_3$, 400 MHz) δ 8.68 (2H, m), 7.76 (1H, m), 7.2–7.6 (10H, m), 6.48 (1H, s), 4.85 (1H, m), 4.60 (1H, m), 3.80 (1H, m), 3.20 (1H, m), 2.91 (3H, s), 2.86 (1H, m), 1.4–2.0 (4H, m). MS (ES) m/e 415 (M+H)$^+$.

Using the appropriate acid chloride and essentially the same procedure the following compounds were prepared.

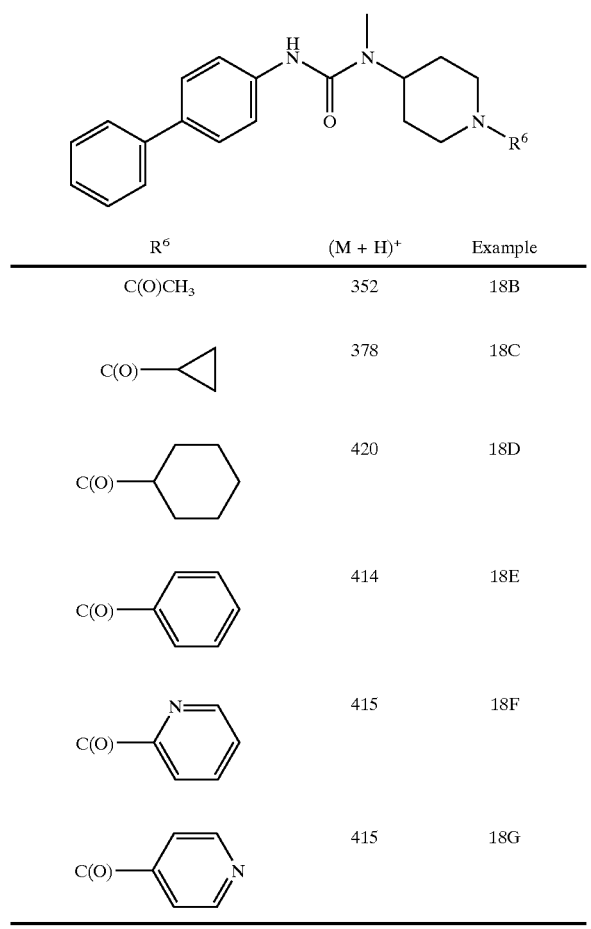

| R[6] | (M + H)[+] | Example |
|---|---|---|
| C(O)CH₃ | 352 | 18B |
| C(O)-cyclopropyl | 378 | 18C |
| C(O)-cyclohexyl | 420 | 18D |
| C(O)-phenyl | 414 | 18E |
| C(O)-2-pyridyl | 415 | 18F |
| C(O)-4-pyridyl | 415 | 18G |

EXAMPLE 19

Reaction of Example 1, 1-3-5, with the appropriate acid chloride afforded the following compounds:

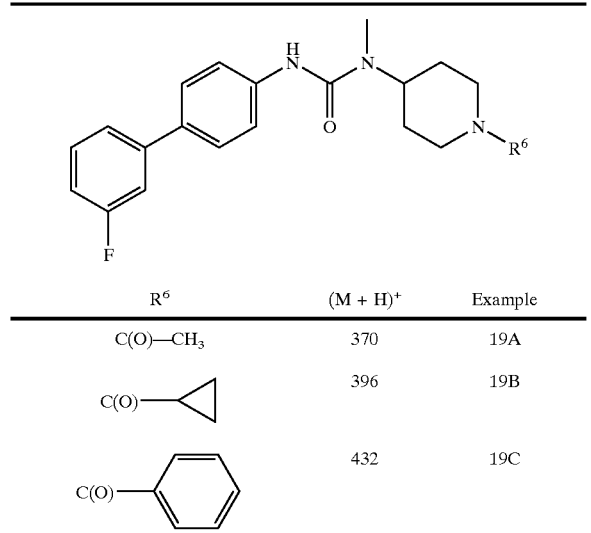

| R[6] | (M + H)[+] | Example |
|---|---|---|
| C(O)—CH₃ | 370 | 19A |
| C(O)-cyclopropyl | 396 | 19B |
| C(O)-phenyl | 432 | 19C |

-continued

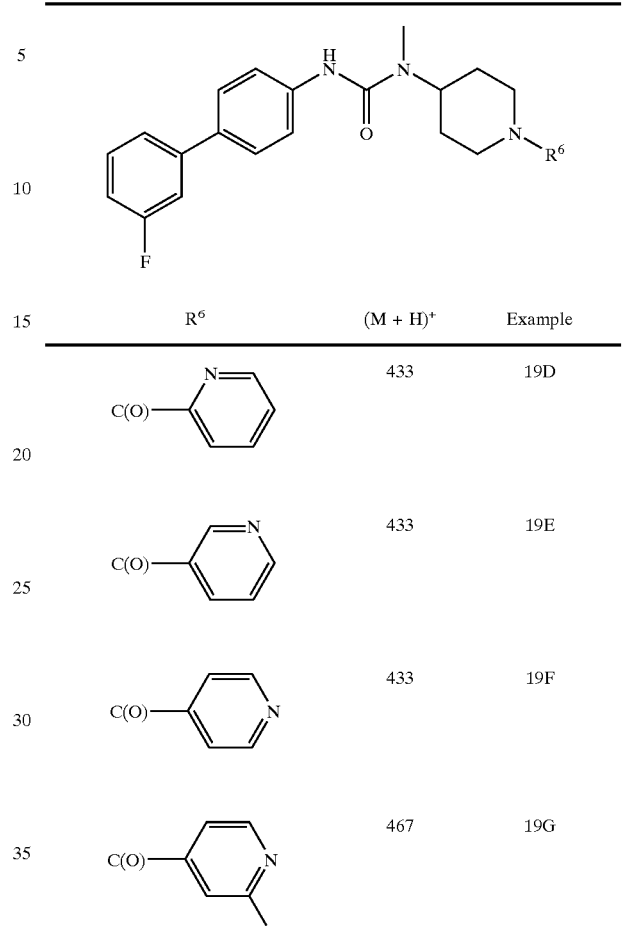

| R[6] | (M + H)[+] | Example |
|---|---|---|
| C(O)-2-pyridyl | 433 | 19D |
| C(O)-3-pyridyl | 433 | 19E |
| C(O)-4-pyridyl | 433 | 19F |
| C(O)-(2-chloro-4-pyridyl) | 467 | 19G |
| C(O)-(2,6-dichloro-4-pyridyl) | 501 | 19H |
| C(O)-(2-chloro-6-methyl-4-pyridyl) | 481 | 19I |
| C(O)-(2-chloro-6-methoxy-4-pyridyl) | 497 | 19J |

EXAMPLE 20

Reaction of the product of Example 1, 1-3-7, with the appropriate acid chloride afforded the following compounds:

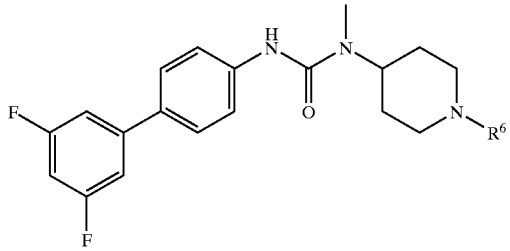

| R | (M + H)⁺ | Example |
|---|---|---|
| C(O)—CH₃ | 388 | 20A |
| C(O)-cyclopropyl | 414 | 20B |
| C(O)-phenyl | 450 | 20C |
| C(O)-2-pyridyl | 451 | 20D |
| C(O)-3-pyridyl | 451 | 20E |
| C(O)-4-pyridyl | 451 | 20F |

EXAMPLE 21

Reaction of the product of Example 2, Step 5, 2-5-1, with the appropriate acid chloride afforded the following compounds

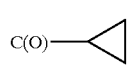

| R⁶ | (M + H)⁺ | Example |
|---|---|---|
| C(O)—CH₃ | 392 | 21A |
| C(O)-cyclopropyl | 418 | 21B |
| C(O)-phenyl | 454 | 21C |
| C(O)-2-pyridyl | 455 | 21D |
| C(O)-3-pyridyl | 455 | 21E |
| C(O)-4-pyridyl | 455 | 21F |

EXAMPLE 22

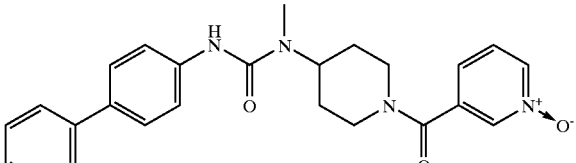

A mixture of Example 18 (45 mg, 0.11 mmol) and 3-chloroperoxybenzoic acid (40 mg) in CH₂Cl₂ (5 ml) was stirred at R.T. for 16 h. The mixture was diluted with CH₂Cl₂ (50 ml), then washed with 3N NaOH (2×5 ml) and water (10 ml). The organic layer was dried (Na₂SO₄), filtered, and concentrated. The residue was subjected to PTLC (1:9 CH₃OH/CH₂Cl₂) to give the product (34 mg, 73%). ¹H NMR (CDCl₃, 400 MHz) δ 8.20 (2H, m), 7.2–7.6 (11H, m), 6.56 (1H, s), 4.76 (1H, m), 4.59 (1H, m), 3.78 (1H, m), 3.22 (1H, m), 2.7–3.0 (4H, m), 1.4–2.0 (4H, m). MS (ES) m/e 431 (M+H)⁺.

EXAMPLE 23

23

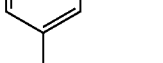

Step 1

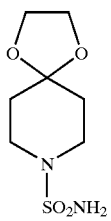

A mixture of 4-piperidone ethylene ketal (0.64 ml, 5.0 mmol) and sulfamide (0.53 g, 5.5 mmol) in DME (20 ml) was refluxed for 16 h. The mixture was concentrated to ca. 3 ml, dissolved in EtOAc (175 ml), washed with sat'd NH$_4$Cl (2×25 ml), water (2×25 ml), and brine (25 ml). The organic portion was dried, filtered, and evaporated to give the product (0.58 g, 52%). MS (ES) m/e 223 (M+H)$^+$.

Step 2

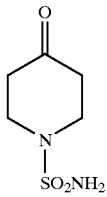

A mixture of the product of Step 1 (560 mg, 2.52 mmol) and pyridinium 4-toluenesulfonate (190 mg, 0.756 mmol) in acetone (25 ml) and water (0.5 ml) was refluxed for 64 h. The mixture was evaporated to dryness and the residue was partitioned between CH$_2$Cl$_2$ (75 ml) and aq. NaHCO$_3$ (2×20 ml). The aqueous layer was extracted with CH$_2$Cl$_2$ and EtOAc sequentially. The EtOAc layer was evaporated to give the product (140 mg). $^1$H NMR (CD$_3$OD, 400 MHz) δ 3.47 (1H, t, J=6.4 Hz), 3.15 (3H, m), 2.54 (1H, t, J=6.4 Hz), 1.81 (3H, m).

Step 3

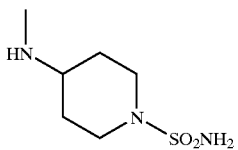

A mixture of the product of Step 2 (135 mg, 0.757 mmol), 40% aqueous methylamine (300 μl, 2.42 mmol), and sodium triacetoxyborohydride (375 mg, 1.77 mmol) in dichloroethane (5 ml) was stirred at R.T. for 19 h. The mixture was partitioned between 3N NaOH (5 ml) and EtOAc (3×50 ml). The organic layer was concentrated to give the crude product (40 mg). The aqueous layer was evaporated in vacuo to dryness and the residue was suspended in EtOAc. The suspension was filtered and the filtrate concentrated to give another batch of the product (70 mg). MS (FAB) m/e 194 (M+H)$^+$.

Step 4

To an ice-cold solution of 4-1-2 (40 mg, 0.21 mmol) in anhydrous THF (3 ml) was added N,N'-disuccinimidyl carbonate (55 mg, 0.21 mmol) and pyridine (52 μl, 0.65 mmol). The mixture was stirred at 0° C. for 2 h and the product of Step 3 (70 mg, 0.36 mmol) was added. After stirring at R.T. for 2 h the reaction mixture was taken up in CH$_2$Cl$_2$ (50 ml), washed with 1N HCl (10 ml), dried, (Na$_2$SO$_4$), filtered and concentrated. The residue was subjected to PTLC (5:95 CH$_3$OH/CH$_2$Cl$_2$) to give the product (62 mg, 71%).

$^1$H NMR (CD$_3$OD, 400 MHz) δ 7.56 (2H, m), 7.48 (2H, m), 7.40 (2H, m), 7.32 (1H, m), 7.02 (1H, m), 4.23 (1H, m), 3.75 (2H, m), 2.94 (3H, s), 2.72 (2H, m), 1.7–2.0 (4H, m). MS (ES) m/e 407 (M+H)$^+$.

Using the appropriate starting materials and essentially the same procedure afforded the following compounds.

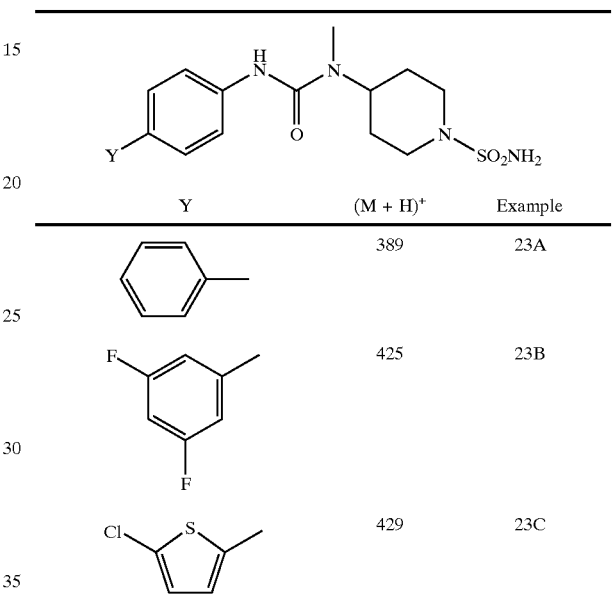

| Y | (M + H)$^+$ | Example |
|---|---|---|
| | 389 | 23A |
| | 425 | 23B |
| | 429 | 23C |

EXAMPLE 24

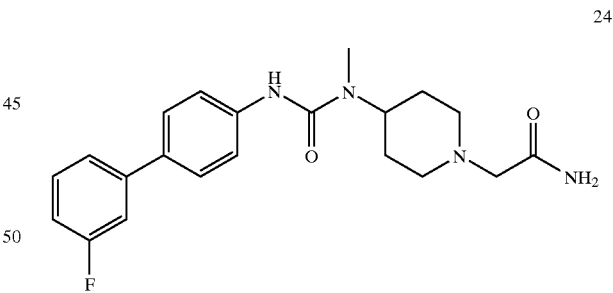

A mixture of 1-3-5 (71 mg, 0.20 mmol), 2-bromoacetamide (32 mg, 0.23 mmol), and anhydrous potassium carbonate (170 mg, 1.20 mmol) in CH$_3$CN (2 ml) in a sealed tube was heated to 45° C. for 6 h. The mixture was diluted with CH$_2$Cl$_2$ (75 ml), washed with water (50 ml), dried, and concentrated. The residue was subjected to PTLC (5:95 CH$_3$OH/CH$_2$Cl$_2$) to give the product (37 mg, 49%). $^1$H NMR (CDCl$_3$, 400 MHz) δ 7.48 (4H, m), 7.35 (2H, m), 7.23 (1H, m), 6.98 (2H, m), 6.56 (1H, s), 5.97 (1H, bs), 4.25 (1H, m), 2.8–3.0 (7H, m), 2.31 (2H, m), 1.6–1.8 (4H, m). MS (ES) m/e 385 (M+H)$^+$.

EXAMPLE 25

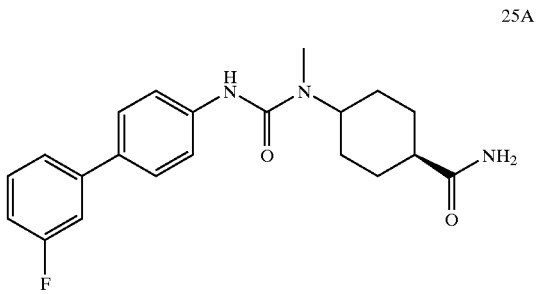

Step 1

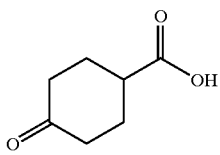

To ethyl 4-oxocyclohexanecarboxylate (10 g, 59 mmol) in MeOH (75 ml) and water (50 ml) was added lithium hydroxide monohydrate (4.2 g, 100 mmol) at 0° C. The mixture was warmed up to R.T. and stirred for 3 h. The mixture was acidified to pH 2 with 3N HCl. The volatiles were evaporated and the residue was extracted with EtOAc (300 ml). The organic portion was dried and concentrated to give the product (8.01 g, 96%). MS (Cl) m/e 143 (M+H)$^+$.

Step 2

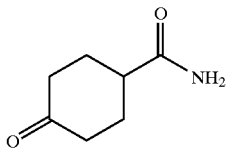

2M oxalyl chloride in $CH_2Cl_2$ (20 ml, 40 mmol) was added over 5 min to a solution of the product of Step 1 (3.0 g, 21 mmol) in anhydrous THF (50 ml). The solution was heated to 80° C. for 6 h and then evaporated to dryness. The residue was dissolved in THF (50 ml) at 0° C. and aq. $NH_4OH$ (6.0 ml, 89 mmol) was added. After stirring at R.T. for 16 h, the mixture was concentrated and the residue purified by column chromatography (gradient $CH_2Cl_2$ to 2:98 $CH_3OH/CH_2Cl_2$) to give the product (762 mg, 26%). MS (Cl) m/e 142 (M+H)$^+$.

Step 3

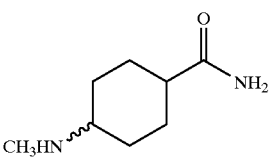

A mixture of the product of Step 2 (800 mg, 5.71 mmol), 40% aq. methylamine (4.0 ml, 52 mmol), and sodium triacetoxyborohydride (1.7 g, 8.0 mmol) in dichloroethane (20 ml) was stirred at R.T. for 16 h. The reaction was quenched with 3N NaOH and partitioned between brine and 1:1 $CH_3CN/CH_2Cl_2$. The organic portion was concentrated and the residue purified by column chromatography (gradient $CH_2Cl_2$ to 1:4 2M $NH_3$ in $CH_3OH/CH_2Cl_2$) to give the product (450 mg, 51%). MS (Cl) m/e 157 (M+H)$^+$.

Step 4

A mixture of the aniline 4-1-2 (100 mg, 0.534 mmol), N,N'-disuccinimidyl carbonate (137 mg, 0.535 mmol), and pyridine (0.13 ml, 1.6 mmol) in THF (3 ml) was stirred at 0° C. for 2 h. To this mixture was added the product of Step 3 (125 mg, 0.811 mmol) and the reaction was stirred at R.T. for 2 h. The mixture was diluted with $CH_2Cl_2$ (100 ml), washed with 1 N HCl (2×25 ml), water (2×25 ml), brine (25 ml), dried, and concentrated. The residue was subjected to PTLC (3:97 $CH_3OH/CH_2Cl_2$) to give the cis-product (14 mg) and the trans-product (15 mg).

cis-Product 25A:

$^1$H NMR (CD$_3$OD, 400 MHz): δ 7.4–7.6 (4H, m), 7.33 (2H, m), 7.22 (1H, m), 6.95 (1H, m), 4.13 (1H, m), 2.86 (3H, s), 2.53 (1H, m), 2.13 (2H, m), 1.82 (2H, m), 1.5–1.75 (4H, m). MS (ES) m/e 370 (M+H)$^+$.

trans-Product 25B:

$^1$H NMR (CD$_3$OD, 400 MHz): δ 7.4–7.5 (4H, m), 7.34 (2H, m), 7.23 (1H, m), 6.96 (1H, m), 4.07 (1H, m), 2.88 (3H, s), 2.14 (1H, m), 1.98 (2H, m), 1.81 (2H, m), 1.5–1.7 (4H, m). MS (ES) m/e 370 (M+H)$^+$.

Reaction of the Product of Step 3, 25-3-1 with Aniline 4-1-1 by Essentially the Same Procedure Gave 25C and 25D:

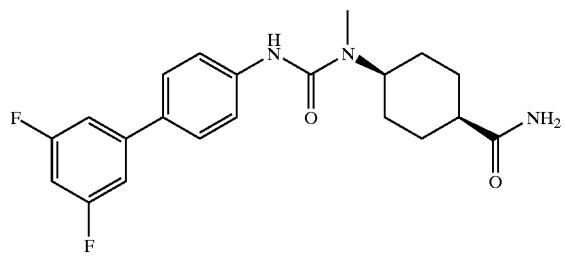

25C MS (ES) m/e 388 (M+H)+

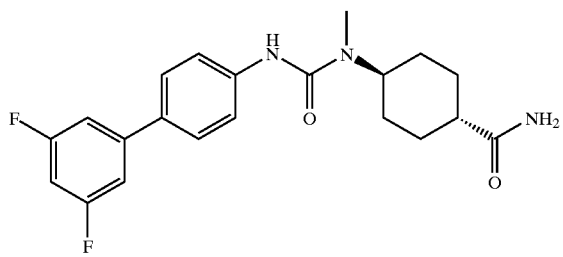

25D MS(ES) m/e 388 (M+H)+

EXAMPLE 26

26

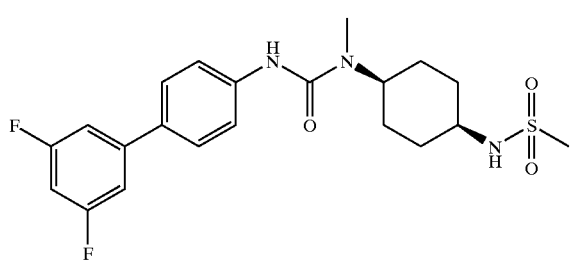

Step 1

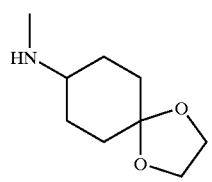

26-1-1

To a stirred mixture of 1,4-cyclohexanedione monoethylene ketal (4.68 g, 30 mmol) and 40% w/w aq. methylamine (6.0 mL) in 1,2-dichloroethane (75 mL), was added Na(OAc)$_3$BH (9.6 g, 45 mmol) in portions. The reaction mixture was vigorously stirred for 16 h, then 1 N NaOH (75 mL) was added. The organic layer was washed with sat'd NaCl, dried (MgSO$_4$), filtered, and evaporated to give an oil (4.60 g, 90%) that was used without further purification. $^1$H NMR (CDCl$_3$, 400 MHz) δ 3.97 (4H, s), 2.47 (1H, m), 2.46 (3H, s), 1.91 (2H, m), 1.80 (2H, m), 1.59 (2H, m), 1.45 (2H, m).

Step 2

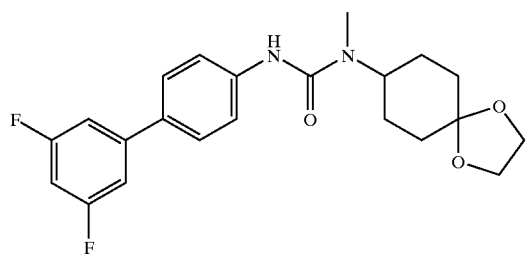

26-2-1

To a stirred, ice-cold mixture of aniline 4-1-1 (1.00 g, 4.87 mmol) and pyridine (1.97 ml, 24.3 mmol) in anhydrous THF (50 ml) was added disuccinimidyl carbonate (1.25 g, 4.87 mmol). The reaction mixture was stirred at 0° C. for 1 h and the product of Step 1 (1.25 g, 7.31 mmol) was added. The reaction mixture was allowed to warm to R.T., stirred for 16 h, then poured into cold H$_2$O (100 ml). The whole was extracted with CH$_2$Cl$_2$ (3×100 ml). The combined organic layers were dried (Na$_2$SO$_4$), filtered, and evaporated. Purification of the residue by column chromatography (1:20 CH$_3$OH/CH$_2$Cl$_2$) afforded the product (1.40 g, 71%). $^1$H NMR (CDCl$_3$, 400 MHz) δ 7.49 (4H, m), 7.10 (2H, m), 6.70 (1H, m), 6.60 (1H, s), 4.30 (1H, m), 3.90 (4H, s), 2.90 (3H, s), 1.75 (8H, m). MS m/e 403 (M+H).

Step 3

26-3-1

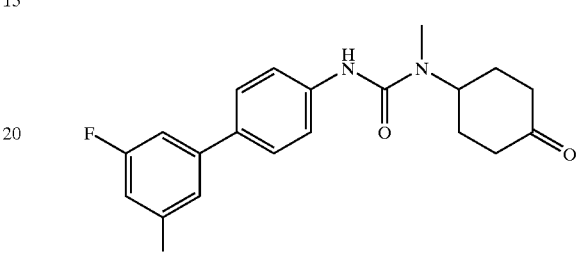

To the product of Step 2 (1.30 g, 3.23 mmol) in THF (30 ml) was added 5N HCl (20 ml). The reaction mixture was stirred at R.T. for 4.5 h, then extracted with CH$_2$Cl$_2$ (3×100 ml). The combined organic extracts were washed with sat'd NaHCO$_3$, dried (Na$_2$SO$_4$), filtered and evaporated. The residue was purified by PTLC (1:20 CH$_3$OH/CH$_2$Cl$_2$) to give the product (0.80 g, 69%). $^1$H NMR (CDCl$_3$, 400 MHz) δ 7.50 (4H, m), 7.10 (2H, m), 6.80 (1H, m), 6.50 (1H, s), 4.80 (1H, m), 2.90 (3H, s), 2.48 (4H, m), 2.10 (2H, m), 1.90 (2H, m). MS m/e 359 (M+H).

Step 4

26-4-1

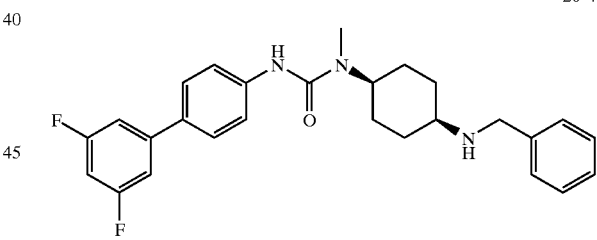

26-4-2

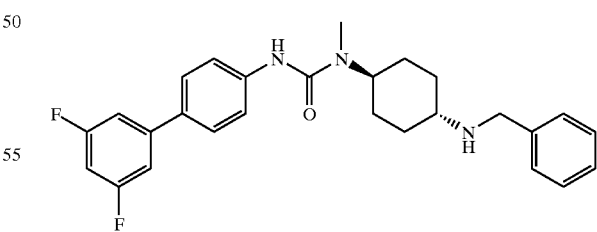

To a mixture of the product of Step 3 (0.43 g, 1.20 mmol) and benzylamine (0.257 g, 2.40 mmol) in 1,2-dichloroethane (10 ml) was added NaBH(OAc)$_3$ (0.762 g, 3.60 mmol) in portions. The reaction mixture was stirred at R.T. for 4.5 h, then poured into sat'd NaHCO$_3$ (20 ml) and extracted with CH$_2$Cl$_2$ (3×20 ml). The combined organic layers were dried (Na$_2$SO$_4$), filtered and evaporated. The residue was purified by PTLC (1:20 (2M NH$_3$/CH$_3$OH):CH$_2$Cl$_2$) to produce the cis-isomer 26-4-1 (0.240 g, 44.5%) and the trans-isomer 26-4-2 (0.200 g, 37.0%). Cis isomer: $^1$H NMR (CDCl$_3$, 400 MHz) δ 7.48 (4H, m), 7.30 (5H, m), 7.05 (2H, m), 6.70 (1H, m), 6.40 (1H, s), 4.20 (1H, m), 3.78 (2H, s), 2.90 (4H, m), 1.90 (4H, m), 1.55 (4H, m). MS m/e 450 (M+H). Trans-isomer: $^1$H NMR (CDCl$_3$, 400 MHz) δ 7.48 (4H, m), 7.33 (5H, m), 7.05 (2H, m), 6.70 (1H, m), 6.37 (1H s), 4.20 (1H, m), 3.82 (2H, s), 2.88 (3H, m), 2.50 (1H, m), 2.10 (2H, m), 1.80 (2H, m), 1.20–1.70 (4H, m). MS m/e 450 (M+H).

Step 5

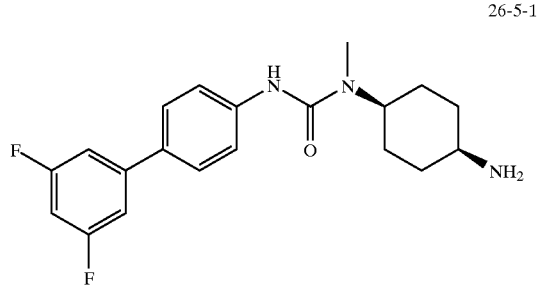

26-5-1

To the cis isomer 26-4-1 (0.600 g, 1.33 mmol) in 4.4% HCOOH/CH$_3$OH (50 ml) was added 10% Pd/C (0.600 g). The reaction mixture was stirred at R.T. under argon for 16 h, then filtered through celite and concentrated. The residue was purified by PTLC (1:10 (2M NH$_3$/CH$_3$OH)/CH$_2$Cl$_2$) to afford the product (0.230 g, 85%). $^1$H NMR (CDCl$_3$, 400 MHz) δ 7.50 (4H, s), 7.06 (2H, m), 6.70 (1H, m), 6.40 (1H, s), 4.20 (1H, m), 3.30 (1H), 3.00 (3H, s), 1.50–2.30 (10H, m). MS m/e 360 (M+H).

Step 6

To a mixture of the product of Step 5 (0.140 g, 0.390 mmol) and 1 M K$_2$CO$_3$ (1.2 ml, 1.2 mmol) in THF (5 ml) was added MeSO$_2$Cl (0.178 g, 1.55 mmol). The reaction mixture was stirred at R.T. for 16 h then subjected to PTLC (1:10 CH$_3$OH/CH$_2$Cl$_2$) to give the product (0.135 g, 79%). $^1$H NMR (CDCl$_3$, 400 MHz) δ 7.53 (4H, m), 7.20 (2H, m), 6.90 (1H, m), 4.10 (1H, m), 3.60 (1H, m), 2.90 (6H, s), 1.50–2.10 (8H, m). MS m/e 438 (M+H).

EXAMPLE 27

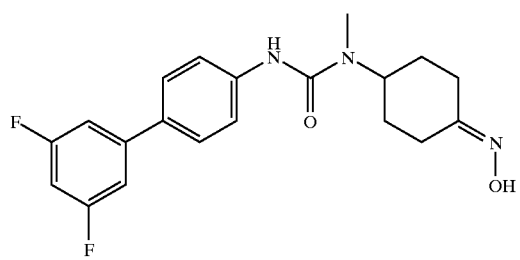

27

A mixture of 26-3-1 (0.21 g, 0.59 mmol), hydroxylamine hydrochloride (0.82 g, 12 mmol), and sodium acetate (0.97 g, 12 mmol) in absolute EtOH (10 ml) was stirred at R.T. for 64 h. The mixture was partitioned between CH$_2$Cl$_2$ (100 ml) and water (75 ml). The aqueous layer was extracted again with CH$_2$Cl$_2$ (50 ml). The combined organic layers were dried (Na$_2$SO$_4$), filtered and concentrated. The residue was subjected to PTLC (1:19 CH$_3$OH/CH$_2$Cl$_2$) to give the product (210 mg, 95%). $^1$H NMR (CD$_3$OD, 400 MHz) δ 7.4–7.6 (4H, m), 7.20 (2H, m), 6.85 (1H, m), 4.39 (1H, m), 3.45 (1H, m), 2.90 (3H, s), 2.45 (1H, m), 2.28 (1H, m), 1.6–2.0 (5H, m). MS (ES) m/e 374 (M+H).

Use of the appropriate starting material and essentially the same procedure afforded the following compound.

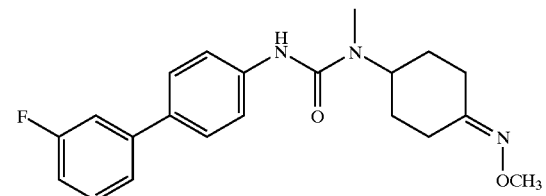

27A

MS (ES) m/e 388 (M+H).

EXAMPLE 28

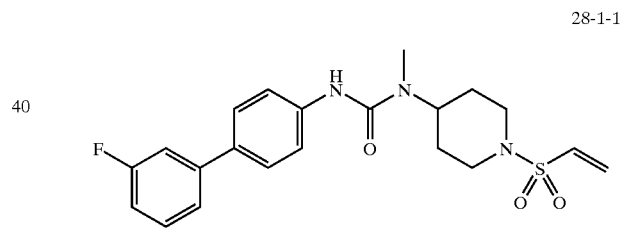

28

Step 1

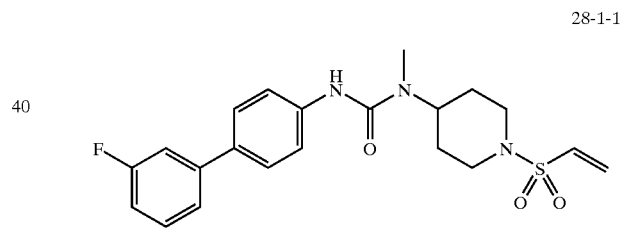

28-1-1

To a mixture of 1-3-5 (100 mg, 0.31 mmol), 1 M NaOH (0.5 ml), and 1 M Na$_2$CO$_3$ (0.5 ml) in CH$_2$Cl$_2$ (5 ml) was added 2-chloroethylsulfonyl chloride (100 mg, 0.61 mmol), and the reaction mixture was stirred for 16 hr. The reaction mixture was partitioned between water (25 ml) and CH$_2$Cl$_2$ (25 ml). The organic layer was dried (MgSO$_4$), filtered, and concentrated. Subjection of the residue to PTLC (1:4 acetone/CH$_2$Cl$_2$) gave the product (40 mg, 31%). MS (ES) m/e 418 (M+H).

Step 2

To a stirred solution of the product of Step 1 (28-1-1) (50 mg, 0.12 mmol) in THF (10 ml) was added tetrabutylammonium hydroxide (0.5 g) in water (2 ml). After 16 hr, the reaction mixture was partitioned between water (25 ml) and CH$_2$Cl$_2$ (100 ml). The organic layer was dried (MgSO$_4$), filtered, and concentrated. Subjection of the residue to PTLC (5:95 MeOH/CH$_2$Cl$_2$) gave the product (24 mg, 46%). HRMS calc. for C$_{21}$H$_{27}$FN$_3$O$_4$S (M+H) 436.1706. Found 436.1711.

EXAMPLE 29

To a solution of 1-3-1 (400 mg, 1.22 mmol) in DMF (5 ml) was added EDCI (25 mg, 1.30 mmol) and 1-cyano-3-methylisothiourea sodium salt (175 mg, 1.27 mmol). The reaction mixture was stirred for 16 h, then diluted with EtOAc (50 ml). The mixture was washed with water (10 ml), sat'd NaHCO$_3$ (20 ml) and water (10 ml). The organic layer was dried (MgSO$_4$), filtered and concentrated. Subjection of the residue to flash chromatography (gradient; 3:97–7:93 MeOH/CH$_2$Cl$_2$) gave the product (250 mg, 50%). HRMS calc. For C$_{22}$H$_{26}$N$_6$OF (M+H) 409.2152. Found 409.2155.

EXAMPLE 30

To a solution of 1-3-1 (500 mg, 1.53 mmol) in acetonitrile (10 ml) was added dimethyl-N-cyanodithioiminocarbonate (0.8 g, 5.5 mmol) and the reaction mixture was refluxed for 16 h. The reaction mixture was poured into water (50 ml) and extracted with EtOAc (50 ml). The organic layer was dried (MgSO$_4$), filtered and concentrated. Subjection of the residue to flash chromatography (1:2 acetone/hexanes) gave the product (150 mg, 24%). MS m/e 426.1 (M+H).

Method for Screening Compound 14 of Example 14 for Y5 Antagonist Activity In Vivo Adult male Long-Evans or Sprague-Dawley rats (200–250 g, Charles River, Mass.) were maintained in individual cages at 22° C. on a 12 hr light/12 hr dark cycle with lights on at 0400. Rats had free access to food (Teklad Lab Rodent Chow, Bartonville, Ill.) and water. All studies were conducted in an AAALAC accredited facility following protocols approved by the Animal Care and Use Committee of the Schering-Plough Research Institute. The procedures were performed in accordance with the principles and guidelines established by the NIH for the care and use of laboratory animals.

Rats were anesthetized by intramuscular injection of a mixture of ketamine and xylazine (100 and 10 mg/kg, respectively). A 22 gauge stainless steel cannula was stereotaxically implanted into the lateral ventricle using the following coordinates: 1 mm posterior to bregma, 1.5 mm lateral to midline, 3.6 mm ventral to dura. After a three week recovery period, all animals were tested for correct cannula placement by intracerebroventricular (icv) infusion of human NPY (0.3 mmol). Only animals demonstrating a profound feeding effect (>2 g) within 60 min of the infusion were retained for the study. Four groups of twelve animals were used in each study. Each group was balanced such that the average baseline and NPY-induced food intake values were similar for each group. One group received an oral dose of vehicle while the other three groups received oral doses of the Y5 antagonist 14 one hour before icv administration of D-Trp34-NPY. D-Trp34-NPY was dissolved in 0.9% sterile saline (Sigma, St. Louis, Mo.) and were infused icv with a Hamilton infusion pump and syringe (Hamilton, Reno, Nev.) at a rate of 5 µl/min. The guide cannula remained inserted for an additional minute to prevent diffusion up the needle track. The chow-filled feeder was weighed during the infusion period and then returned to the home cage with the animal immediately following treatment. Food consumption was monitored at 60, 120 and 240 min after icv infusion of peptides. Differences in food intake between groups were determined by analysis of variance followed by Dunnett's multiple comparison test. Compound 14 (0.1, 0.3, 1, and 3 mg/kg) dose responsively inhibited D-Trp34-NPY stimulated food intake with an ID50 of 0.5 mg/kg.

It will be recognized that the following examples can be prepared by adapting appropriate procedures described in Examples 1–30, or by applying methods known to those skilled in the art:

| Example | Structure | MSm/e (M + H) |
|---|---|---|
| 31 | 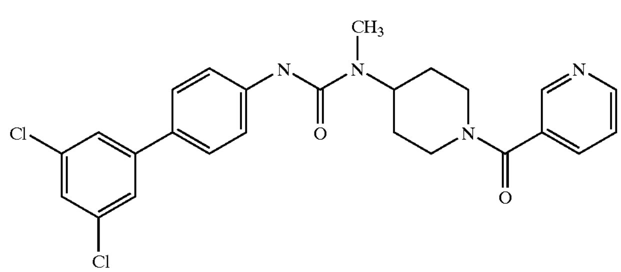 | 483 |

-continued

| Example | Structure | MSm/e (M + H) |
|---|---|---|
| 32 | 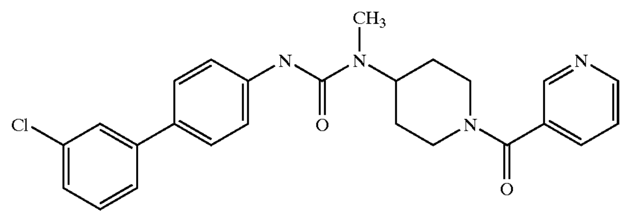 | 449 |
| 33 | 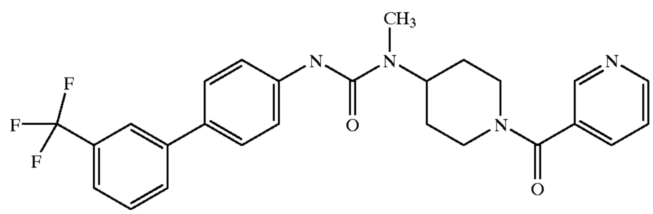 | 483 |
| 34 | 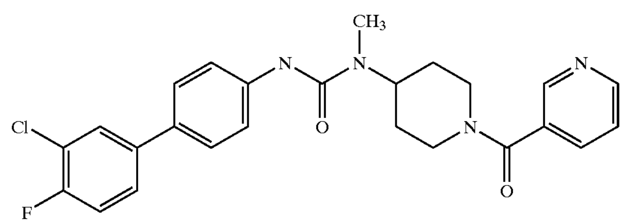 | 467 |
| 35 | 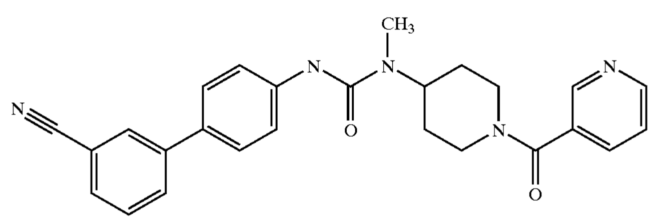 | 440 |
| 36 | 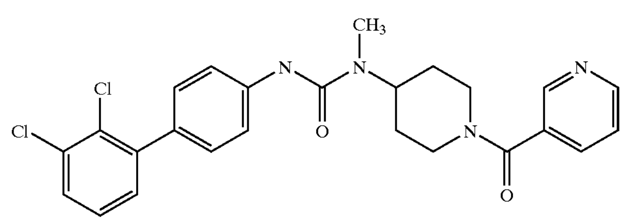 | 483 |
| 37 | 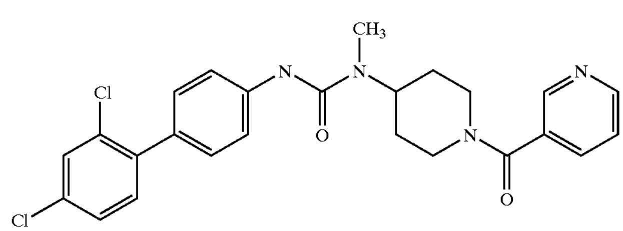 | 483 |

-continued

| Example | Structure | MSm/e (M + H) |
|---|---|---|
| 38 | 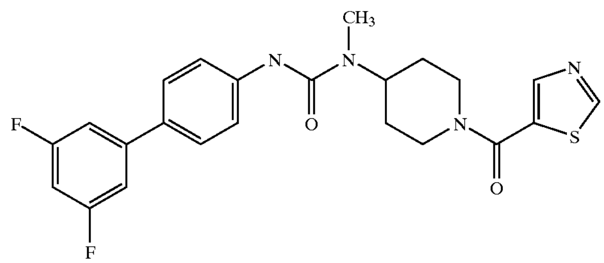 | 457 |
| 39 | 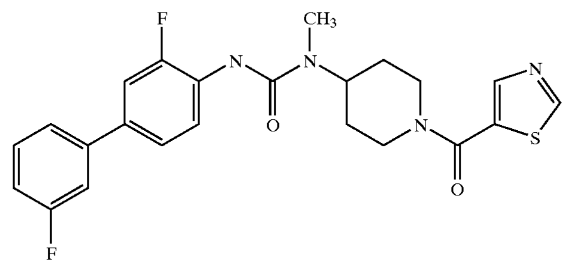 | 457 |
| 40 | 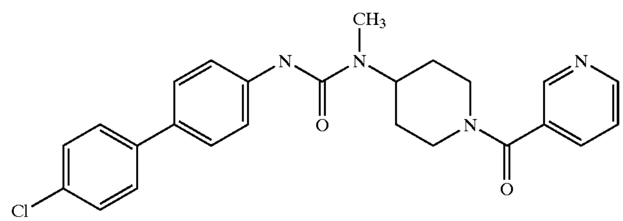 | 449 |
| 41 | 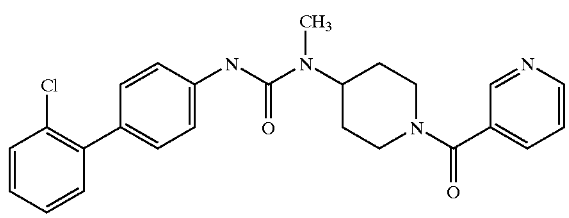 | 449 |
| 42 | 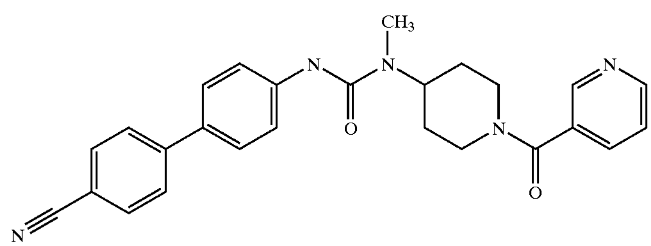 | 440 |
| 43 | 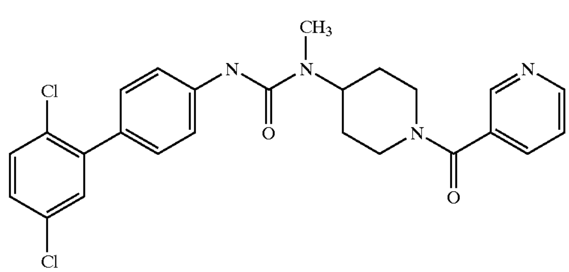 | 483 |

| Example | Structure | MSm/e (M + H) |
|---|---|---|
| 44 | 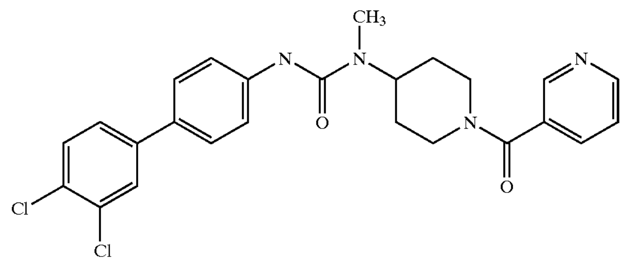 | 483 |
| 45 | 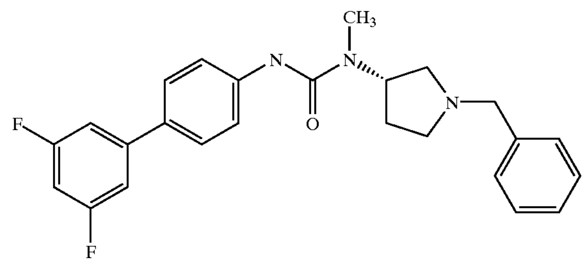 | 422 |
| 46 | 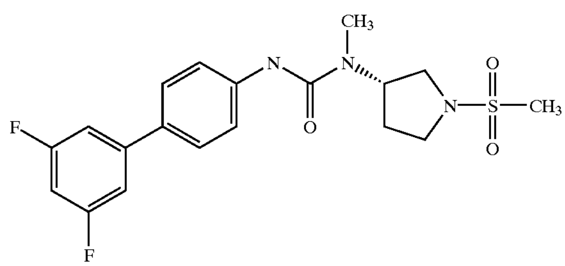 | 410 |
| 47 | 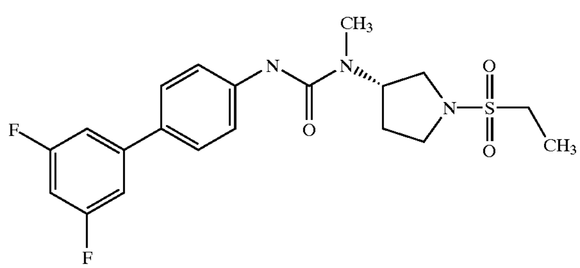 | 424 |
| 48 | 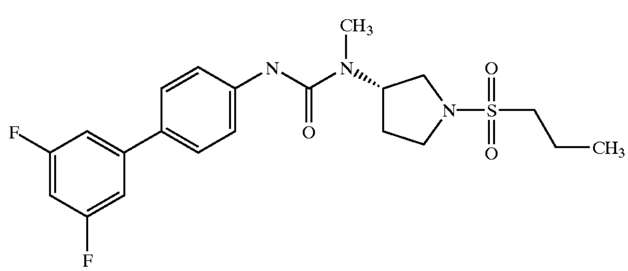 | 438 |

-continued

| Example | Structure | MSm/e (M + H) |
|---|---|---|
| 49 | 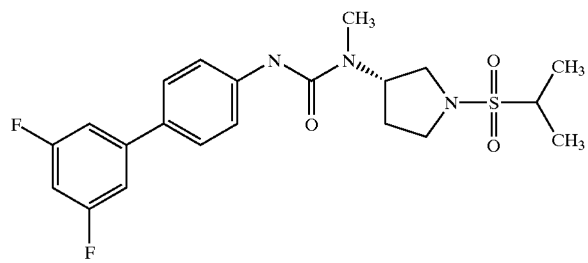 | 438 |
| 50 | 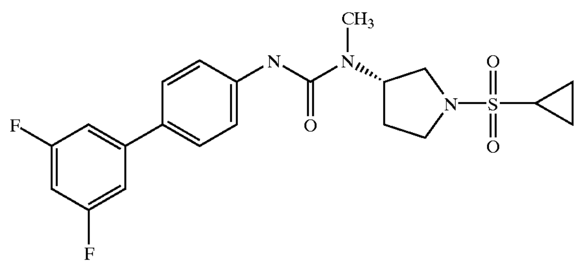 | 436 |
| 51 | 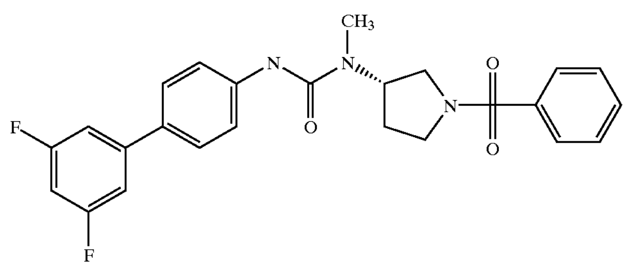 | 472 |
| 52 | 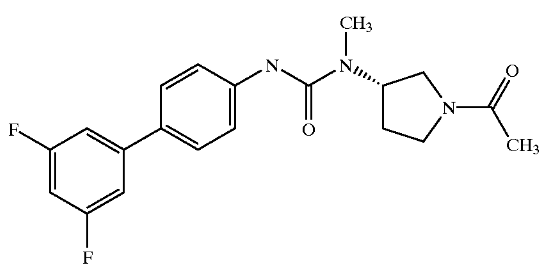 | 374 |
| 53 | 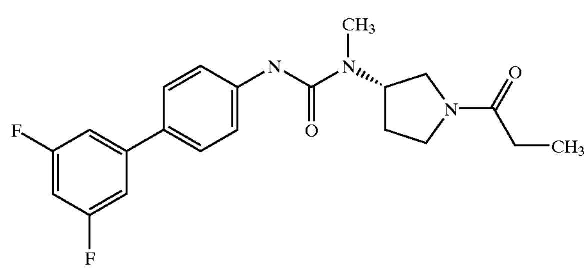 | 388 |

-continued

| Example | Structure | MSm/e (M + H) |
|---|---|---|
| 54 | 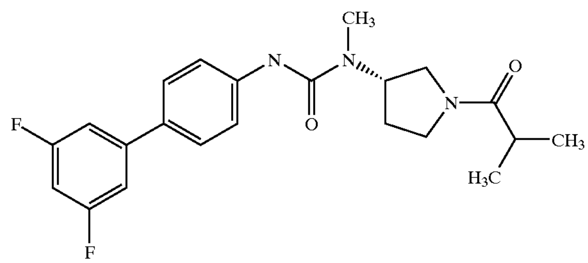 | 402 |
| 55 | 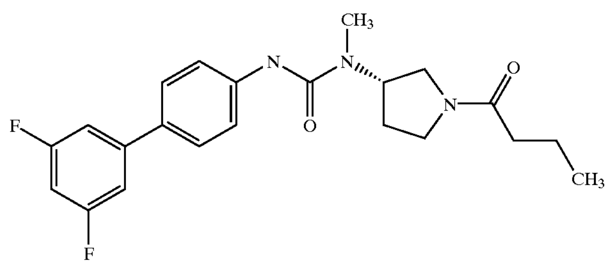 | 402 |
| 56 | 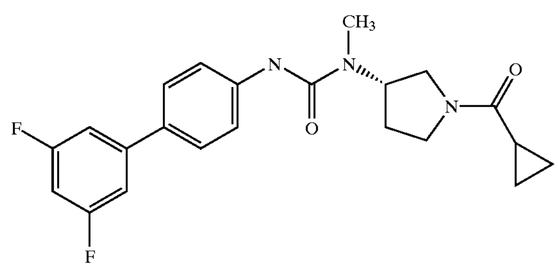 | 400 |
| 57 | 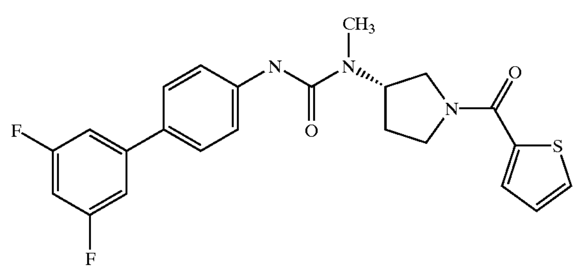 | 442 |
| 58 | 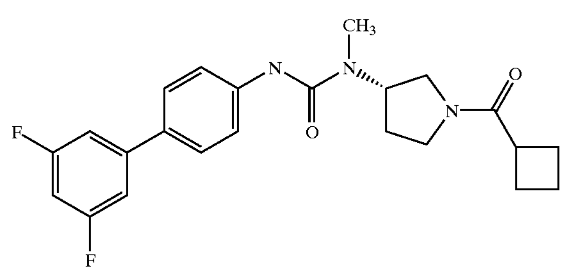 | 414 |

-continued

| Example | Structure | MSm/e (M + H) |
|---|---|---|
| 59 | 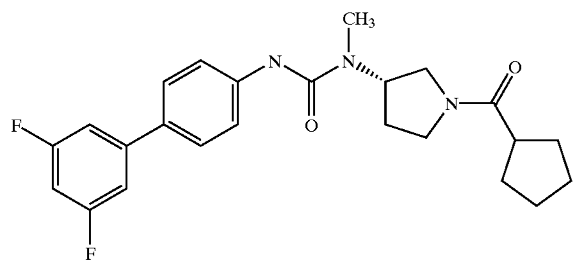 | 428 |
| 60 | 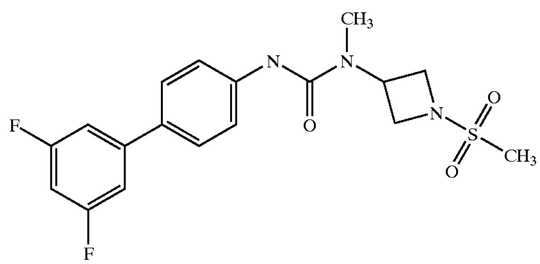 | 396 |
| 61 | 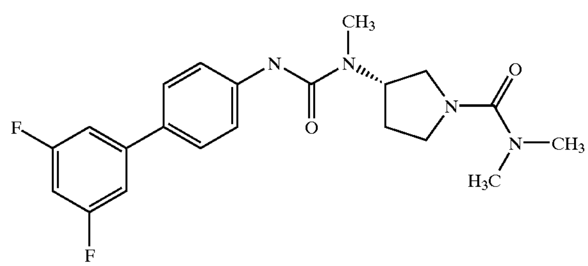 | 403 |
| 62 | 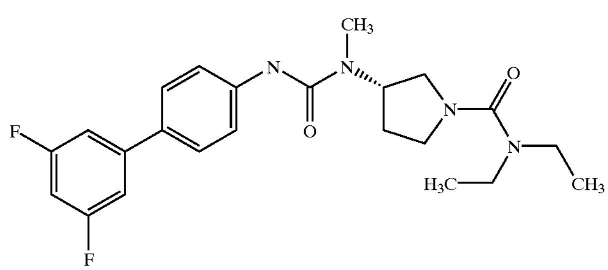 | 431 |
| 63 | 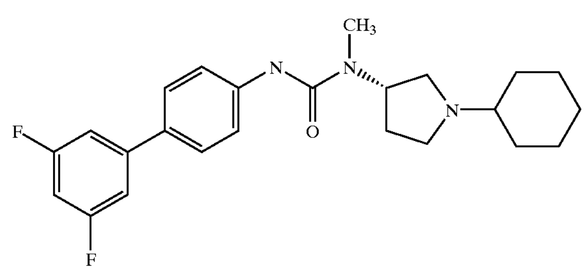 | 414 |

-continued

| Example | Structure | MSm/e (M + H) |
|---------|-----------|---------------|
| 64 | 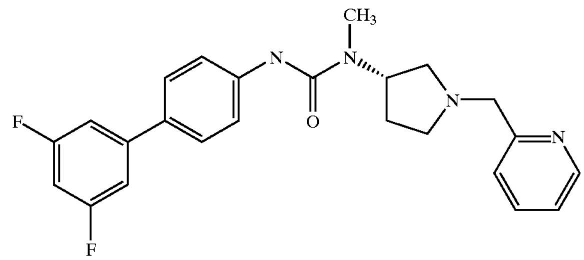 | 423 |
| 65 | 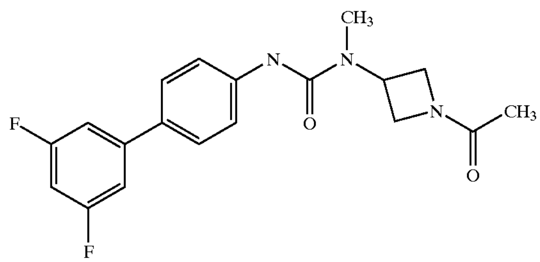 | 360 |
| 66 | 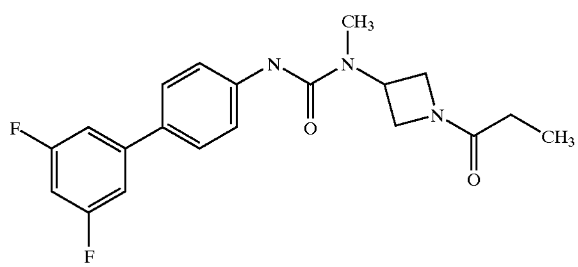 | 374 |
| 67 | 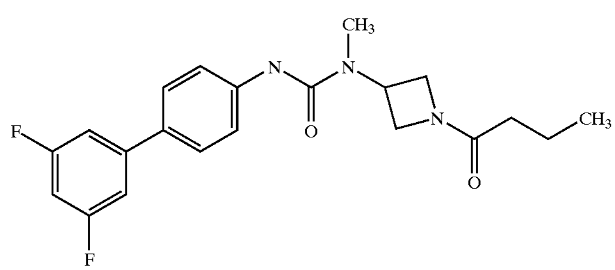 | 388 |
| 68 | 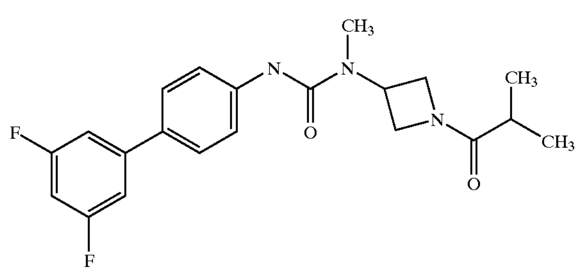 | 388 |

-continued

| Example | Structure | MSm/e (M + H) |
|---|---|---|
| 69 | 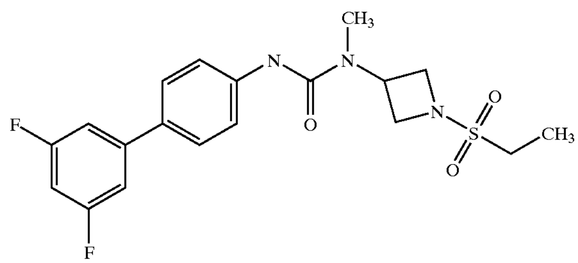 | 410 |
| 70 | 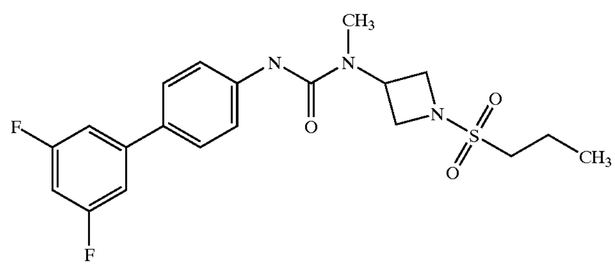 | 424 |
| 71 | 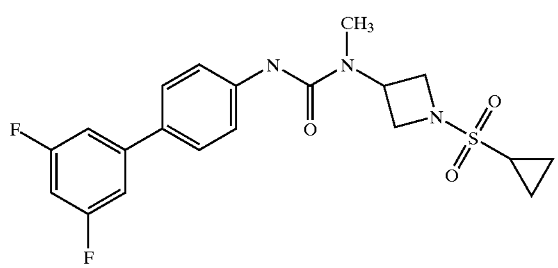 | 422 |
| 72 | 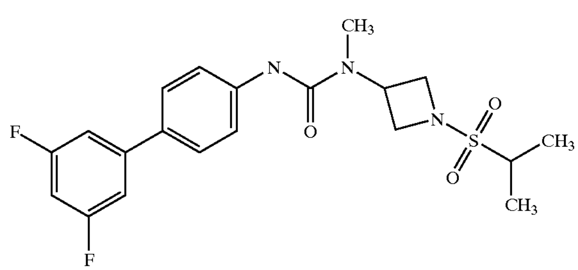 | 424 |
| 73 | 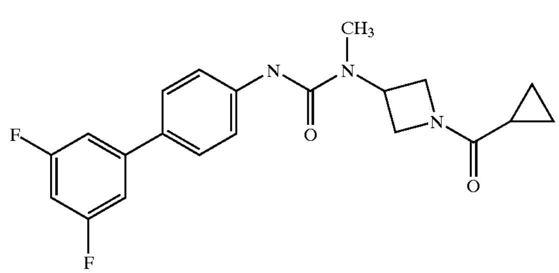 | 386 |

-continued

| Example | Structure | MSm/e (M + H) |
|---------|-----------|---------------|
| 74 | 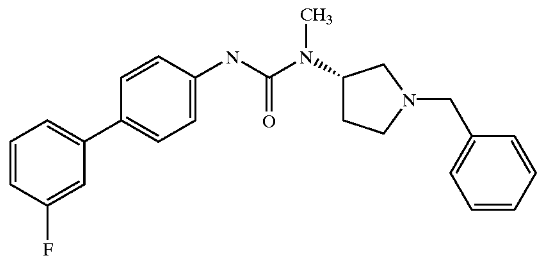 | 404 |
| 75 | 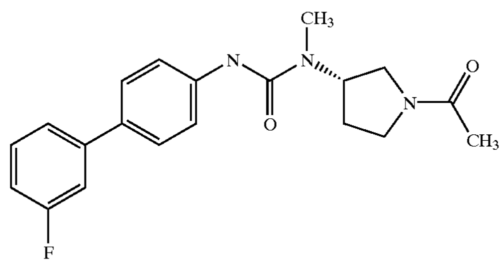 | 356 |
| 76 | 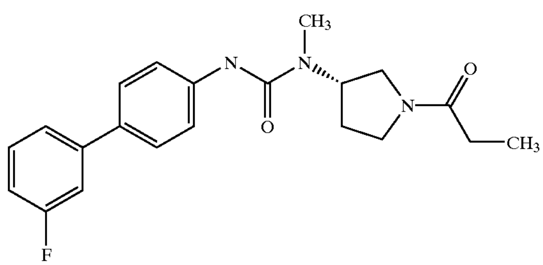 | 370 |
| 77 | 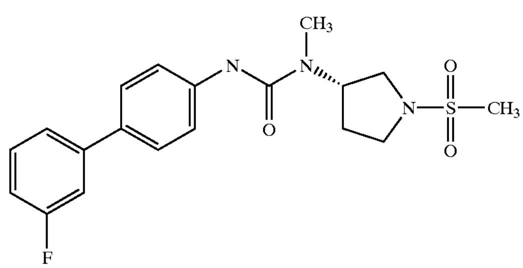 | 392 |
| 78 | 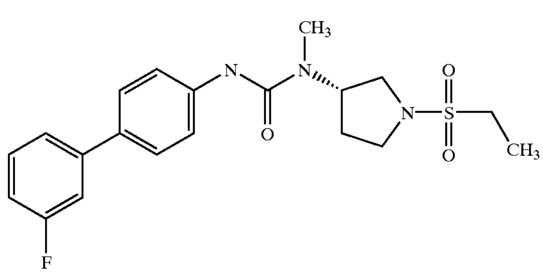 | 406 |

| Example | Structure | MSm/e (M + H) |
|---|---|---|
| 79 | 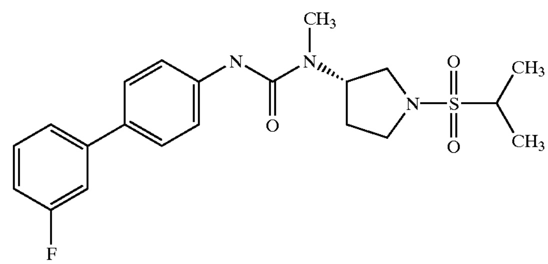 | 420 |
| 80 | 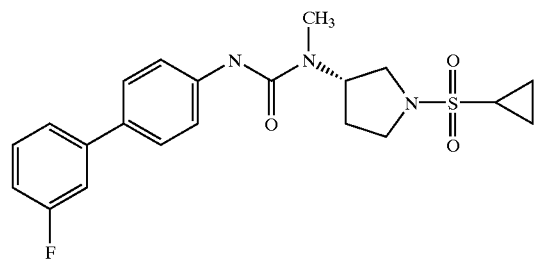 | 418 |
| 81 | 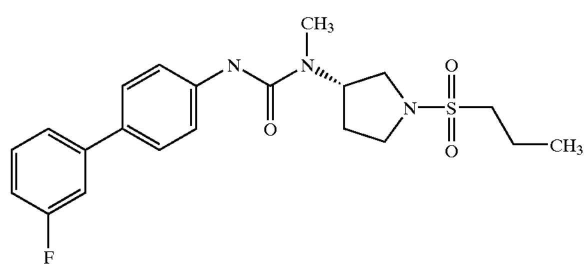 | 420 |
| 82 | 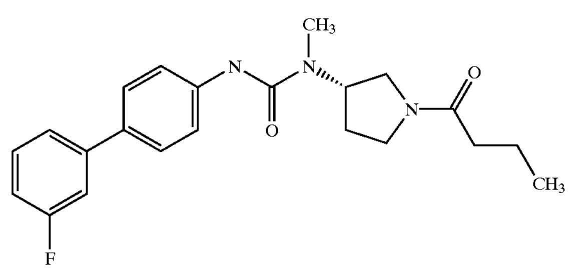 | 384 |
| 83 | 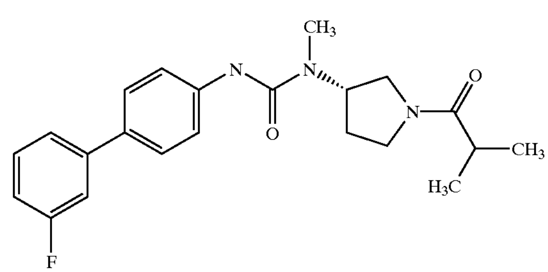 | 384 |

US 6,894,063 B2
79                                                                                       80
-continued
| Example | Structure | MSm/e (M + H) |
|---------|-----------|---------------|
| 84 | 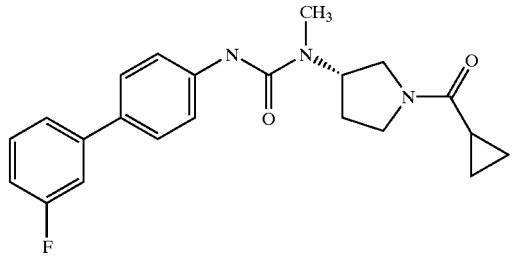 | 382 |
| 85 | 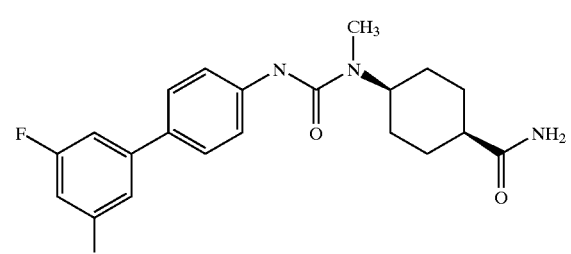 | 388 |
| 86 | 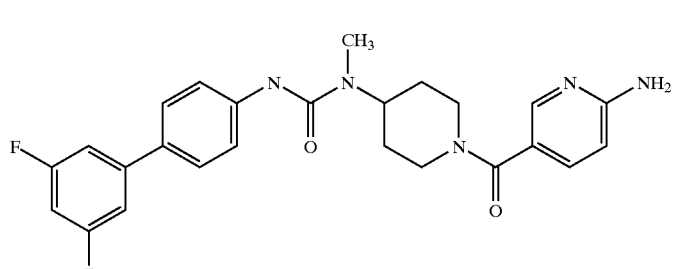 | 466 |
| 87 | 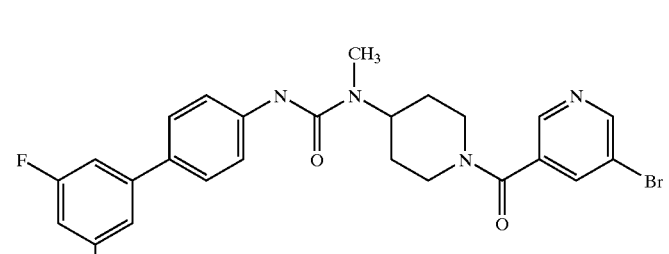 | 531 |
| 88 | 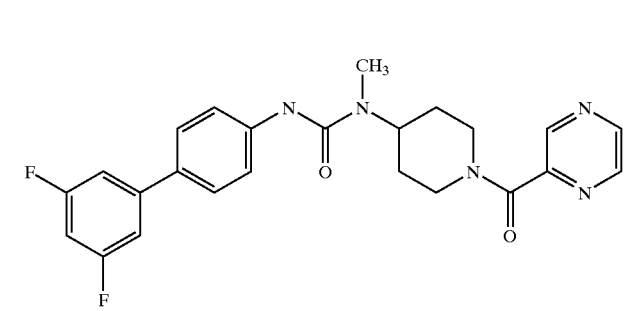 | 452 |

-continued
| Example | Structure | MSm/e (M + H) |
|---|---|---|
| 89 | 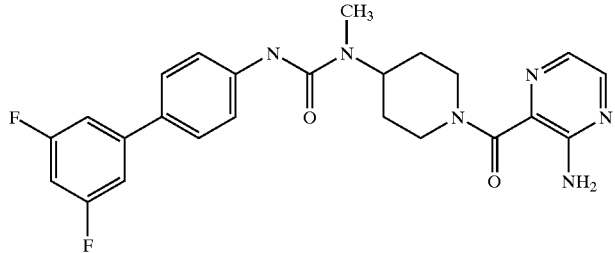 | 467 |
| 90 | 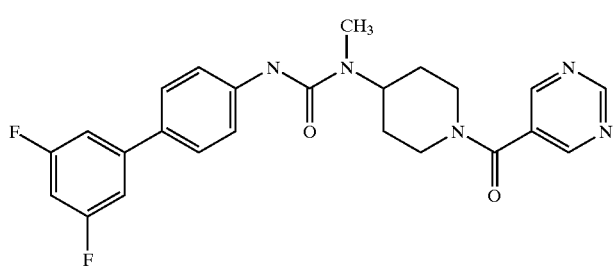 | 452 |
| 91 | 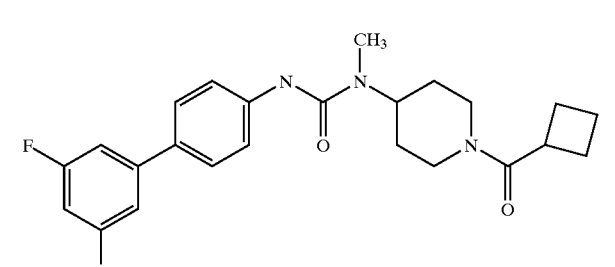 | 428 |
| 92 | 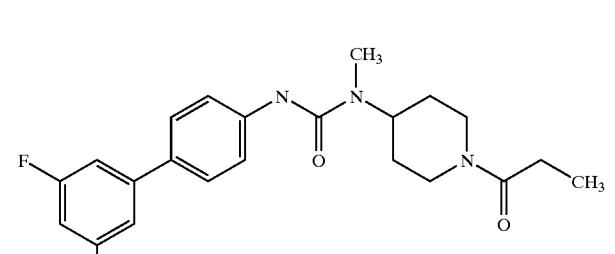 | 402 |
| 93 | 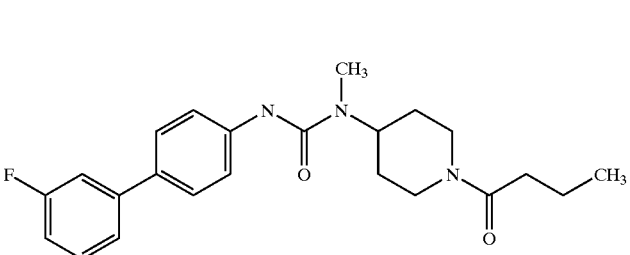 | 416 |

-continued

| Example | Structure | MSm/e (M + H) |
|---|---|---|
| 94 | 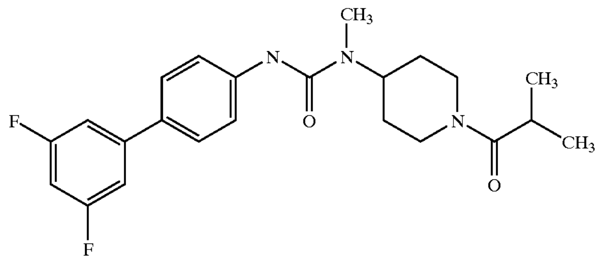 | 416 |
| 95 | 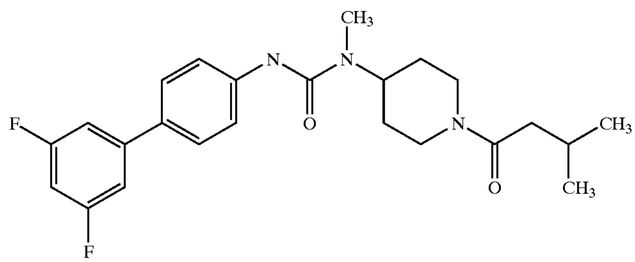 | 430 |
| 96 | 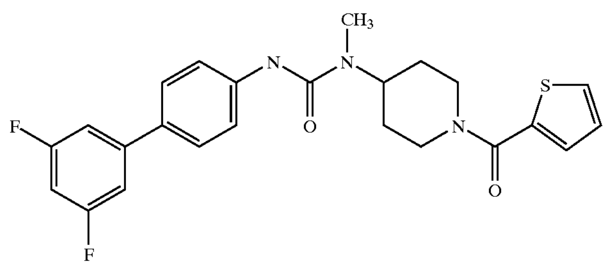 | 456 |
| 97 | 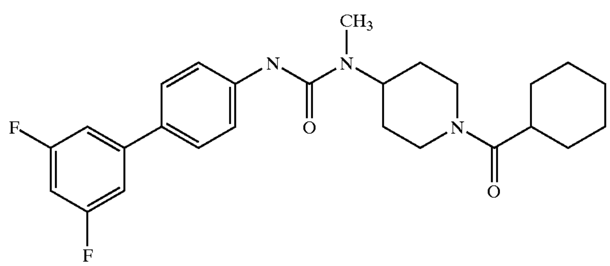 | 456 |
| 98 | 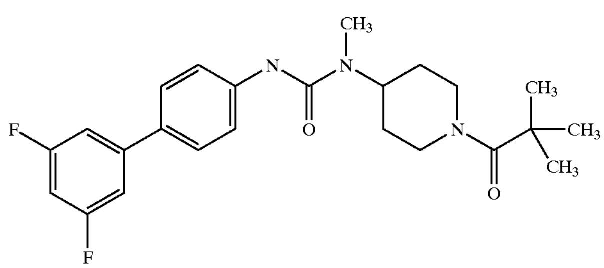 | 430 |

-continued
| Example | Structure | MSm/e (M + H) |
|---|---|---|
| 99 | 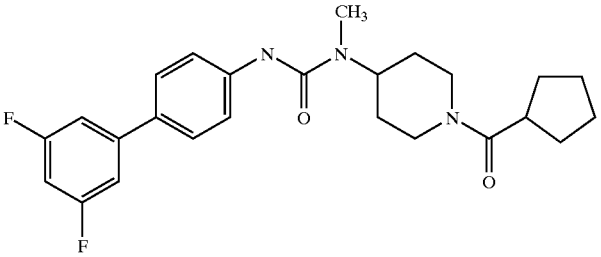 | 442 |
| 100 | 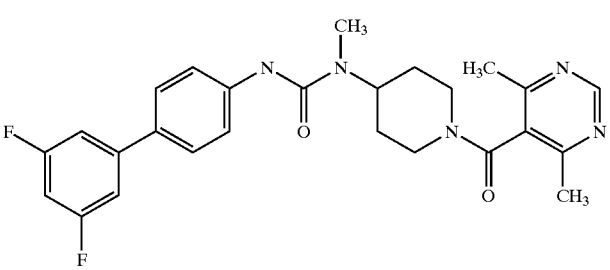 | 480 |
| 101 | 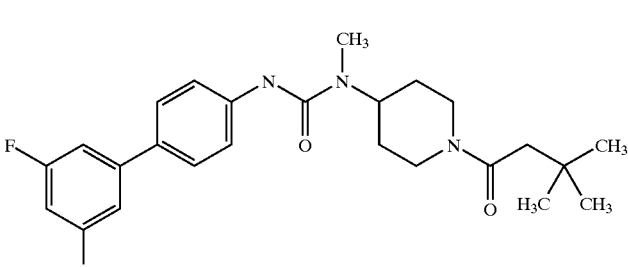 | 444 |
| 102 | 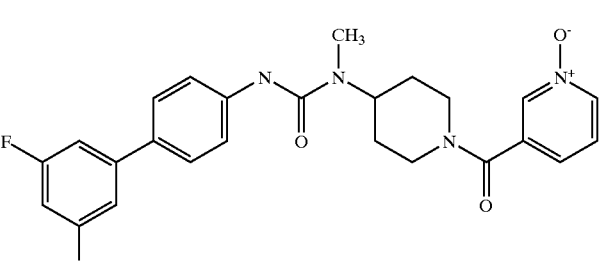 | 467 |
| 103 | 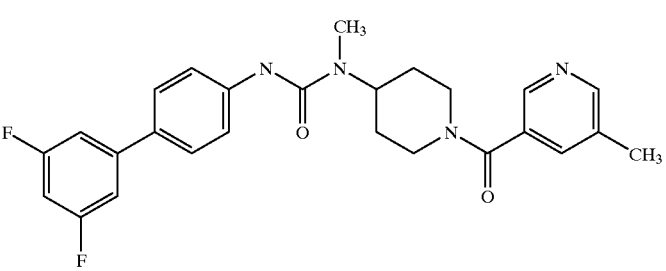 | 465 |

-continued

| Example | Structure | MSm/e (M + H) |
|---|---|---|
| 104 | 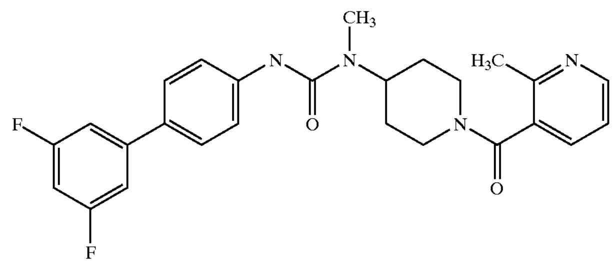 | 465 |
| 105 | 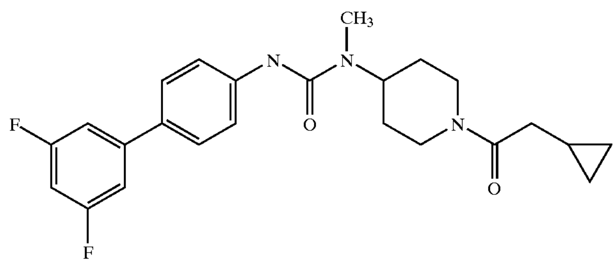 | 428 |
| 106 | 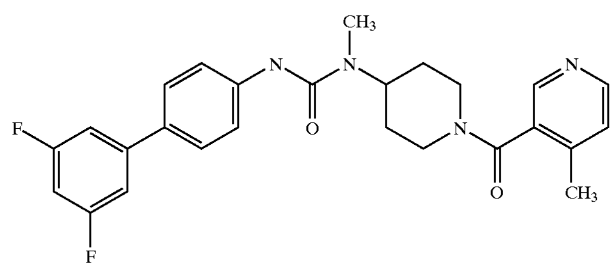 | 465 |
| 107 | 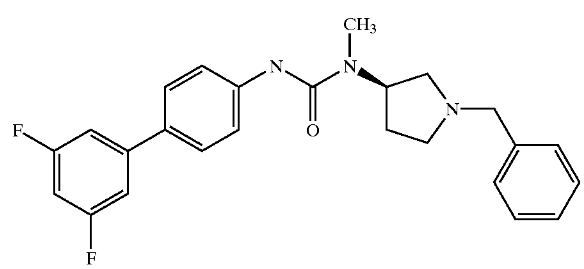 | 422 |
| 108 | 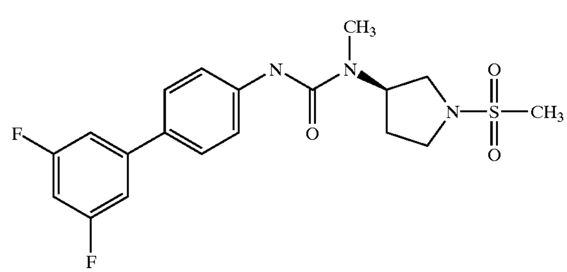 | 410 |

-continued

| Example | Structure | MSm/e (M + H) |
|---------|-----------|---------------|
| 109 | 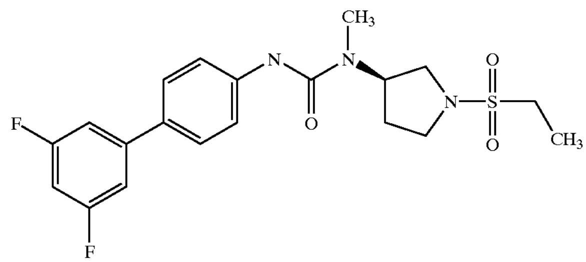 | 424 |
| 110 | 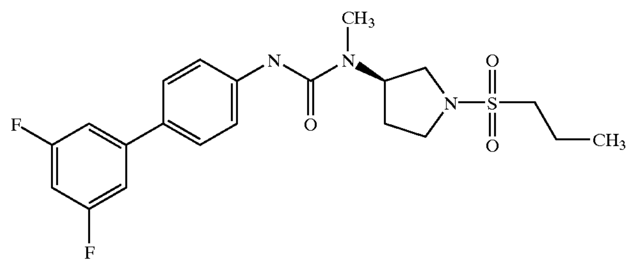 | 438 |
| 111 | 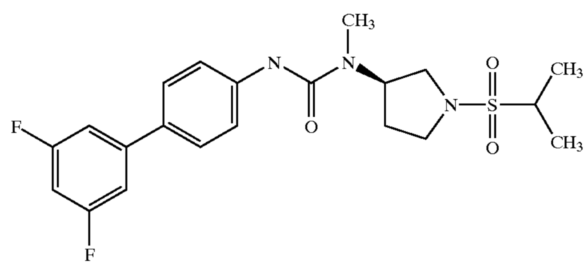 | 438 |
| 112 | 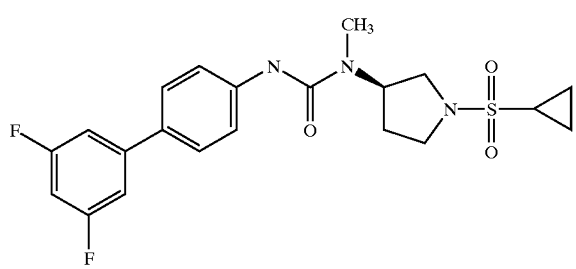 | 436 |
| 113 | 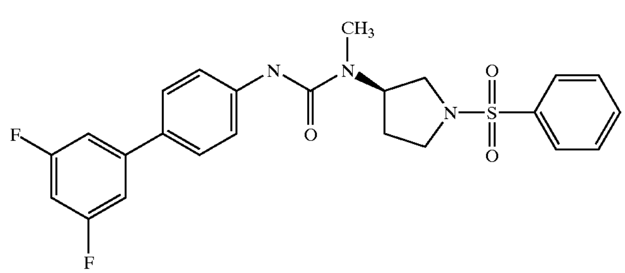 | 472 |

| Example | Structure | MSm/e (M + H) |
|---|---|---|
| 114 | 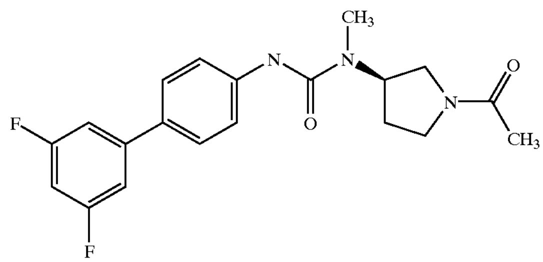 | 374 |
| 115 | 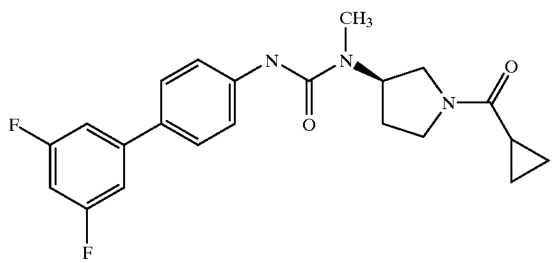 | 400 |
| 116 | 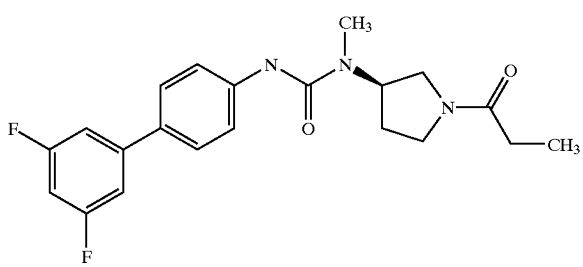 | 388 |
| 117 | 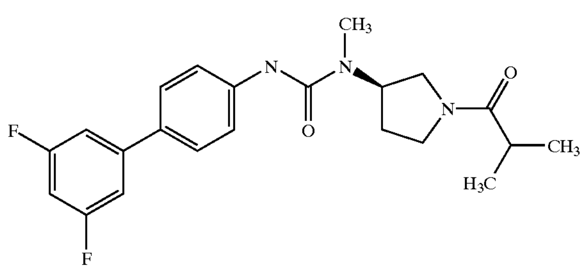 | 402 |
| 118 | 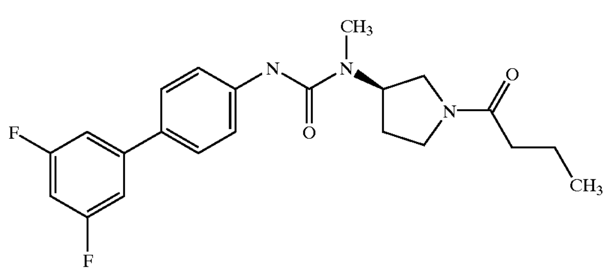 | 402 |

-continued

| Example | Structure | MSm/e (M + H) |
|---|---|---|
| 119 | 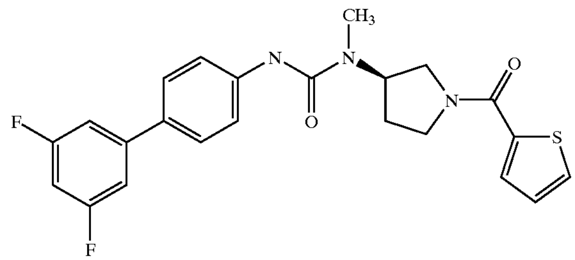 | 442 |
| 120 | 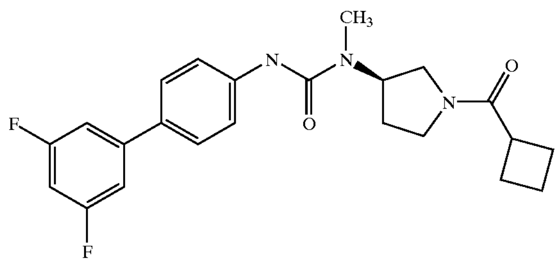 | 414 |
| 121 | 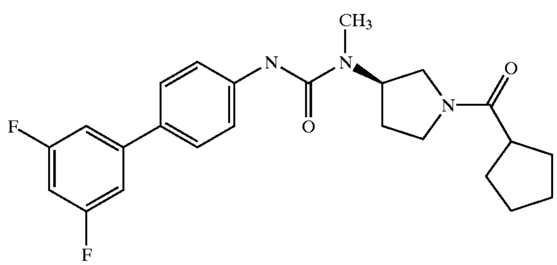 | 428 |
| 122 | 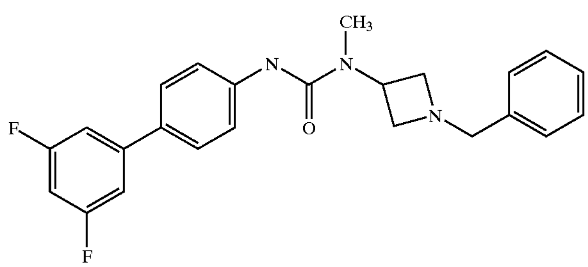 | 408 |
| 123 | 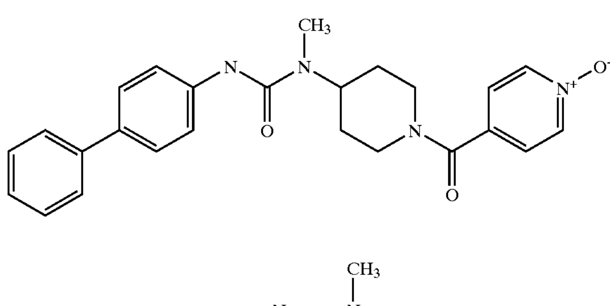 | 431 |
| 124 | 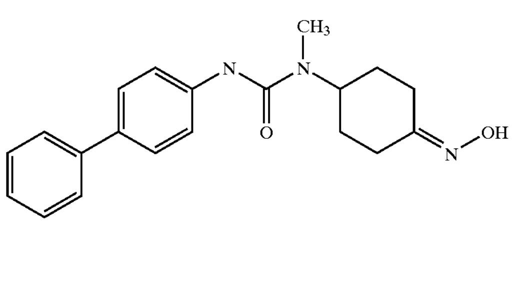 | 338 |

-continued

| Example | Structure | MSm/e (M + H) |
|---|---|---|
| 125 | 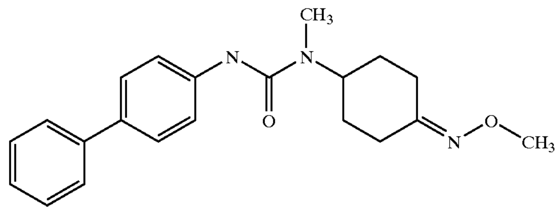 | 352 |
| 126 | 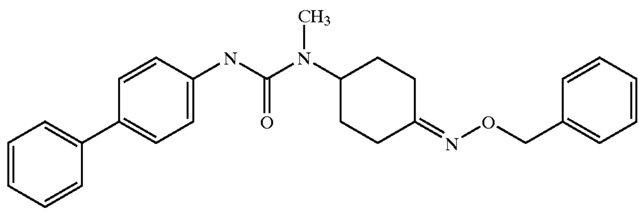 | 428 |
| 127 | 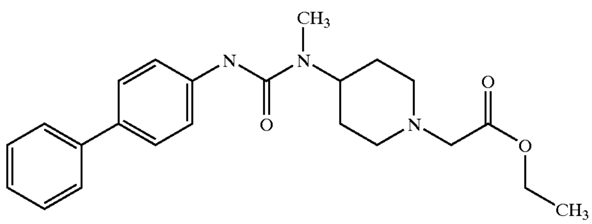 | 396 |
| 128 | 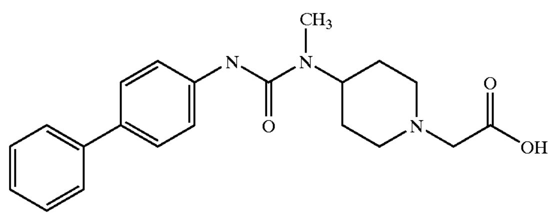 | 368 |
| 129 | 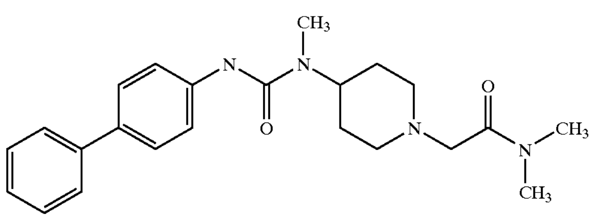 | 395 |
| 130 | 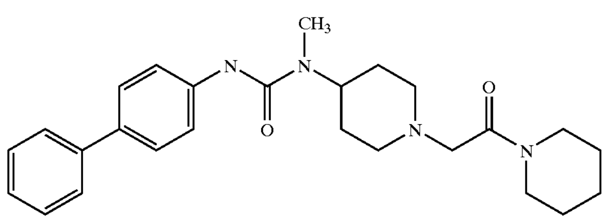 | 435 |
| 131 | 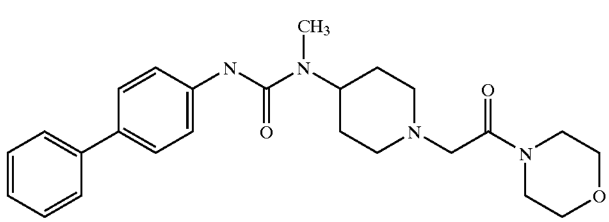 | 437 |

-continued

| Example | Structure | MSm/e (M + H) |
|---|---|---|
| 132 | 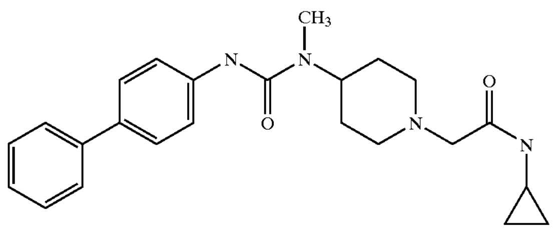 | 407 |
| 133 | 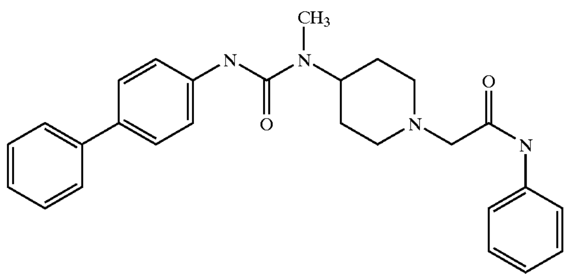 | 443 |
| 134 | 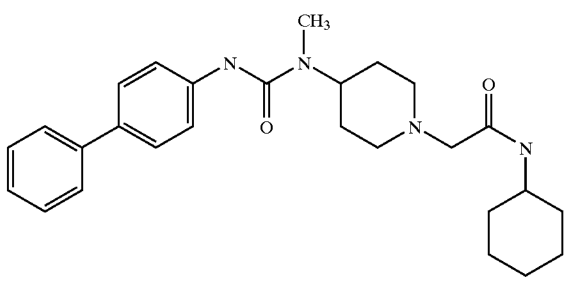 | 449 |
| 135 | 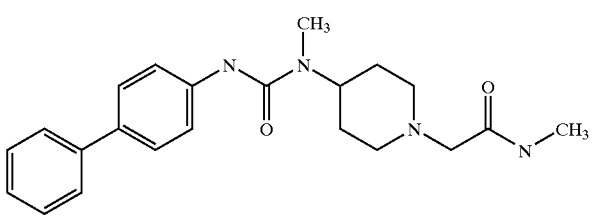 | 381 |
| 136 | 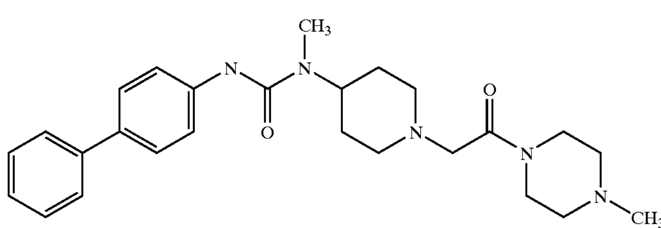 | 450 |
| 137 | 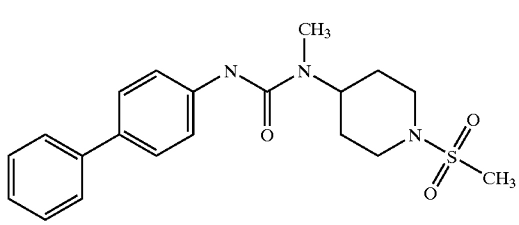 | 388 |

-continued

| Example | Structure | MSm/e (M + H) |
| --- | --- | --- |
| 138 | 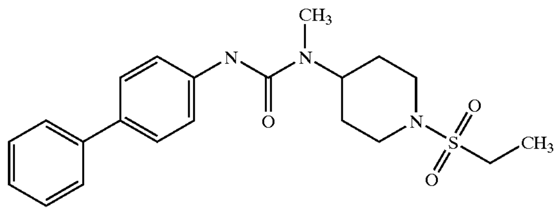 | 402 |
| 139 | 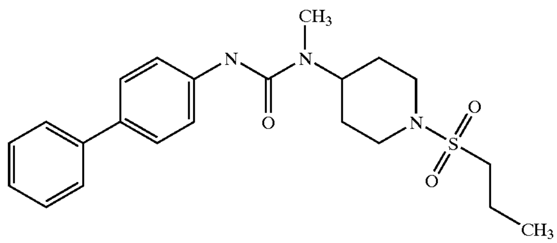 | 416 |
| 140 | 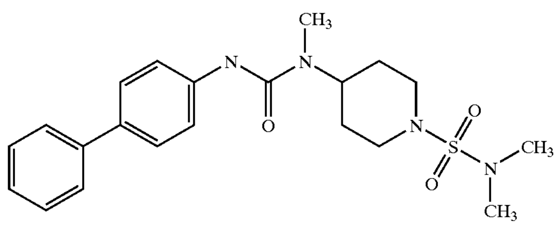 | 417 |
| 141 | 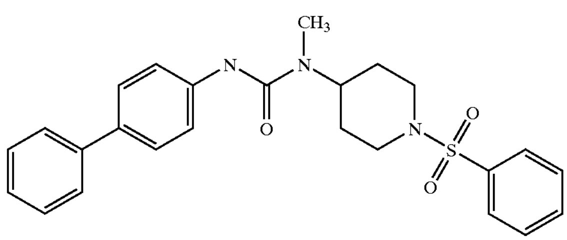 | 450 |
| 142 | 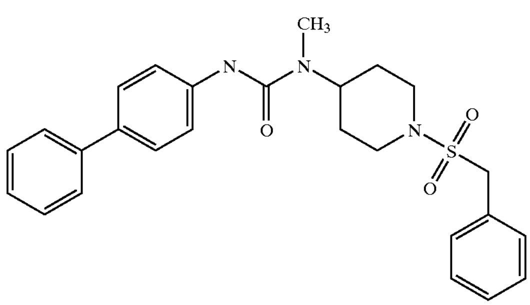 | 464 |
| 143 | 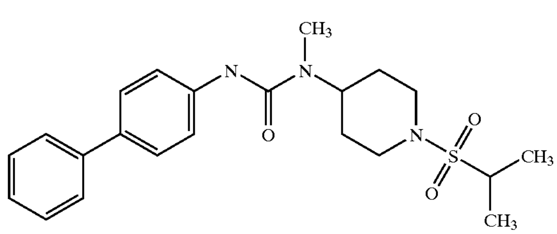 | 416 |

-continued

| Example | Structure | MSm/e (M + H) |
|---|---|---|
| 144 | 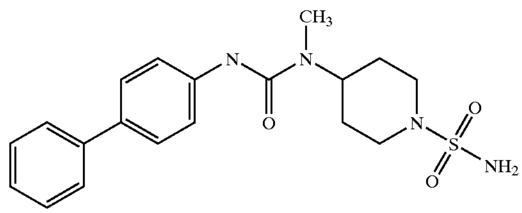 | 389 |
| 145 | 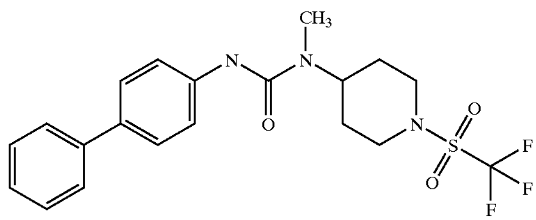 | 442 |
| 146 | 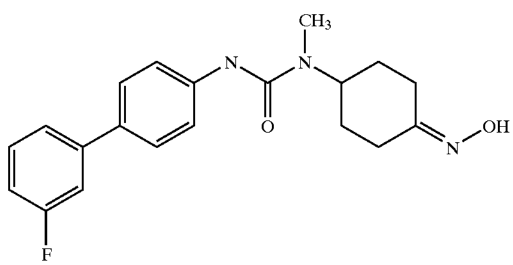 | 356 |
| 147 | 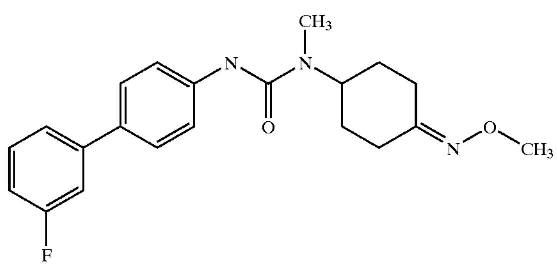 | 370 |
| 148 | 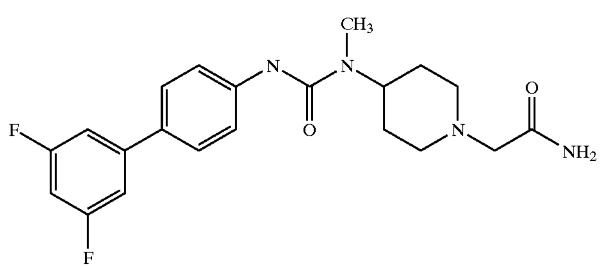 | 403 |
| 149 | 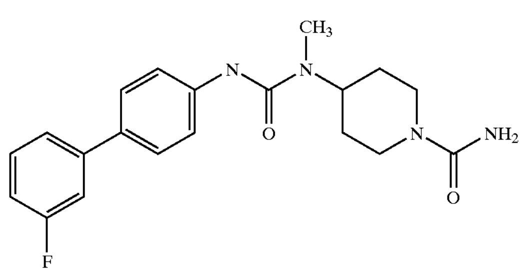 | 371 |

-continued

| Example | Structure | MSm/e (M + H) |
|---------|-----------|---------------|
| 150 | 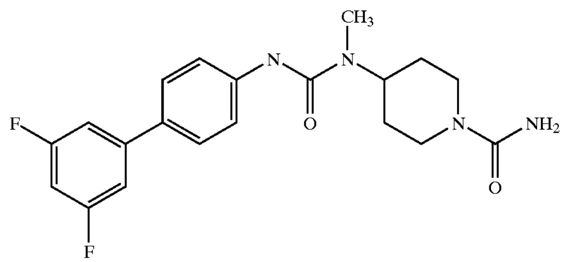 | 389 |
| 151 | 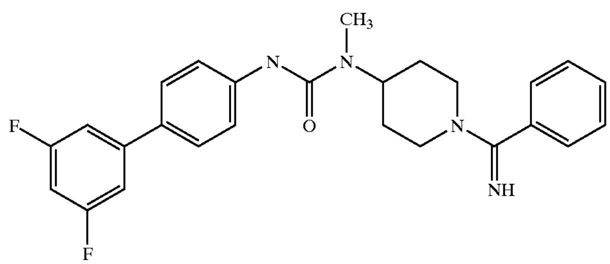 | 449 |
| 152 | 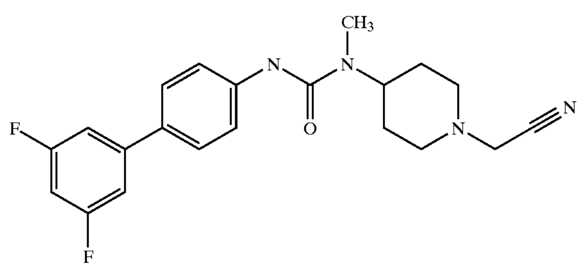 | 385 |
| 153 | 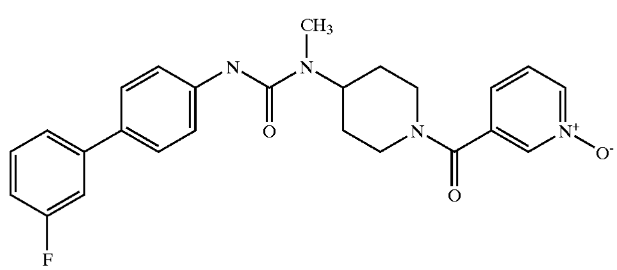 | 449 |
| 154 | 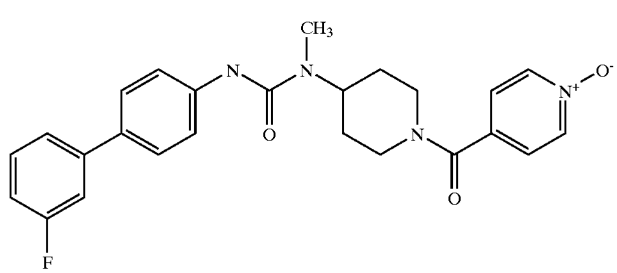 | 449 |

-continued
| Example | Structure | MSm/e (M + H) |
|---|---|---|
| 155 | 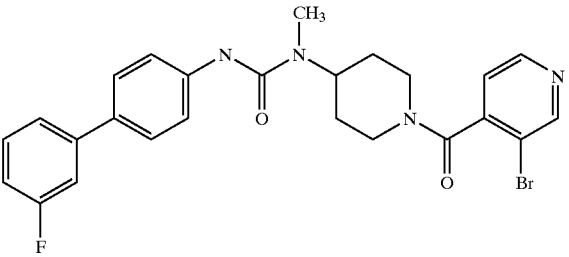 | 511 |
| 156 | 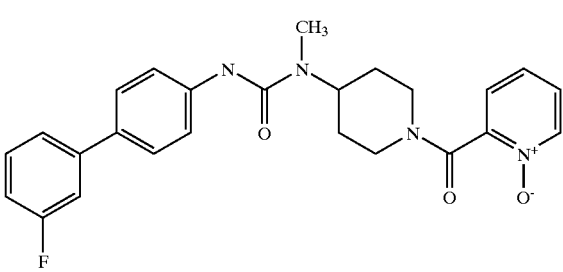 | 449 |
| 157 | 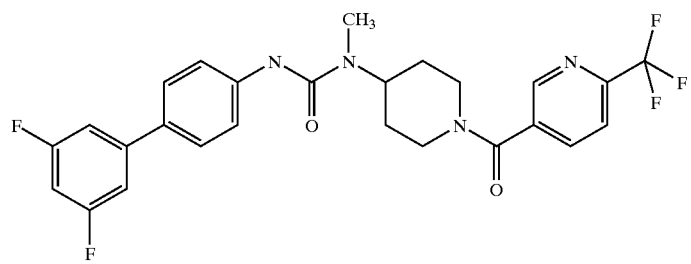 | 519 |
| 158 | 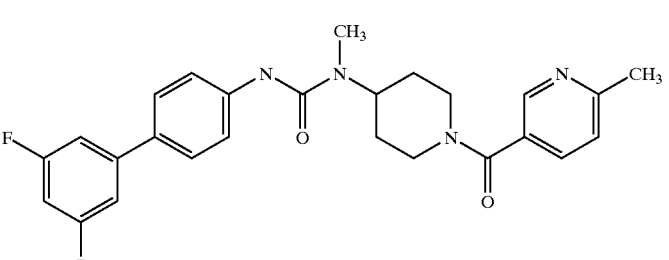 | 465 |
| 159 | 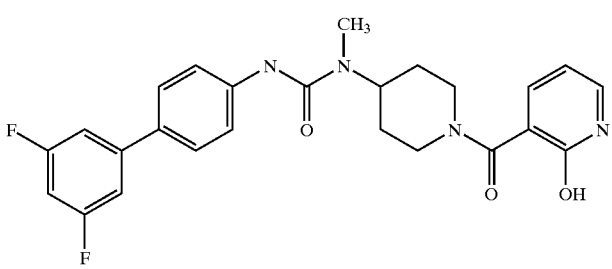 | 467 |

-continued

| Example | Structure | MSm/e (M + H) |
|---------|-----------|---------------|
| 160 | 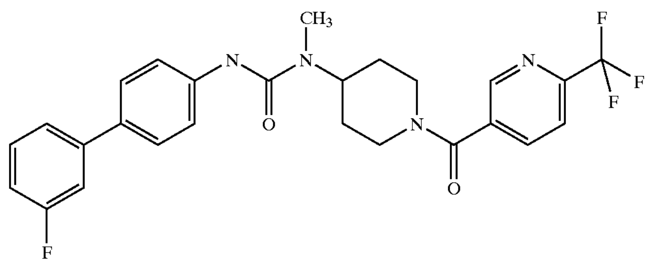 | 501 |
| 161 | 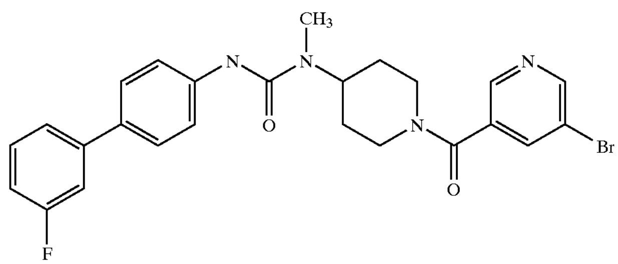 | 511 |
| 162 | 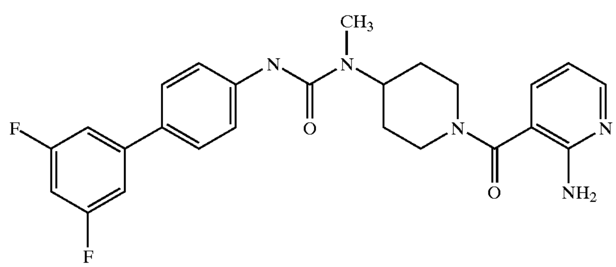 | 466 |
| 163 | 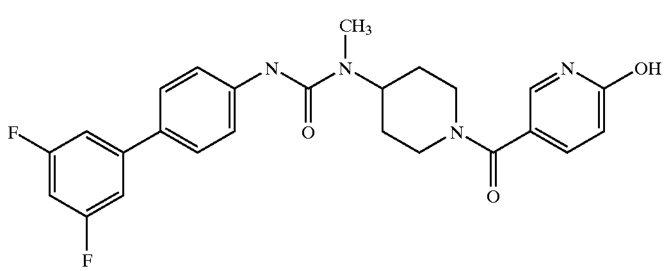 | 467 |
| 164 | 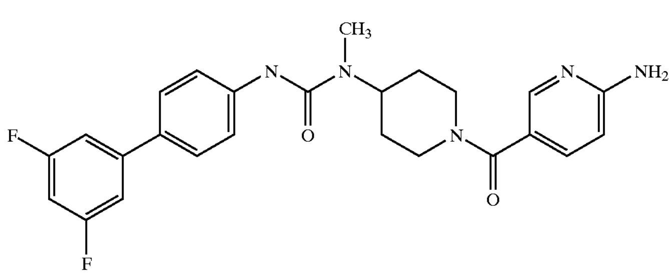 | 466 |

-continued

| Example | Structure | MSm/e (M + H) |
|---|---|---|
| 165 | 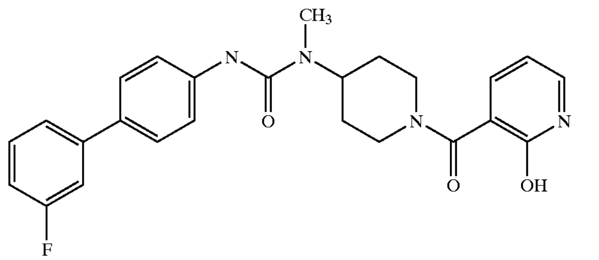 | 449 |
| 166 | 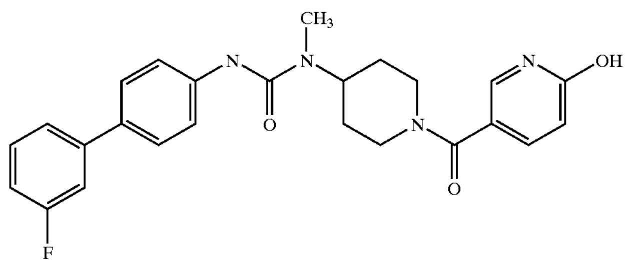 | 449 |
| 167 | 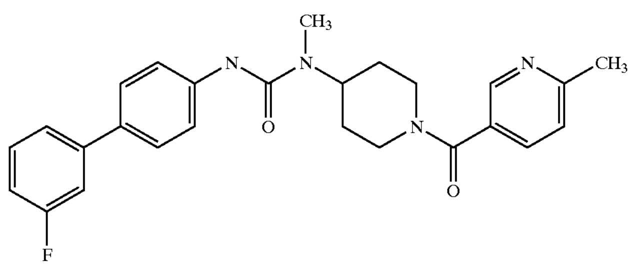 | 447 |
| 168 | 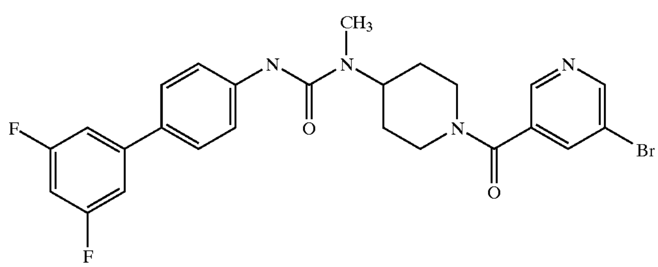 | 531 |
| 169 | 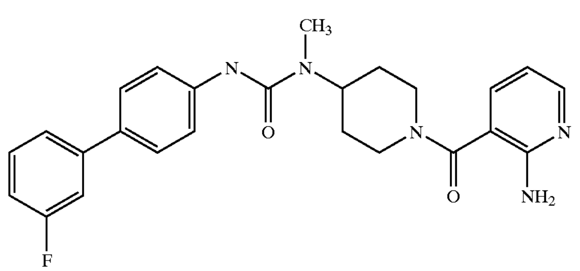 | 448 |

-continued

| Example | Structure | MSm/e (M + H) |
|---|---|---|
| 170 | 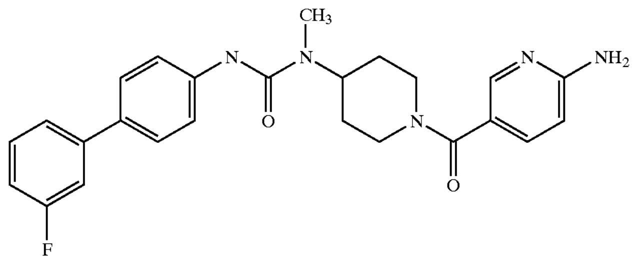 | 448 |
| 171 | 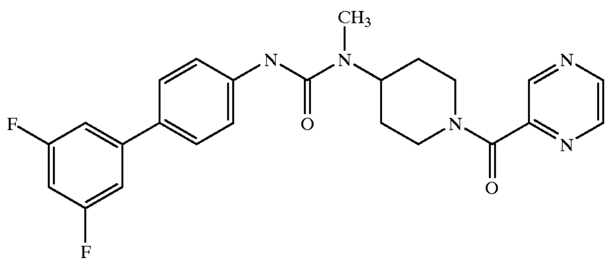 | 452 |
| 172 | 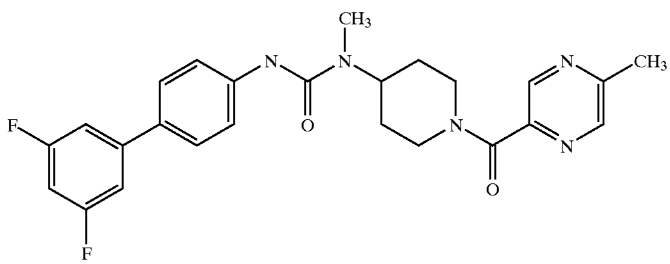 | 466 |
| 173 | 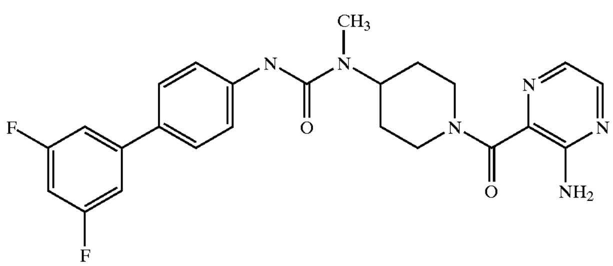 | 467 |
| 174 | 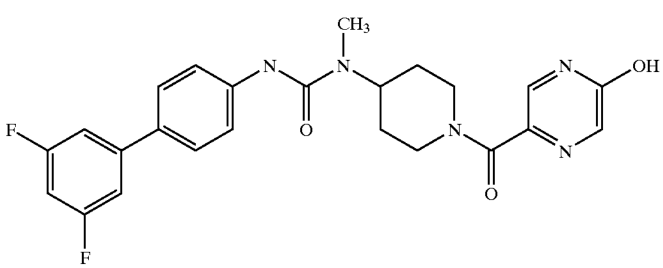 | 468 |

-continued
| Example | Structure | MSm/e (M + H) |
|---|---|---|
| 175 | 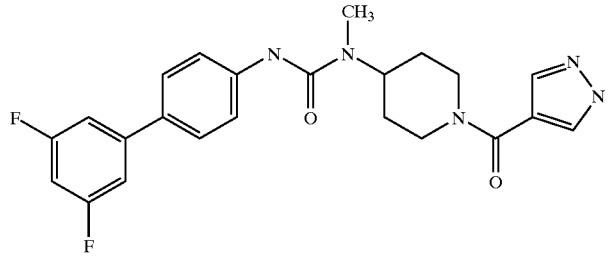 | 440 |
| 176 | 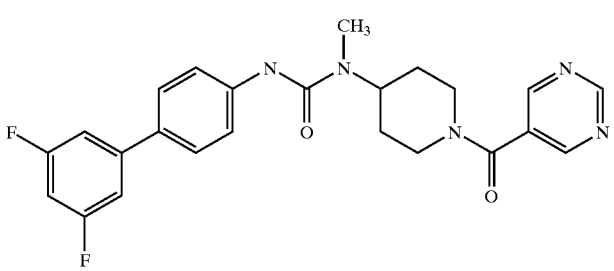 | 452 |
| 177 | 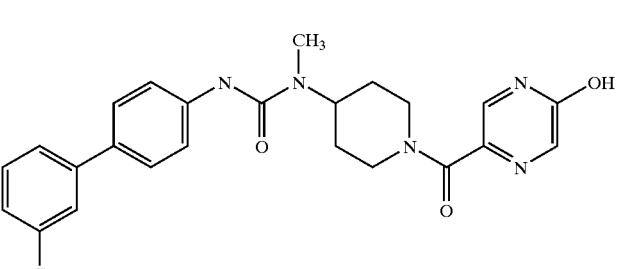 | 450 |
| 178 | 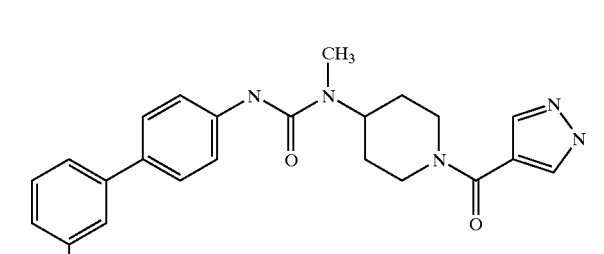 | 422 |
| 179 | 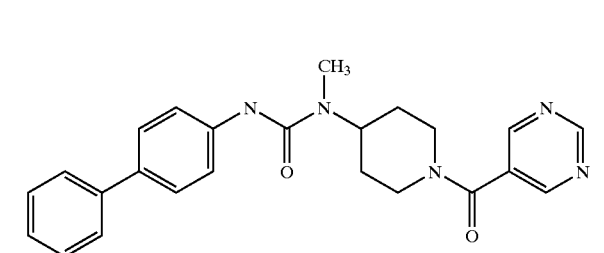 | 434 |

-continued

| Example | Structure | MSm/e (M + H) |
|---|---|---|
| 180 | 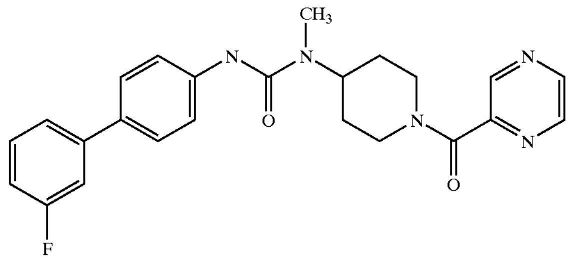 | 434 |
| 181 | 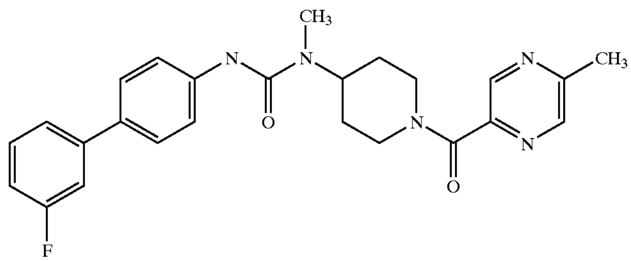 | 448 |
| 182 | 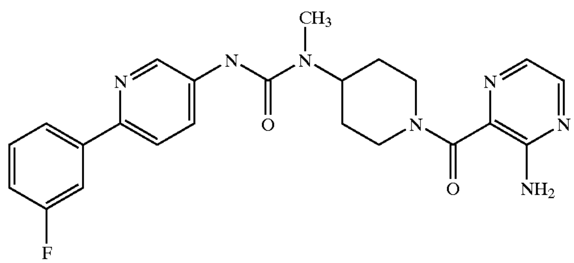 | 449 |
| 183 | 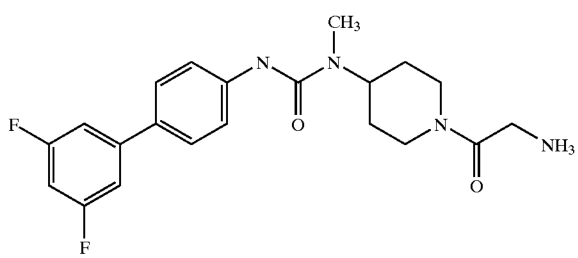 | 403 |
| 184 | 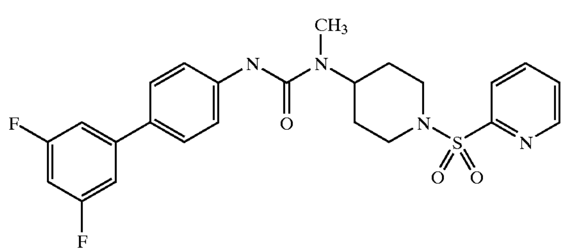 | 487 |
| 185 | 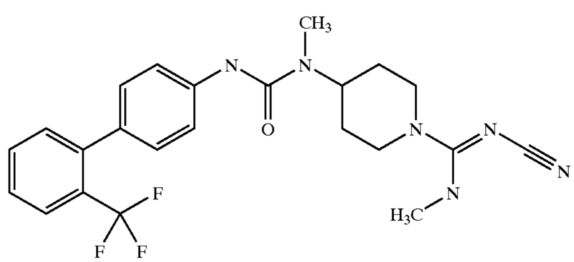 | 459 |

-continued

| Example | Structure | MSm/e (M + H) |
|---|---|---|
| 186 | 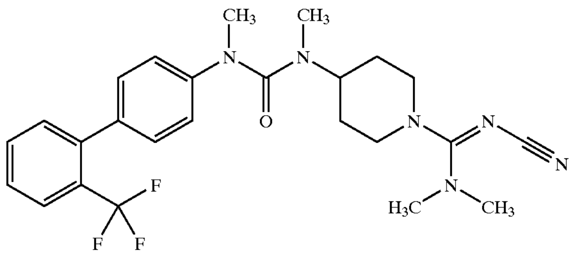 | 487 |
| 187 | 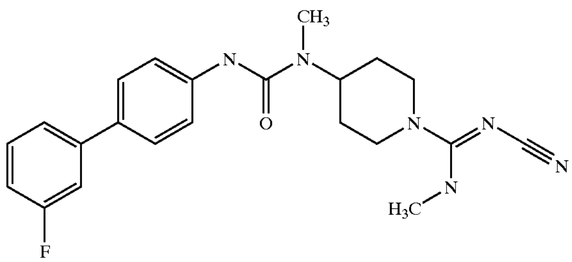 | 409 |
| 188 | 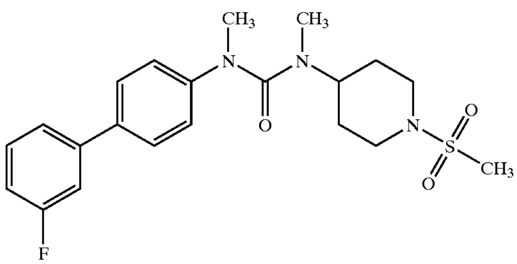 | 420 |
| 189 | 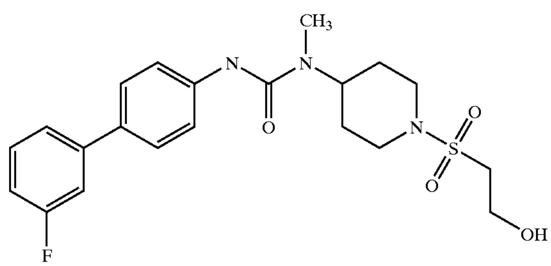 | 436 |
| 190 | 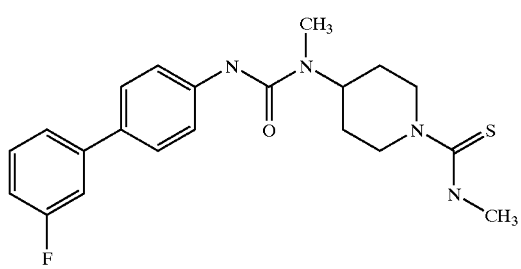 | 401 |
| 191 | 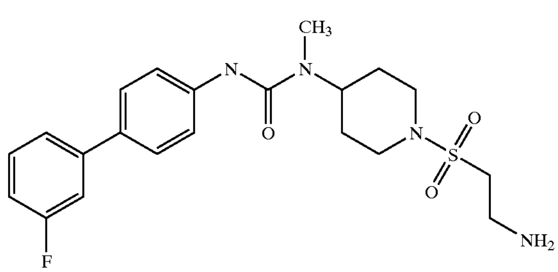 | 435 |

| Example | Structure | MSm/e (M + H) |
|---------|-----------|---------------|
| 192 | 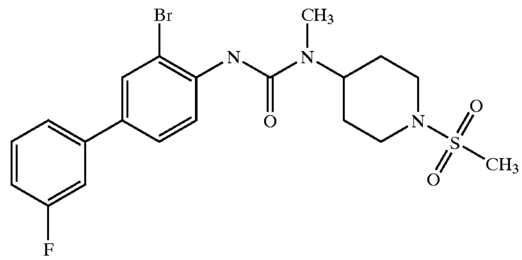 | 485 |
| 193 | 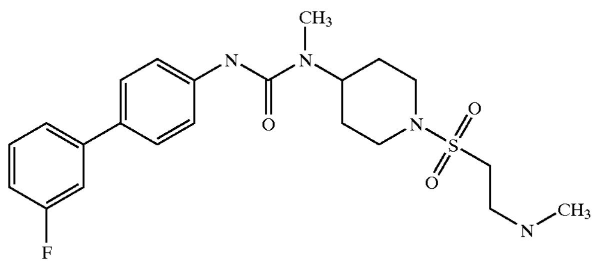 | 449 |
| 194 | 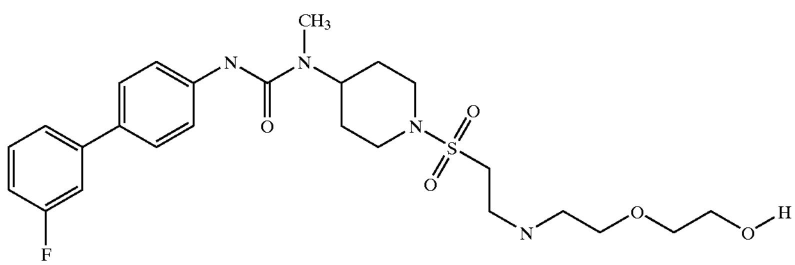 | 523 |
| 195 | 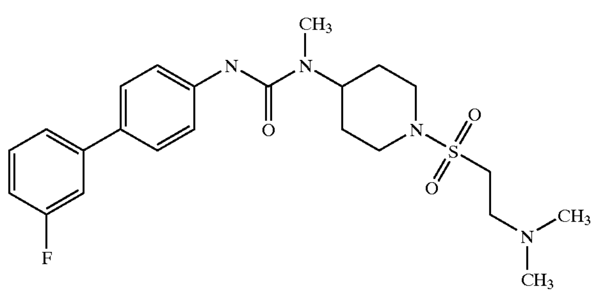 | 463 |
| 196 | 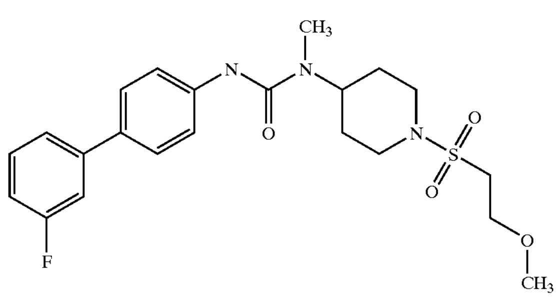 | 450 |

-continued

| Example | Structure | MSm/e (M + H) |
|---|---|---|
| 197 | 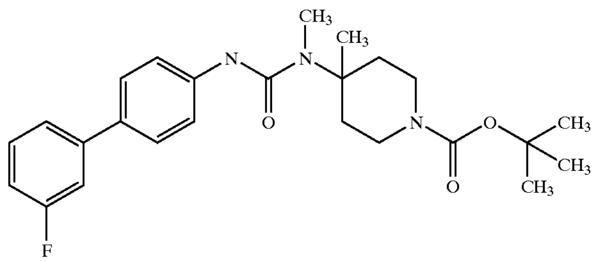 | 442 |
| 198 | 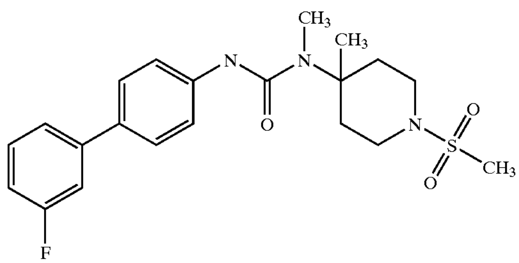 | 420 |
| 199 | 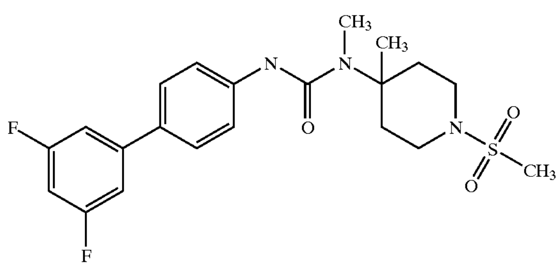 | 438 |
| 200 | 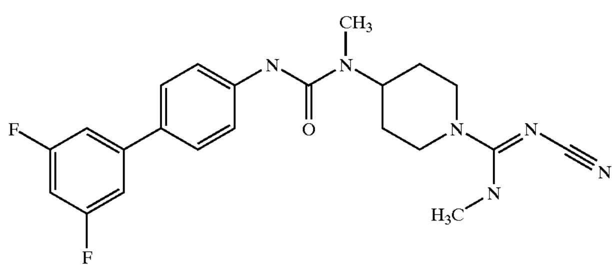 | 427 |
| 201 | 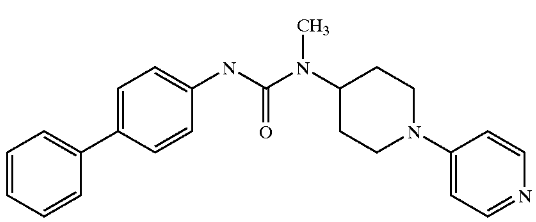 | 387.1 |
| 202 | 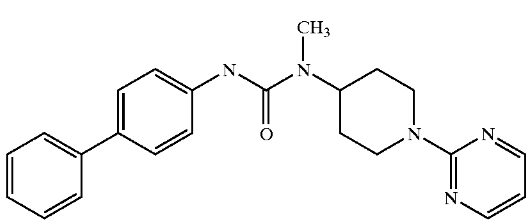 | 388.1 |

-continued
| Example | Structure | MSm/e (M + H) |
|---------|-----------|---------------|
| 203 | 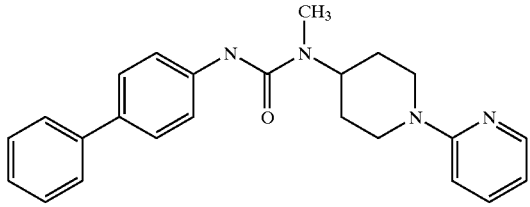 | 387.1 |
| 204 | 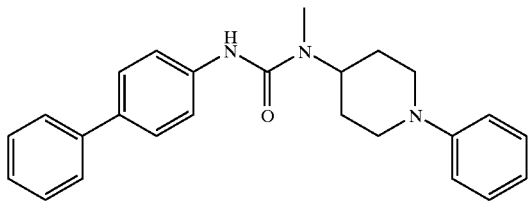 | 386.1 |
| 205 | 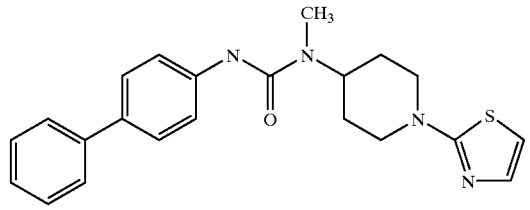 | 393.1 |
| 206 | 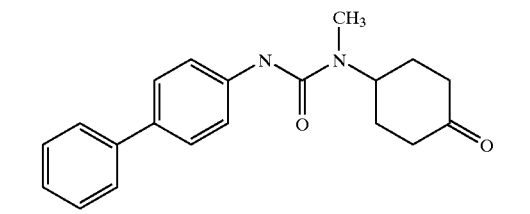 | 323.1 |
| 207 | 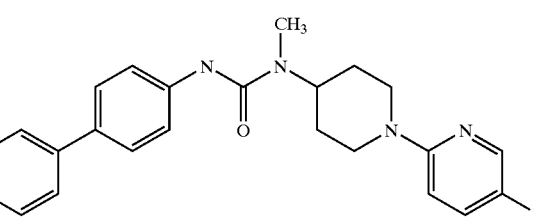 | 465.1, 467.1 |
| 208 | 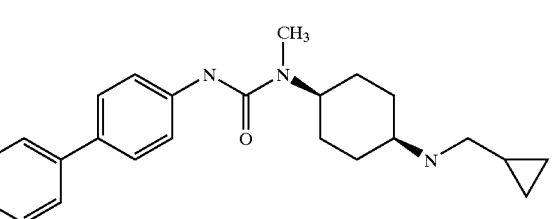 | 378.1 |
| 209 | 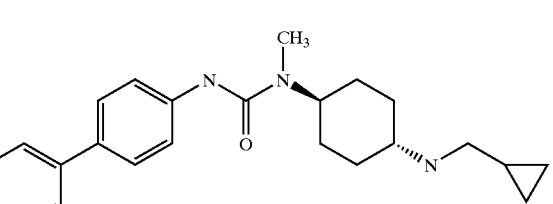 | 378.1 |

-continued

| Example | Structure | MSm/e (M + H) |
|---------|-----------|---------------|
| 210 | 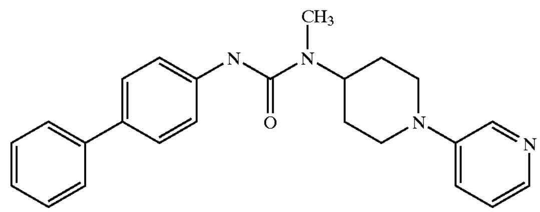 | 387.1 |
| 211 | 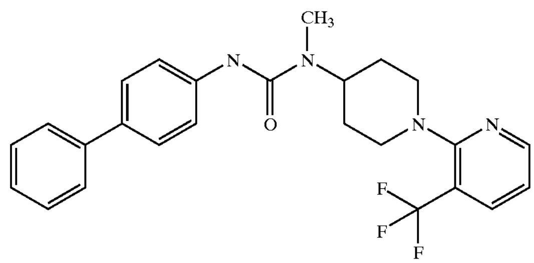 | 455.1 |
| 212 | 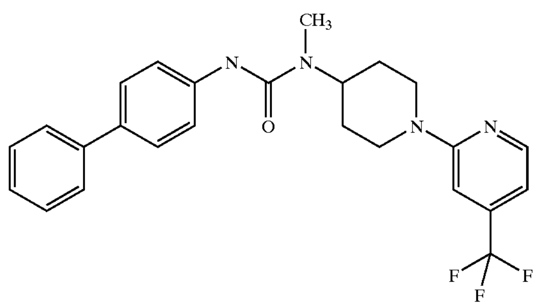 | 455.1 |
| 213 | 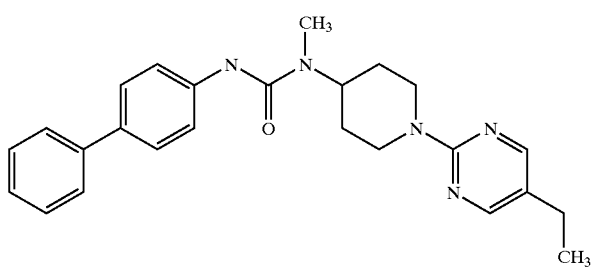 | 416.1 |
| 214 | 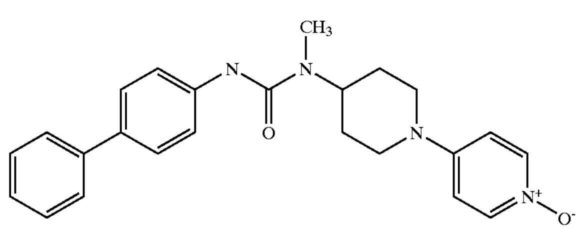 | 403.1 |
| 215 | 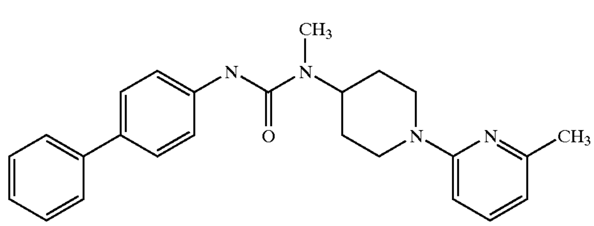 | 401.1 |

-continued
| Example | Structure | MSm/e (M + H) |
|---|---|---|
| 216 | 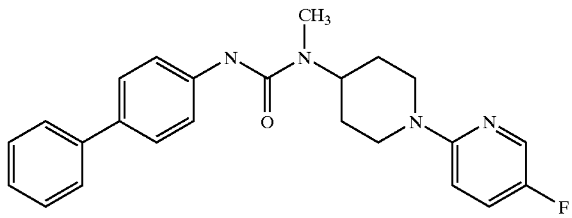 | 405.1 |
| 217 | 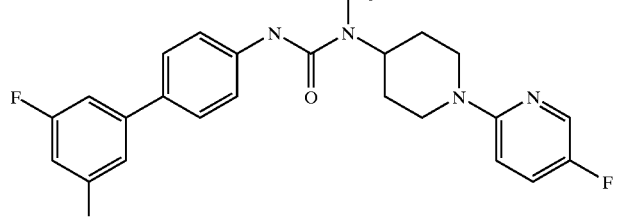 | 441.1 |
| 218 | 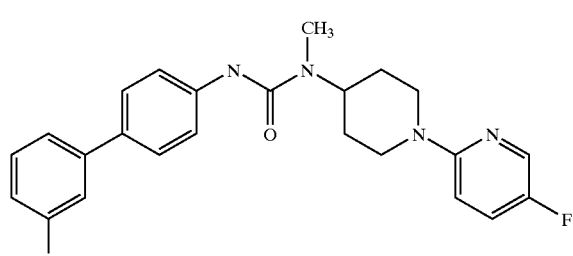 | 423.1 |
| 219 | 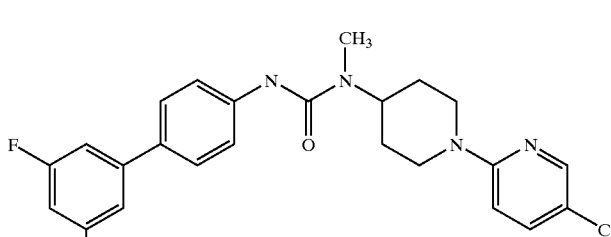 | 457.1 |
| 220 | 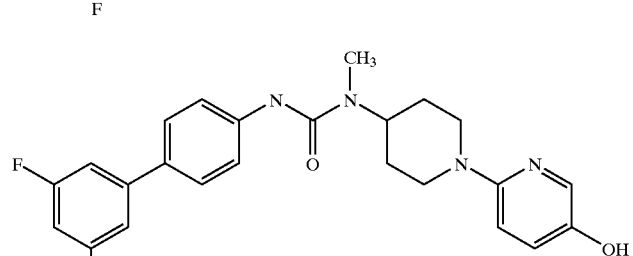 | 439.1 |
| 221 | 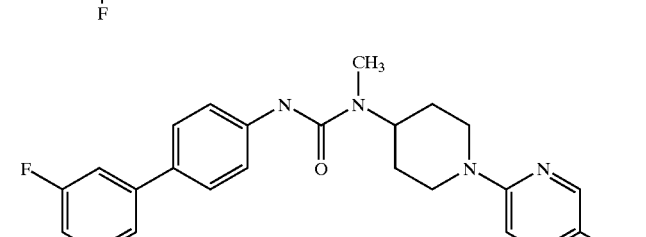 | 437.1 |

| Example | Structure | MSm/e (M + H) |
|---|---|---|
| 222 | 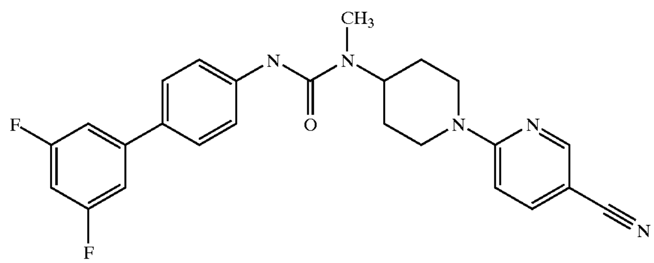 | 448.1 |
| 223 | 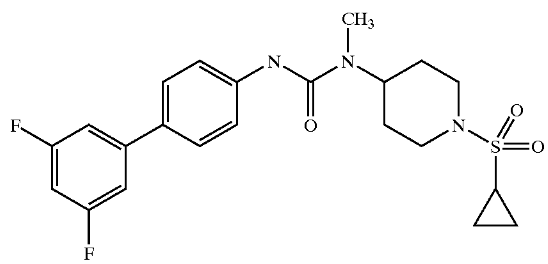 | 450.1 |
| 224 | 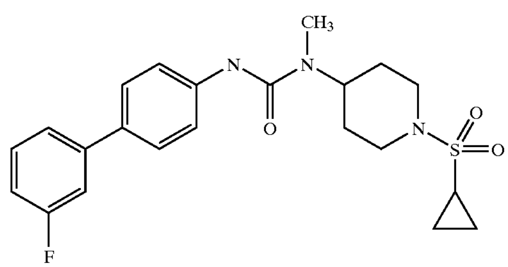 | 432.1 |
| 225 | 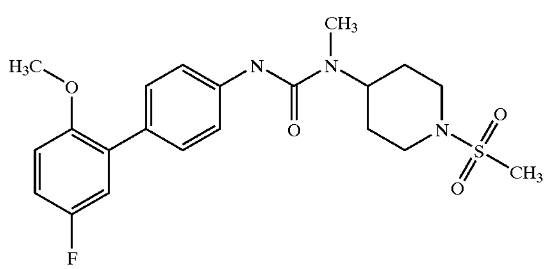 | 436.1 |
| 226 | 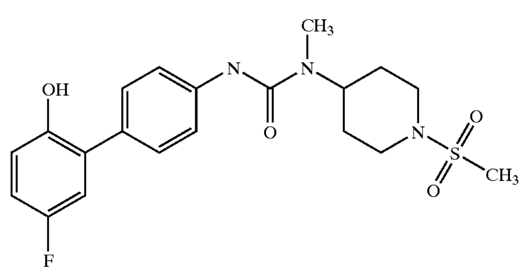 | 422.1 |

-continued

| Example | Structure | MSm/e (M + H) |
|---|---|---|
| 227 | 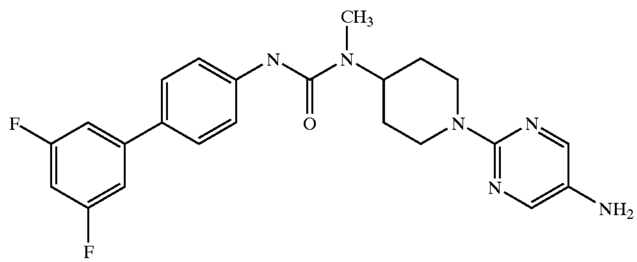 | 439.1 |
| 228 | 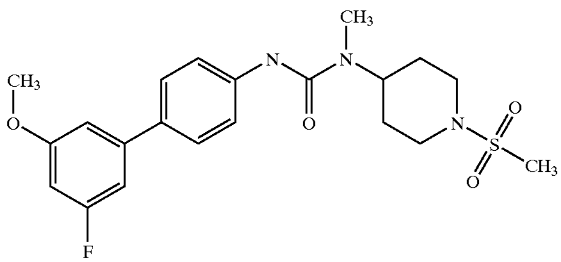 | 436.1 |
| 229 | 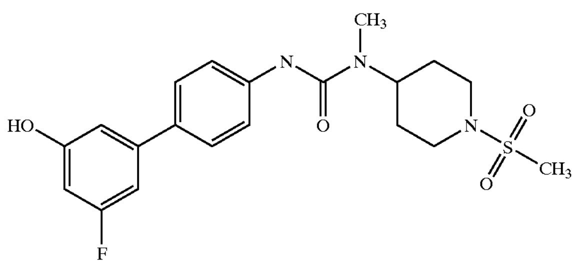 | 422.1 |
| 230 | 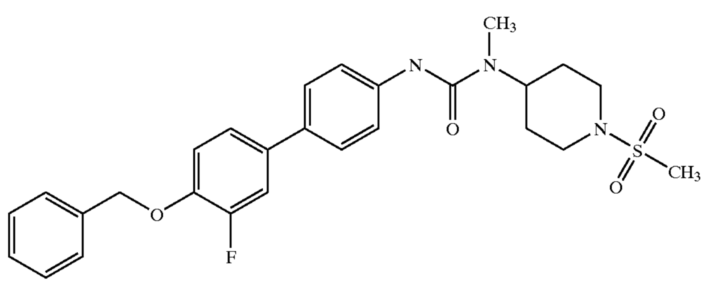 | 512.1 |
| 231 | 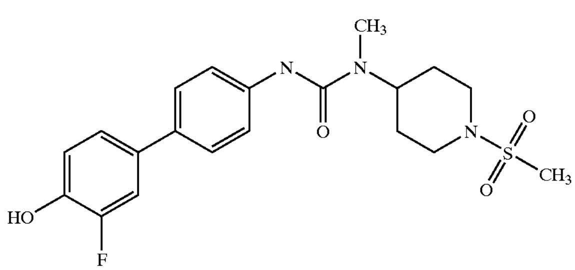 | 422.1 |

-continued

| Example | Structure | MSm/e (M + H) |
|---|---|---|
| 232 | 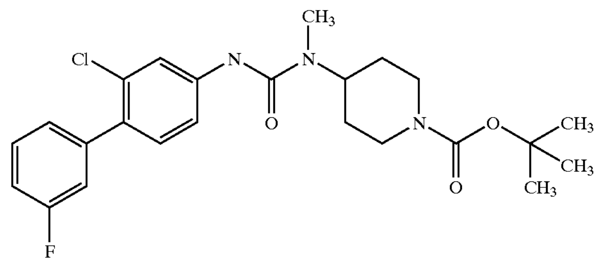 | 462.1 |
| 233 | 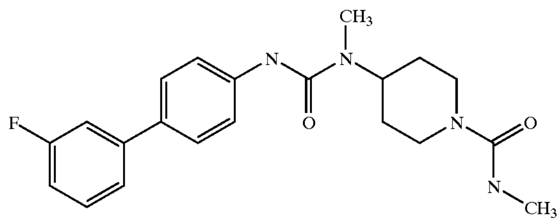 | 385 |
| 234 | 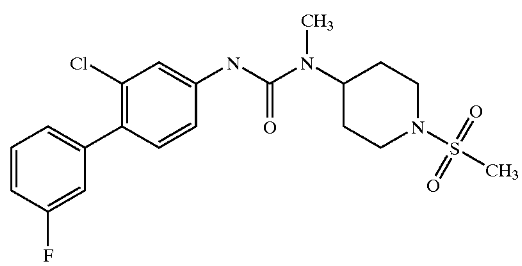 | 440.1 |
| 235 | 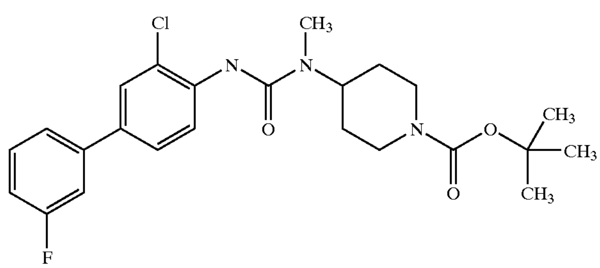 | 462.1 |
| 236 | 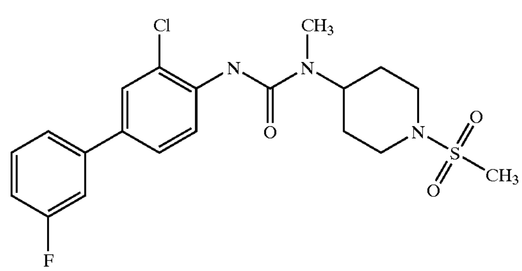 | 440.1 |
| 237 | 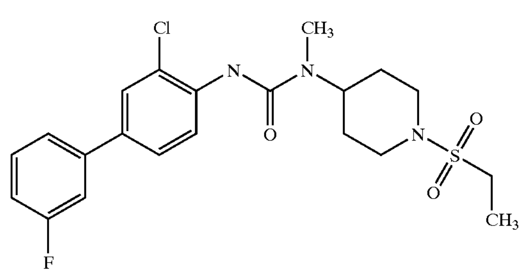 | 454.1 |

| Example | Structure | MSm/e (M + H) |
|---|---|---|
| 238 | 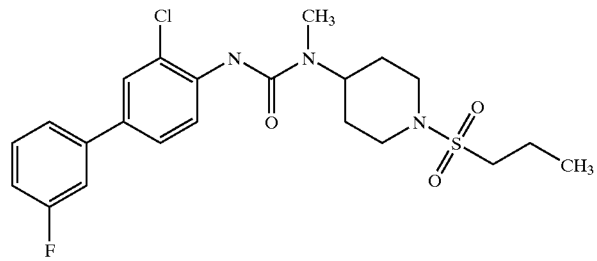 | 468.1 |
| 239 | 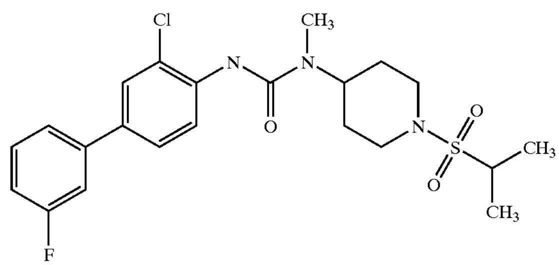 | 468.1 |
| 240 | 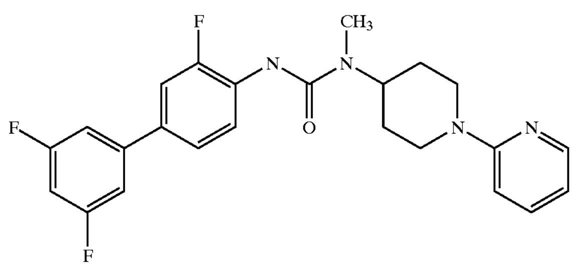 | 441 |
| 241 | 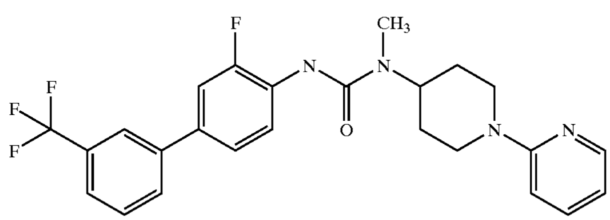 | 473 |
| 242 | 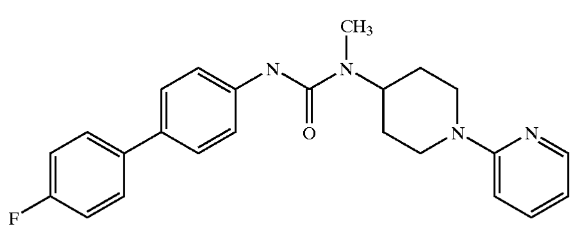 | 405 |
| 243 | 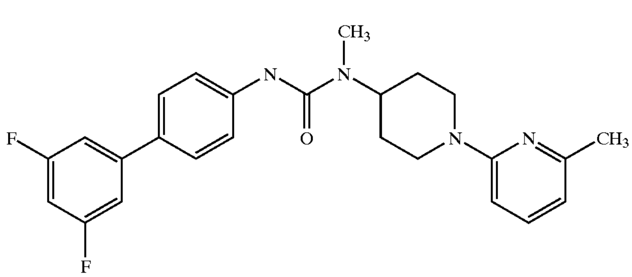 | 437 |

| Example | Structure | MSm/e (M + H) |
|---|---|---|
| 244 | 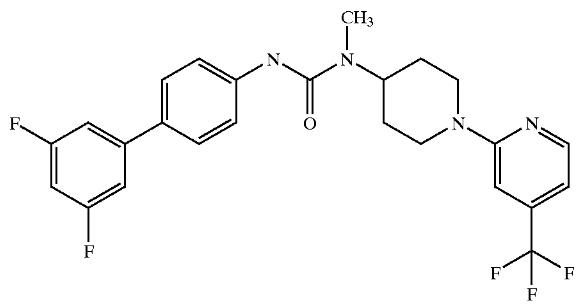 | 491 |
| 245 | 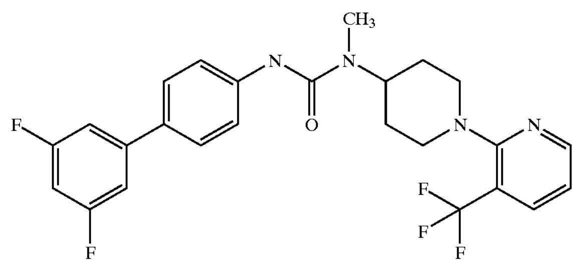 | 491 |
| 246 | 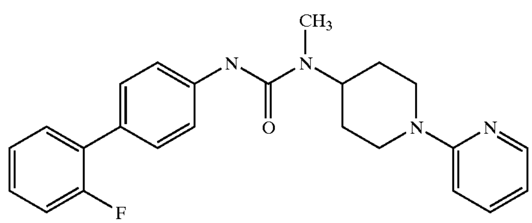 | 405 |
| 247 | 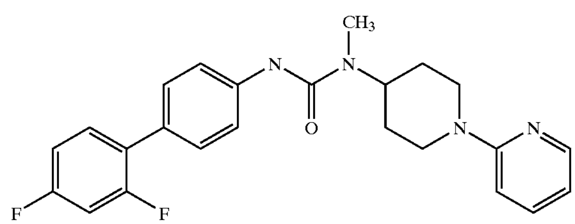 | 423 |
| 248 | 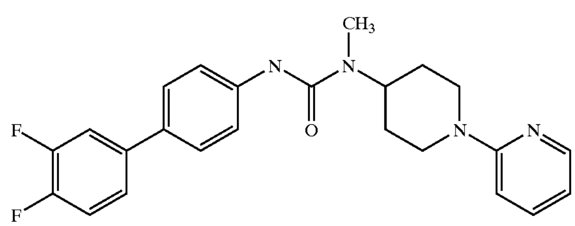 | 423 |
| 249 | 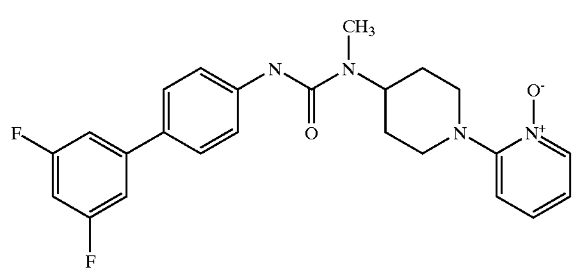 | 439 |

-continued

| Example | Structure | MSm/e (M + H) |
|---------|-----------|---------------|
| 250 | 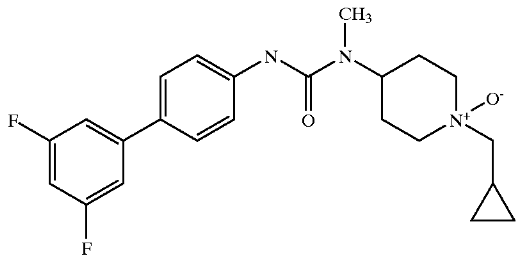 | 416 |
| 251 | 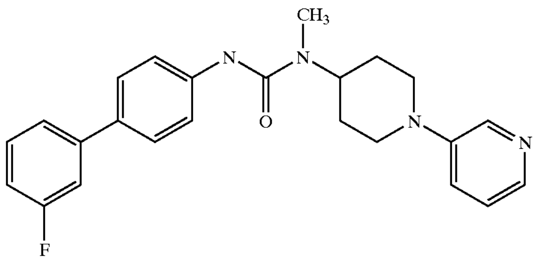 | 405 |
| 252 | 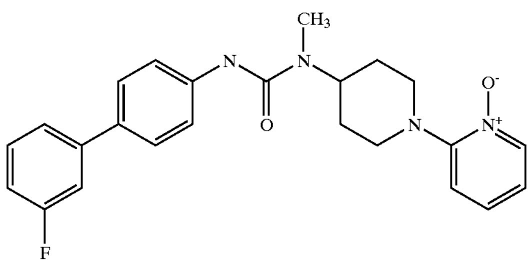 | 421 |
| 253 | 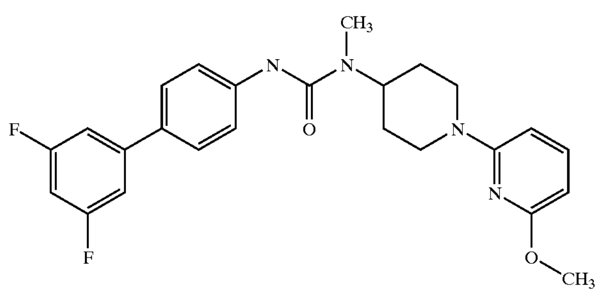 | 453 |
| 254 | 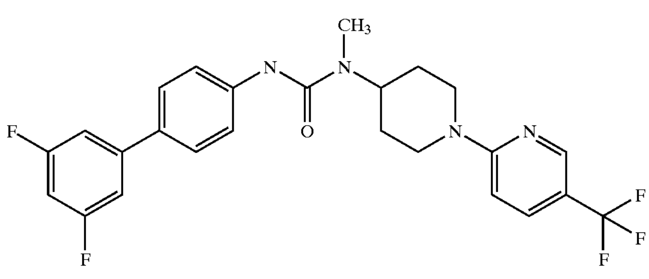 | 491 |

-continued

| Example | Structure | MSm/e (M + H) |
|---|---|---|
| 255 | 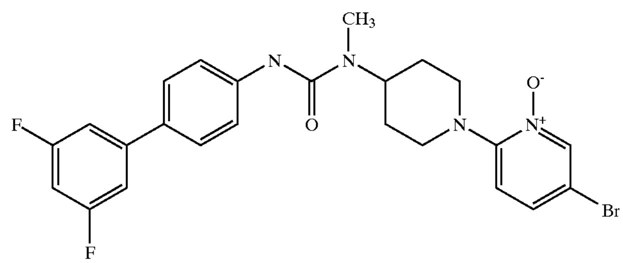 | 501 |
| 256 | 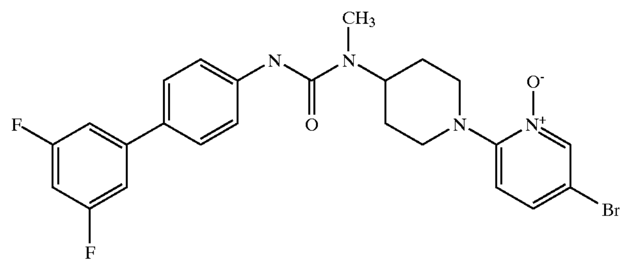 | 517 |
| 257 | 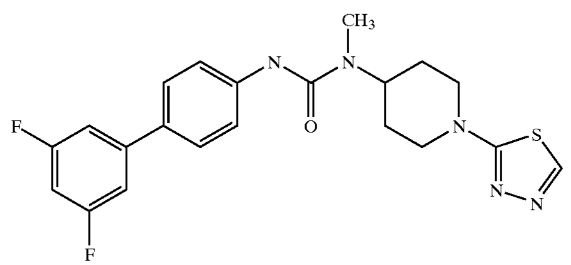 | 430 |
| 258 | 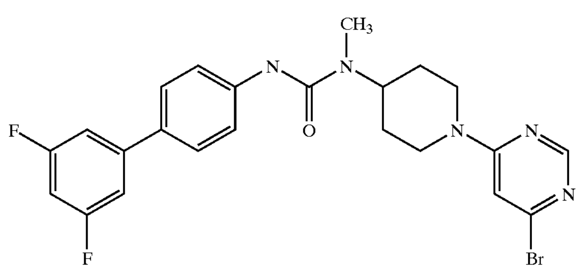 | 458 |
| 259 | 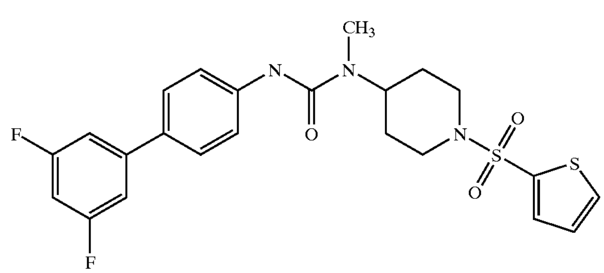 | 492 |

-continued
| Example | Structure | MSm/e (M + H) |
|---|---|---|
| 260 | 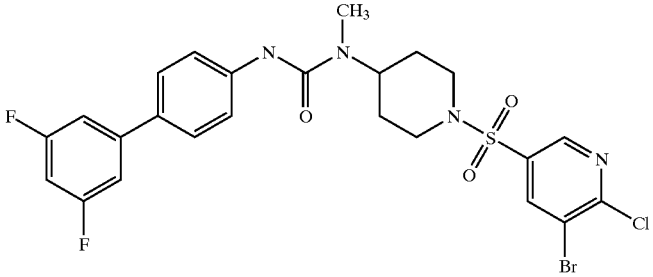 | 599 |
| 261 | 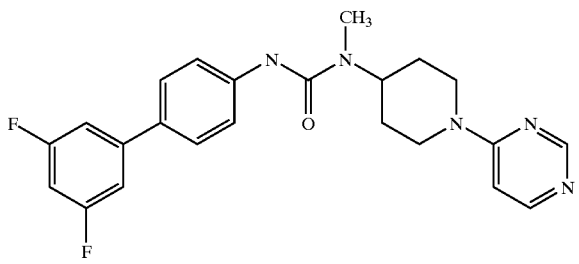 | 424 |
| 262 | 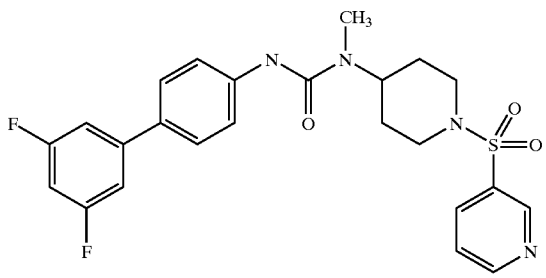 | 487 |
| 263 | 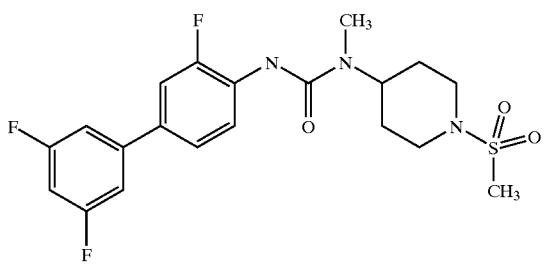 | 442 |
| 264 | 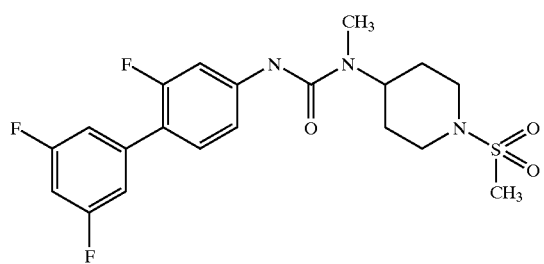 | 442 |

-continued

| Example | Structure | MSm/e (M + H) |
|---|---|---|
| 265 | 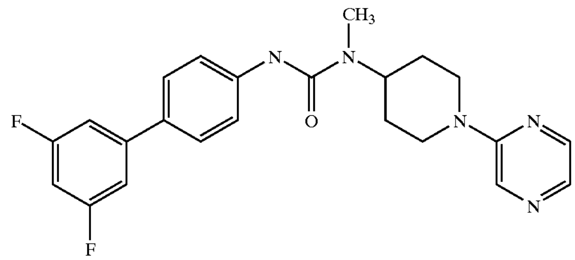 | 424 |
| 266 | 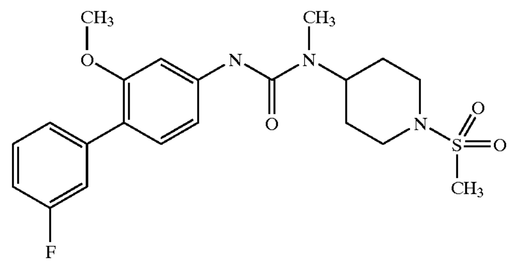 | 436 |
| 267 | 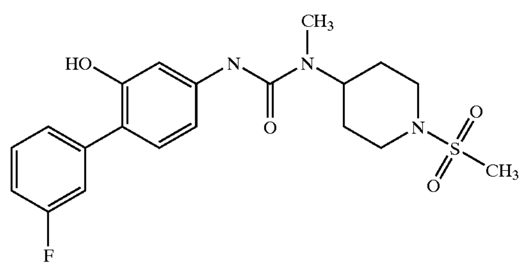 | 422 |
| 268 | 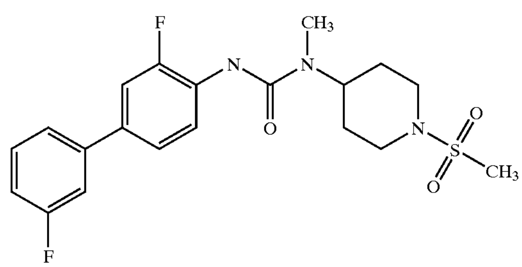 | 424 |
| 269 | 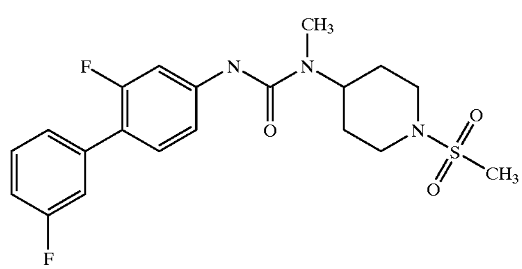 | 424 |

-continued
| Example | Structure | MSm/e (M + H) |
|---|---|---|
| 270 | 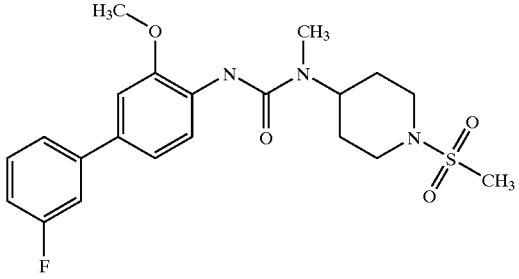 | 436 |
| 271 | 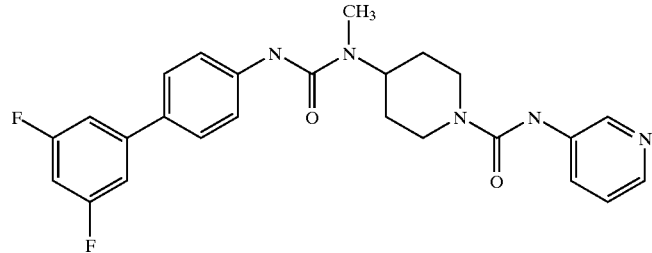 | 466 |
| 272 | 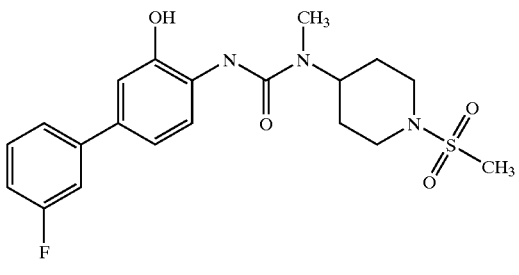 | 422 |
| 273 | 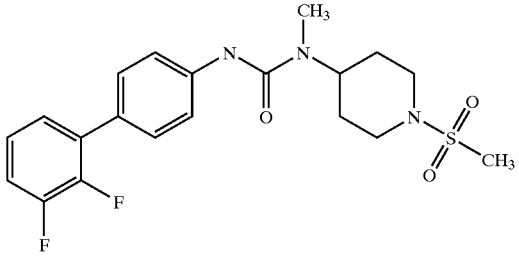 | 424 |
| 274 | 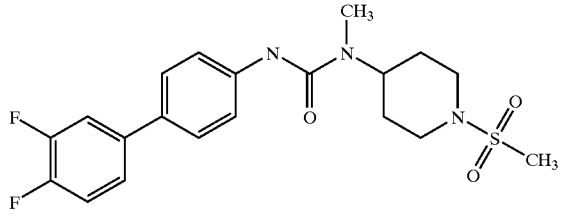 | 424 |
| 275 | 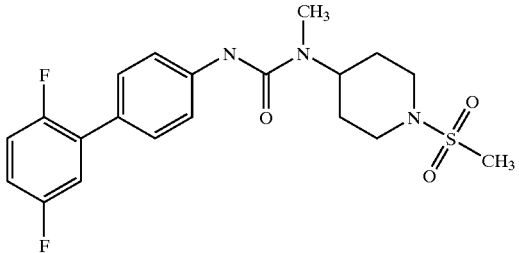 | 424 |

-continued

| Example | Structure | MSm/e (M + H) |
|---------|-----------|---------------|
| 276 | 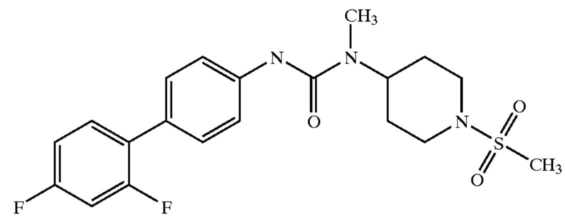 | 424 |
| 277 | 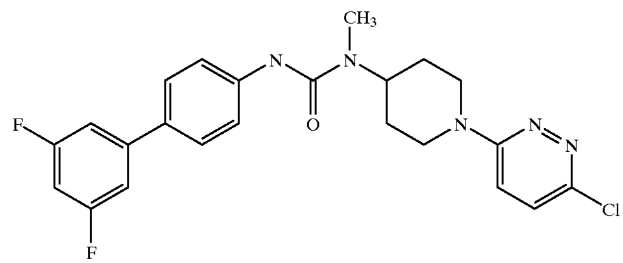 | 458 |
| 278 | 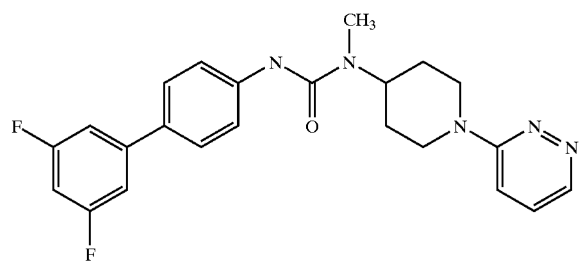 | 424 |
| 279 | 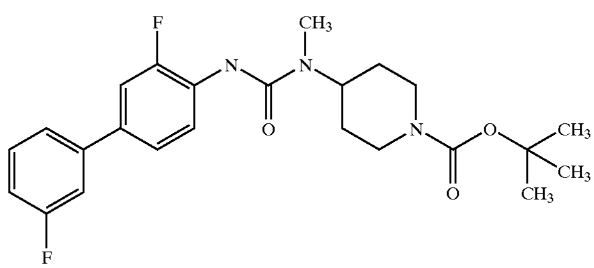 | 446 |
| 280 | 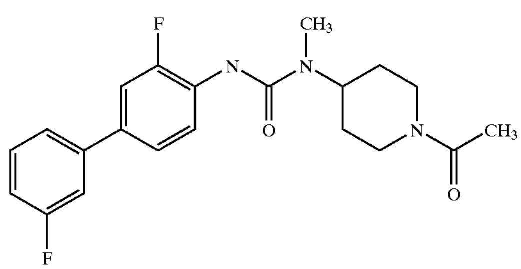 | 388 |
| 281 | 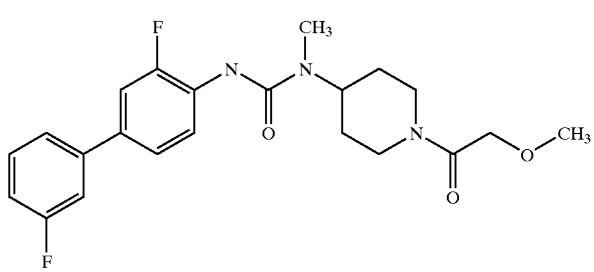 | 418 |

-continued

| Example | Structure | MSm/e (M + H) |
|---|---|---|
| 282 | 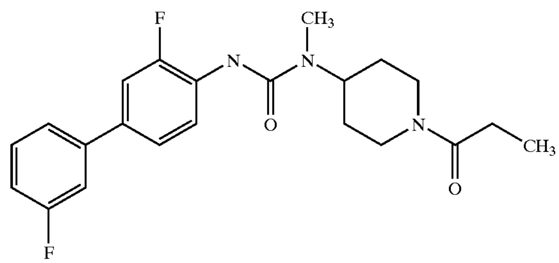 | 402 |
| 283 | 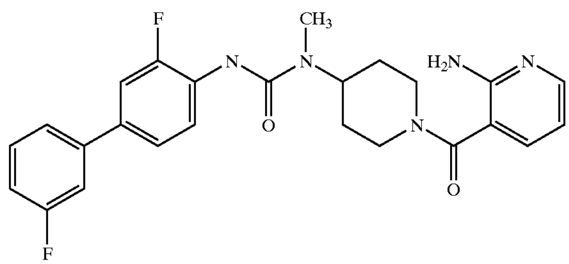 | 466 |
| 284 | 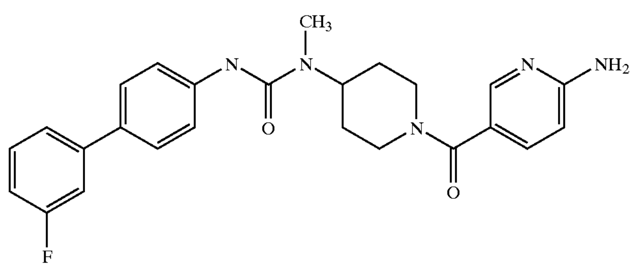 | 466 |
| 285 | 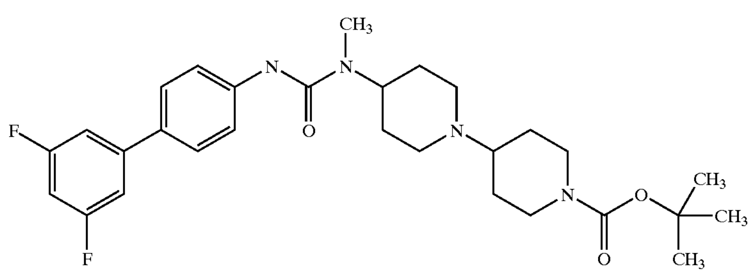 | 529 |
| 286 | 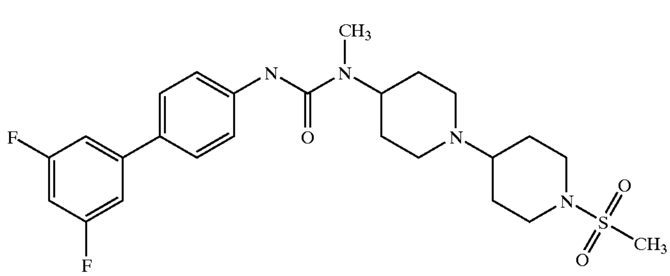 | 507 |

-continued

| Example | Structure | MSm/e (M + H) |
|---|---|---|
| 287 | 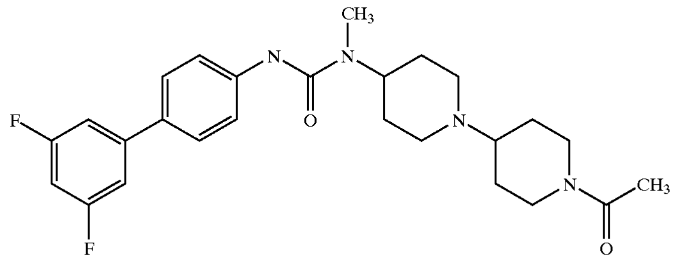 | 471 |
| 288 | 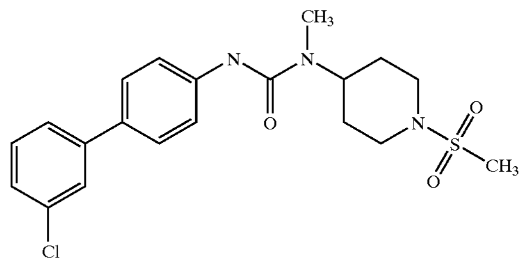 | 422 |
| 289 | 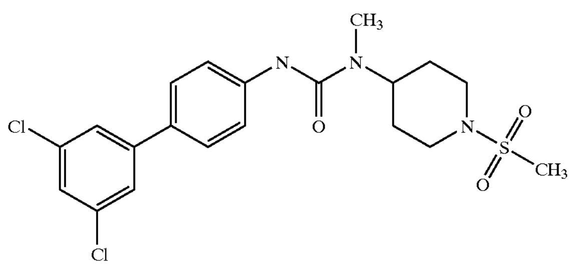 | 456 |
| 290 | 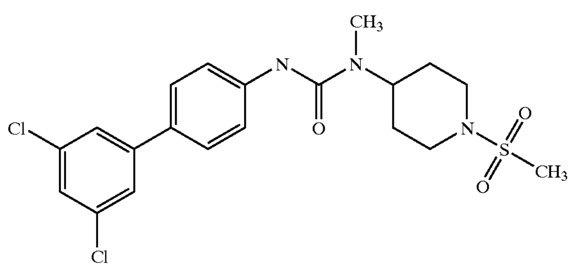 | 456 |
| 291 | 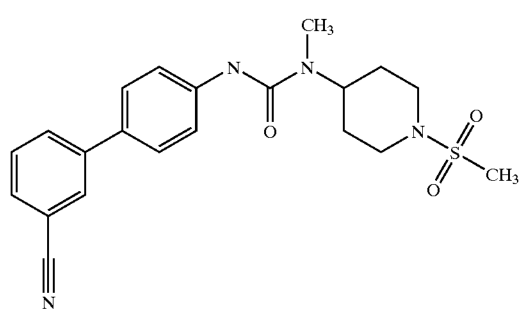 | 413 |

-continued
| Example | Structure | MSm/e (M + H) |
|---|---|---|
| 292 | 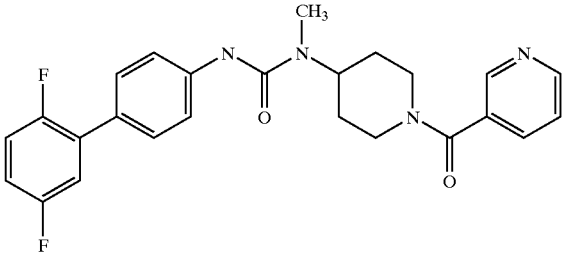 | 451 |
| 293 | 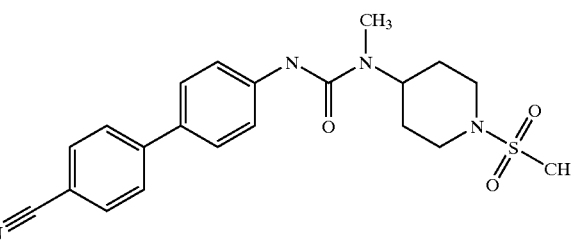 | 413 |
| 294 | 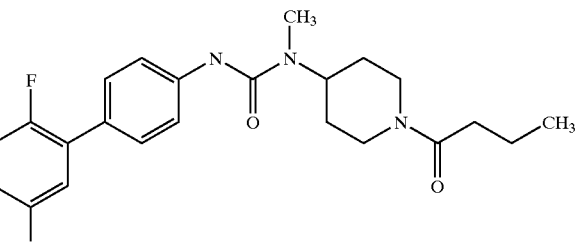 | 416 |
| 295 | 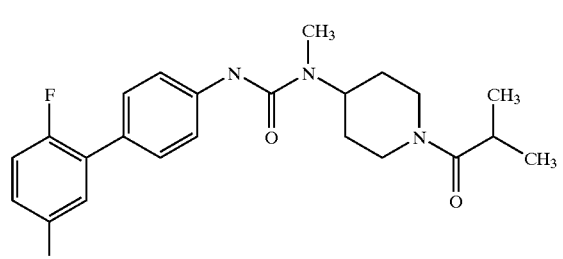 | 416 |
| 296 | 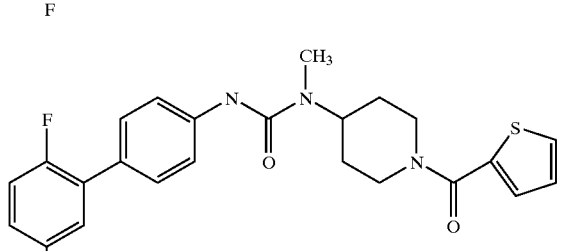 | 456 |
| 297 | 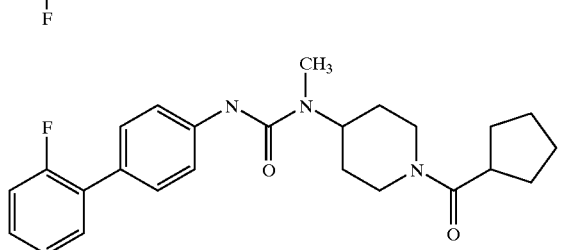 | 442 |

-continued
| Example | Structure | MSm/e (M + H) |
|---|---|---|
| 298 | 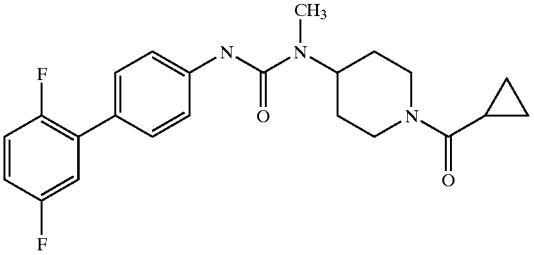 | 414 |
| 299 | 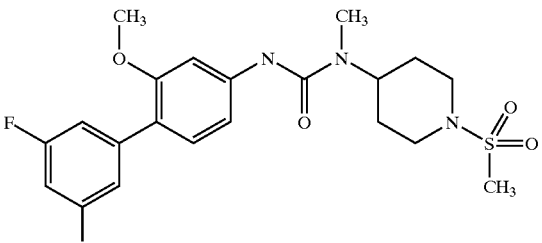 | 454 |
| 300 | 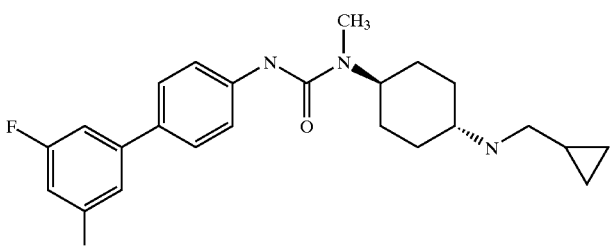 | 414 |
| 301 | 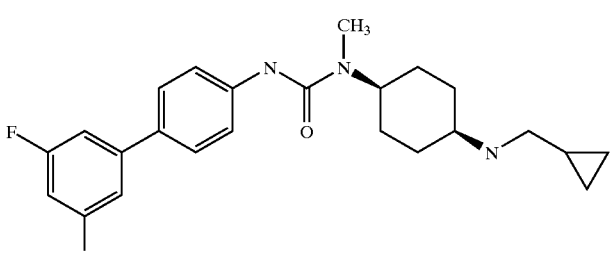 | 414 |
| 302 | 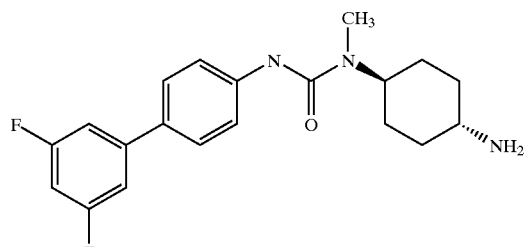 | 360 |

-continued

| Example | Structure | MSm/e (M + H) |
|---|---|---|
| 303 | 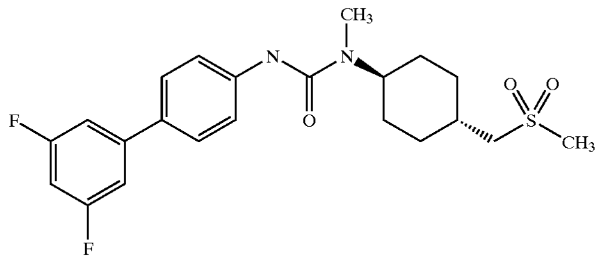 | 438 |
| 304 | 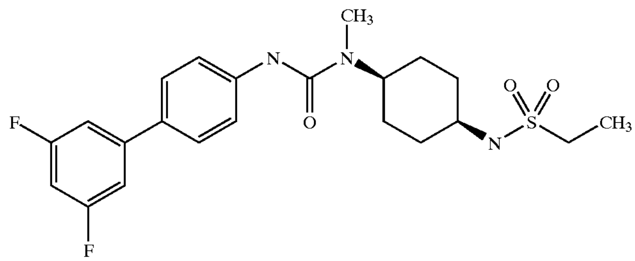 | 452 |
| 305 | 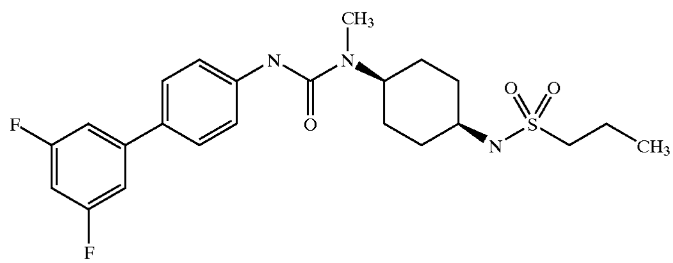 | 466 |
| 306 | 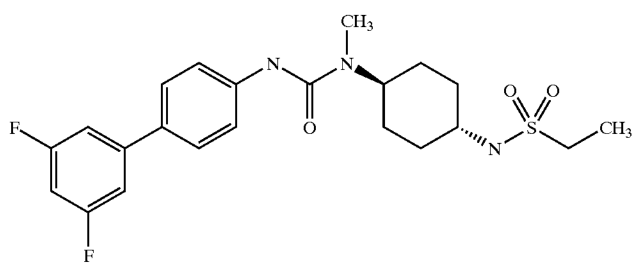 | 452 |
| 307 | 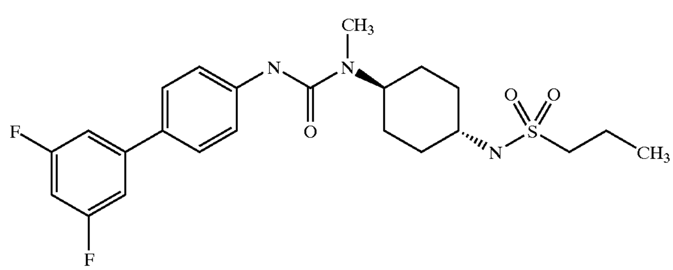 | 466 |

-continued

| Example | Structure | MSm/e (M + H) |
| --- | --- | --- |
| 308 | 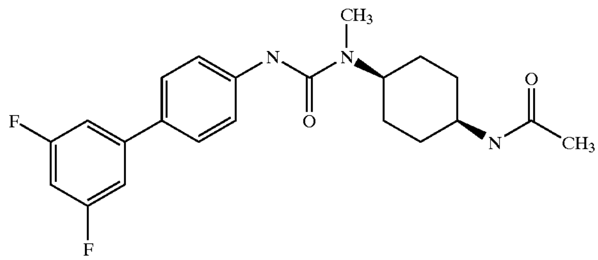 | 402 |
| 309 | 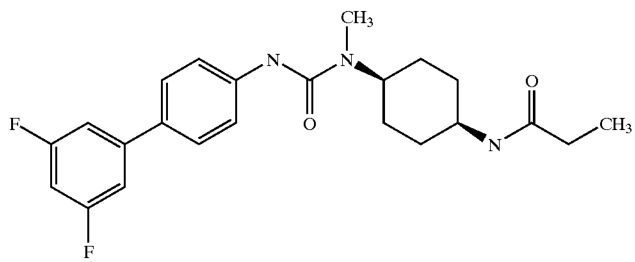 | 416 |
| 310 | 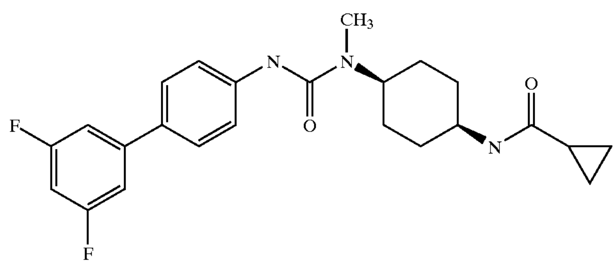 | 428 |
| 311 | 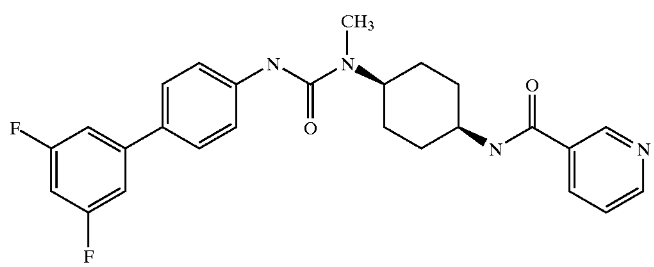 | 465 |
| 312 | 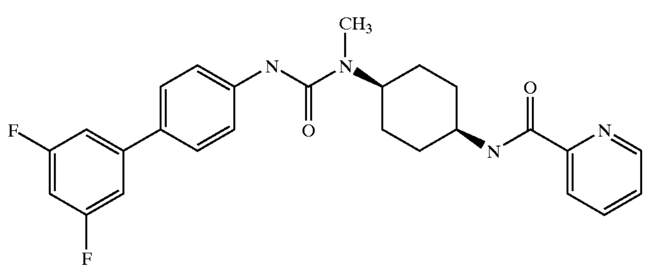 | 465 |

| Example | Structure | MSm/e (M + H) |
|---|---|---|
| 314 | 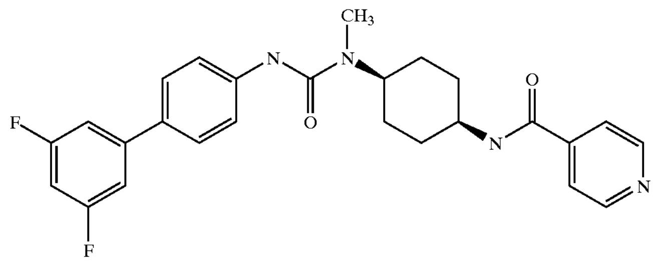 | 465 |
| 315 | 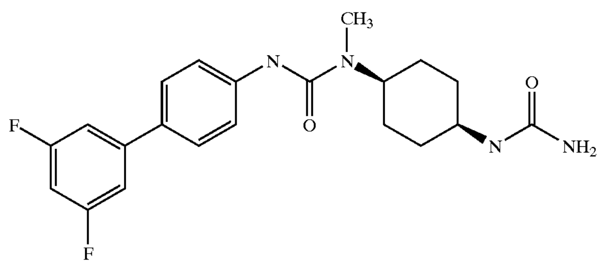 | 403 |
| 316 | 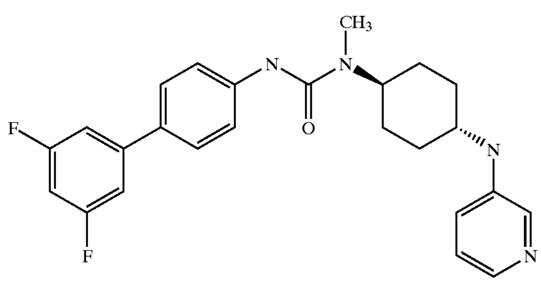 | 437 |
| 317 | 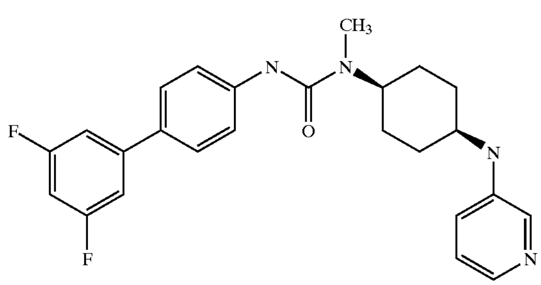 | 437 |
| 318 | 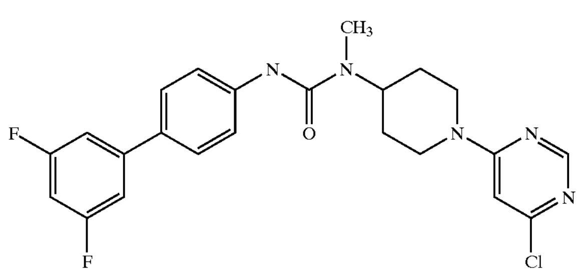 | 458 |

-continued

| Example | Structure | MSm/e (M + H) |
|---|---|---|
| 319 | 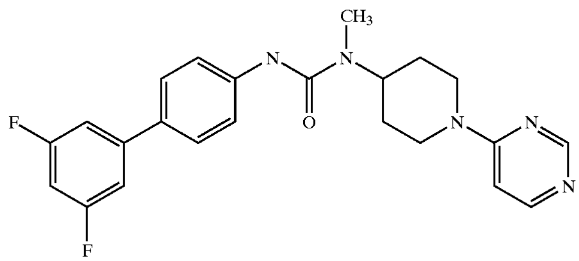 | 424 |
| 320 | 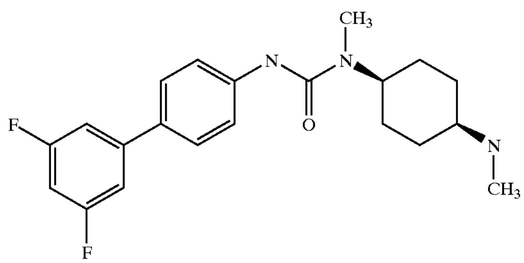 | 374 |
| 321 | 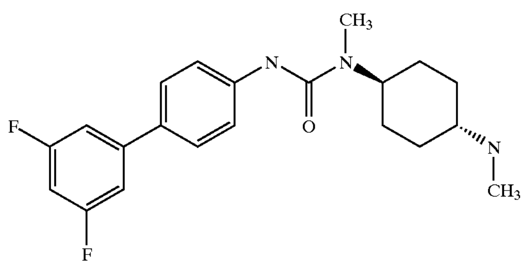 | 374 |
| 322 | 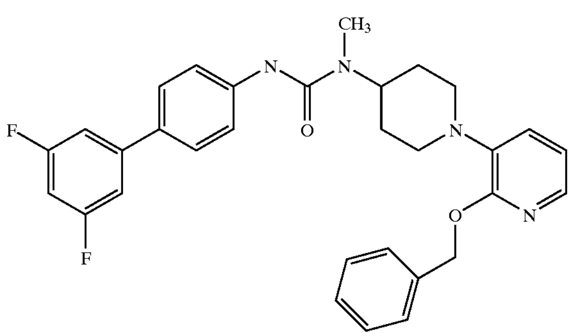 | 529 |
| 323 | 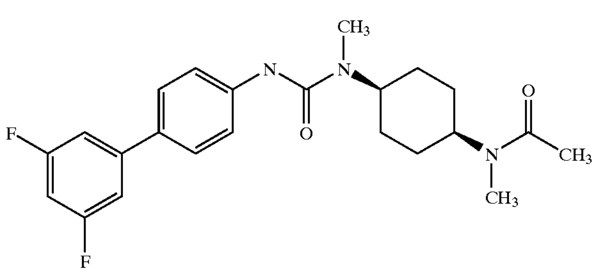 | 416 |

-continued
| Example | Structure | MSm/e (M + H) |
| --- | --- | --- |
| 324 | 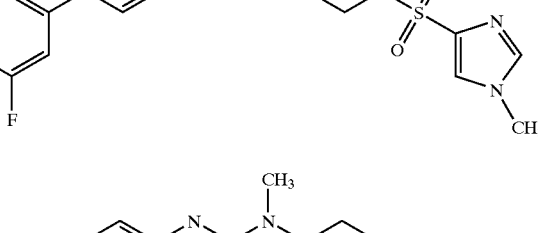 | 490 |
| 325 | 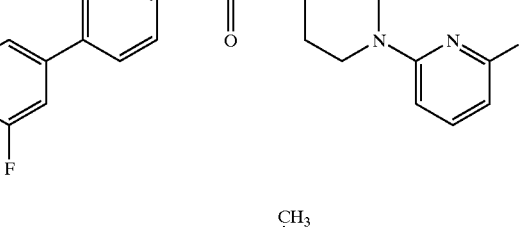 | 439 |
| 326 | 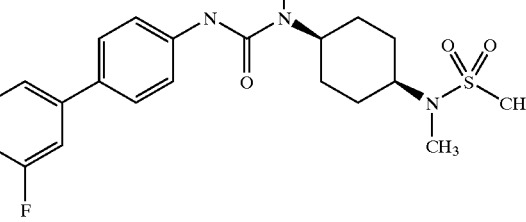 | 452 |
| 327 | 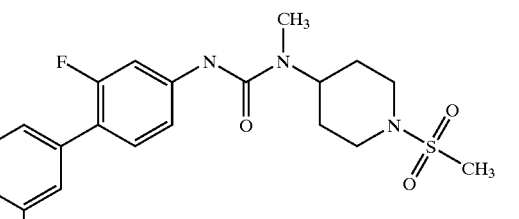 | 424 |
| 328 | 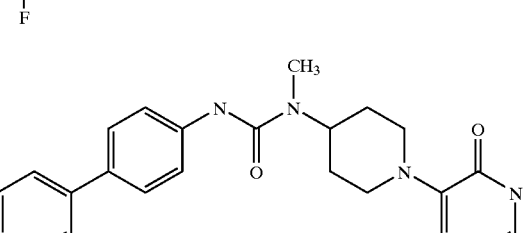 | 439 |
| 329 | 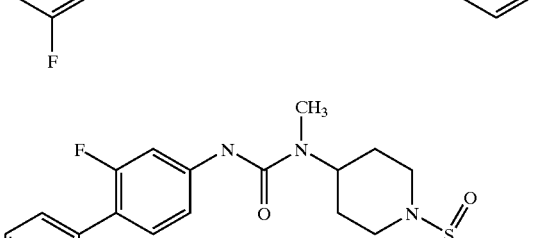 | 424 |

| Example | Structure | MSm/e (M + H) |
|---|---|---|
| 330 | 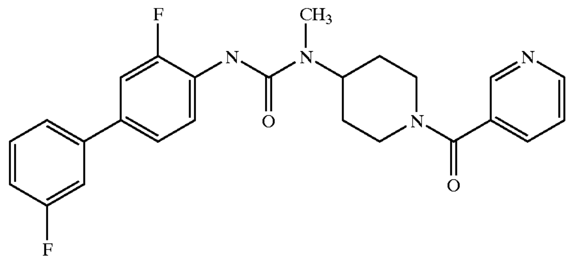 | 451 |
| 331 | 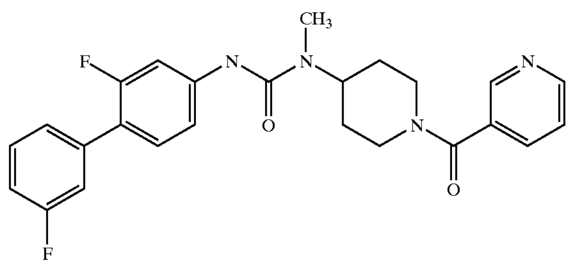 | 451 |
| 332 | 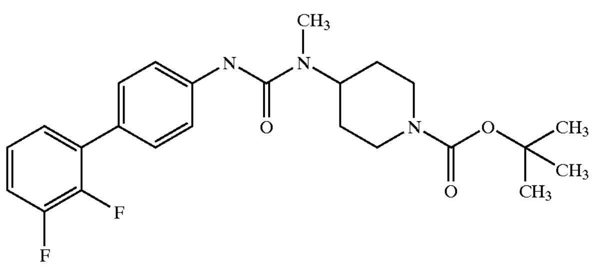 | 446 |
| 333 | 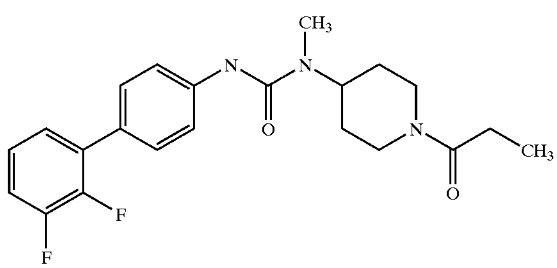 | 402 |
| 334 | 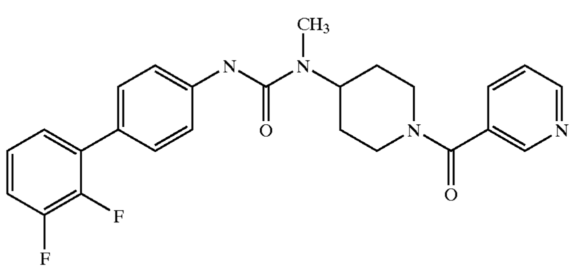 | 451 |

-continued

| Example | Structure | MSm/e (M + H) |
|---|---|---|
| 335 | 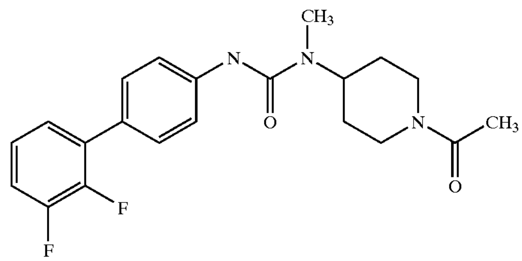 | 388 |
| 336 | 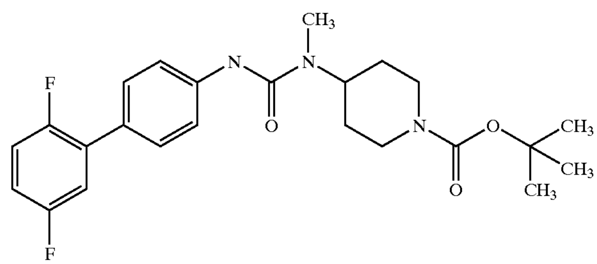 | 446 |
| 337 | 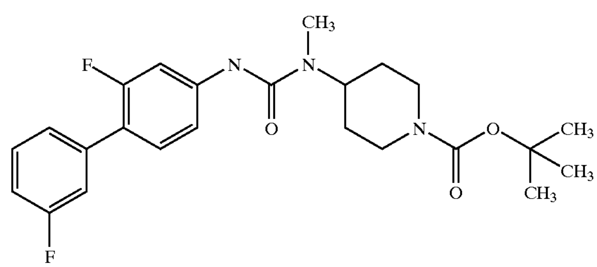 | 446 |
| 338 | 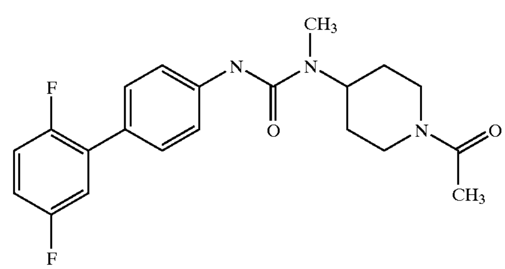 | 388 |
| 339 | 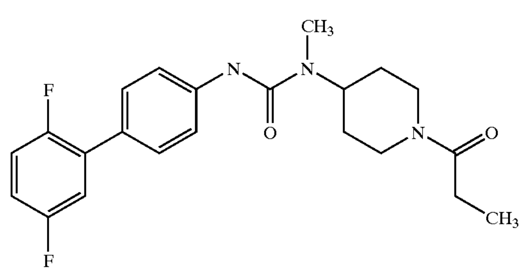 | 402 |

| Example | Structure | MSm/e (M + H) |
|---|---|---|
| 340 | 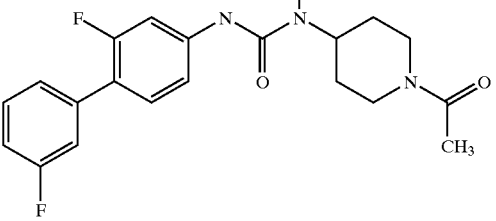 | 388 |
| 341 | 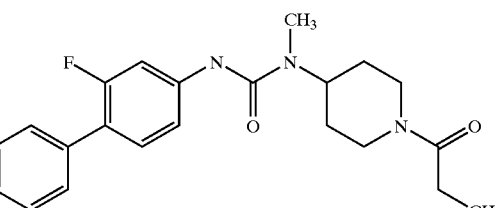 | 402 |
| 342 | 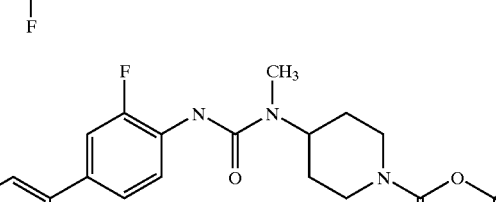 | 464 |

The preferred compounds of the present invention include the compounds of Examples: 29–59, 61–90, 95–216, 218–219, 221–262, 265, 267, 269–294, 296–297, 299–326, 328–337, 340–342 and their pharmaceutically acceptable addition salts and/or hydrates thereof, or where applicable, geometric or optical isomers or a racemic mixtures thereof.

What is claimed:

1. A compound having the structural formula I:

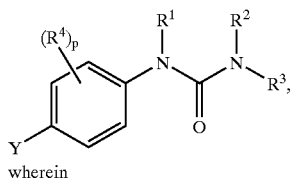

wherein

Y is 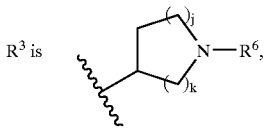

$R^1$ is hydrogen or $(C_1-C_6)$alkyl;

$R^2$ is hydrogen, $(C_1-C_6)$alkyl, $(C_3-C_9)$cycloalkyl or $(C_3-C_7)$cycloalkyl$(C_1-C_6)$alkyl;

$R^3$ is j is 0, 1 or 2;
k is 1 or 2;
p is 1, 2 or 3;
r is 1, 2 or 3;

$R^4$ is a subsituent independently selected from hydrogen, —OH, halogen, haloalkyl, $(C_1-C_6)$alkyl, $(C_3-C_7)$cycloalkyl, $(C_3-C_7)$cycloalkyl$(C_1-C_6)$alkyl, —CN, $(C_1-C_6)$alkylO—, $(C_3-C_7)$cycloalkylO—, $(C_1-C_6)$alkyl$(C_3-C_7)$cycloalkylO—, $(C_1-C_6)$alkylS—, $(C_3-C_7)$cycloalkylS—, $(C_1-C_6)$alkyl$(C_3-C_7)$cycloalkylS—, —$NR^9R^{10}$, —$NO_2$, —$CONR^9R^{10}$ and —$NR^2COR^{10}$;

$R^5$ is a substituent independently selected from hydrogen, halogen, —OH, haloalkyl, haloalkoxy, —CN, —$NO_2$, $(C_1-C_6)$alkyl, $(C_3-C_7)$cycloalkyl, $(C_3-C_7)$cycloalkyl$(C_1-C_6)$alkyl, $(C_1-C_6)$alkylO—, $(C_3-C_7)$cycloalkylO—, $(C_1-C_6)$alkyl$(C_3-C_7)$cycloalkylO—, —$CONH_2$ and —$CONR^9R^{10}$;

$R^6$ is $(C_1-C_6)$alkyl$SO_2$—, $(C_3-C_7)$cycloalkyl$SO_2$—, $(C_1-C_6)$alkyl$(C_3-C_7)$cycloalkyl$SO_2$—, $(C_1-C_6)$haloalkyl$SO_2$—, hydroxy$(C_2-C_6)$alkyl)$SO_2$—, (amino ($C_2$-$C_6$)alkyl)$SO_2$—, alkoxy($C_2$-$C_6$)alkyl)$SO_2$—, alkylamino($C_2$-$C_6$)alkyl)$SO_2$—, dialkylamino($C_2$-$C_6$)alkyl)$SO_2$—, aryl$SO_2$—, heteroaryl$SO_2$—, aryl($C_2$-$C_6$-alkyl$SO_2$—, $R^9R^{10}NSO_2$—, ($C_1$-$C_6$)alkylC(O)—, ($C_3$-$C_7$)cycloalkylC(O)—, ($C_3$-$C_7$)cycloalkyl($C_1$-$C_6$)alkylC(O)—, arylC(O)—, heteroarylC(O)—, $R^9R^{10}NC(O)$—, —(S)CN$R^9R^{10}$, aryl, heteroaryl, —($CH_2$)$_n$C(O)N$R^9R^{10}$, alkylS(NCN=)C—, $R^9R^{10}$N(NCN=)C—, ($C_1$-$C_6$)alkyl, ($C_3$-$C_7$)cycloalkyl, ($C_3$-$C_7$)cycloalkyl($C_1$-$C_6$)alkyl, aryl($C_1$-$C_6$)alkyl, heteroaryl($C_1$-$C_6$)alkyl, or $R^9$OC(O)—;

$R^7$ is hydrogen or alkyl;

$R^8$ is hydrogen, ($C_1$-$C_6$)alkyl, ($C_3$-$C_7$)cycloalkyl, ($C_3$-$C_7$)cycloalkyl($C_1$-$C_6$)alkyl, aryl, heteroaryl, ($C_1$-$C_6$)alkyl$SO_2$—, ($C_3$-$C_7$)cycloalkyl$SO_2$—, ($C_1$-$C_6$)alkyl($C_3$-$C_7$)cycloalkyl$SO_2$—, ($C_1$-$C_6$)haloalkyl$SO_2$— or aryl$SO_2$—;

$R^9$ is hydrogen, ($C_1$-$C_6$)alkyl, ($C_3$-$C_7$)cycloalkyl, ($C_3$-$C_7$)cycloalkyl($C_1$-$C_6$)alkyl, aryl($C_1$-$C_6$)alkyl, aryl, acyl or heteroaryl; and, $R^{10}$ is hydrogen, ($C_1$-$C_6$)alkyl, ($C_3$-$C_7$)cycloalkyl, ($C_3$-$C_7$)cycloalkyl($C_1$-$C_6$)alkyl, aryl($C_1$-$C_6$)alkyl, aryl or heteroaryl;

or $R^9$ and $R^{10}$ taken together with the nitrogen atom form a 4–7 membered ring containing 1 or 2 heteroatoms selected from N, O or S with proviso that two O or S atoms are not adjacent to one another;

n is 1 to 6;

or a pharmaceutically acceptable salt and/or hydrate thereof.

2. A compound of claim 1 wherein

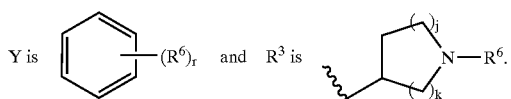

3. A compound of claim 2 wherein $R^5$ is a substituent independently selected from hydrogen, halogen, haloalkyl, alkoxy and haloalkoxy and the sum of j and k is 1, 2 or 3.

4. A compound of claim 2 wherein $R^6$ is ($C_1$-$C_6$)alkyl$SO_2$—, hydroxy($C_2$-$C_6$)alkyl$SO_2$—, ($C_3$-$C_7$)cycloalkyl$SO_2$—, $R^9R^{10}NSO_2$— or $NH_2SO_2$—.

5. A compound of claim 1 selected from

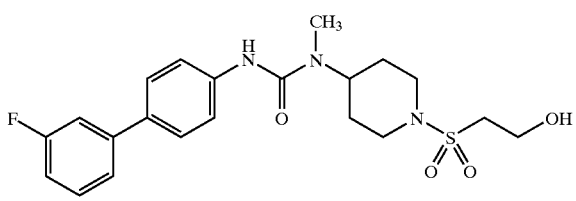

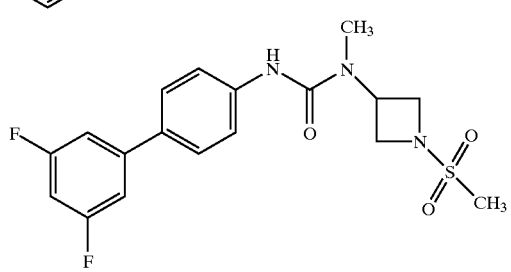

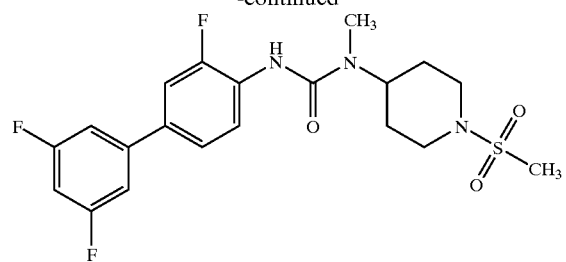

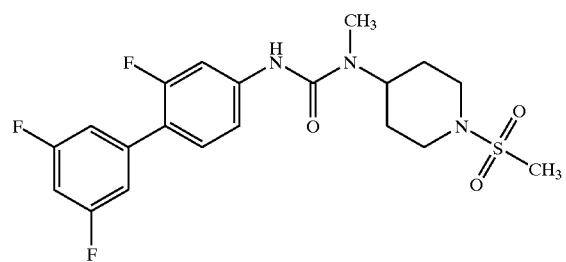

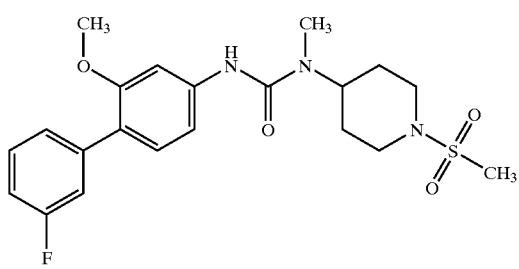

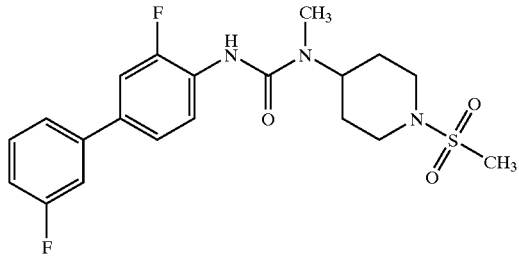

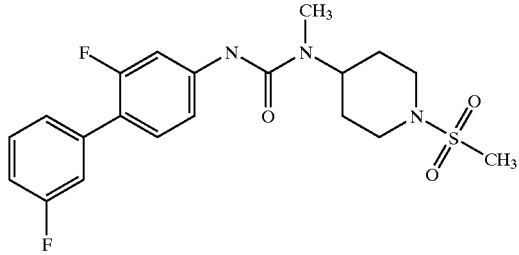

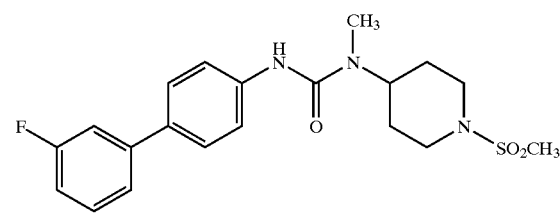

-continued
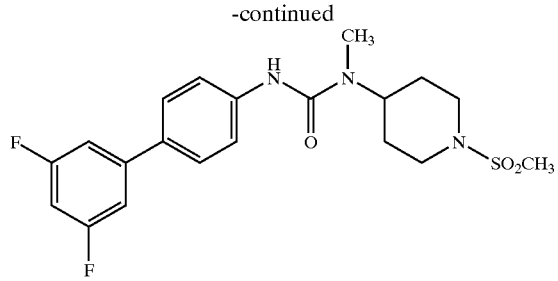
or a pharmaceutically acceptable salt and/or hydrate thereof.
6. A compound of claim 1, wherein the compound is
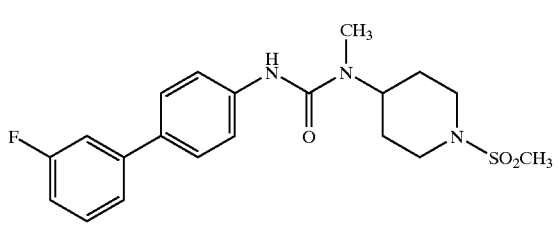
or a pharmaceutically acceptable salt and/or hydrate thereof.
7. A compound of claim 2 wherein $R^6$ is heteroarylC(O)—, $(C_1-C_6)$alkylC(O)— or $(C_3-C_7)$cycloalkyl C(O)—.
8. A compound of claim 1 selected from the group consisting of
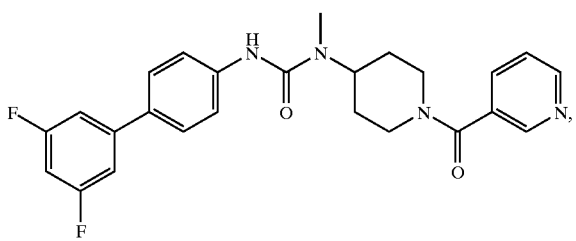
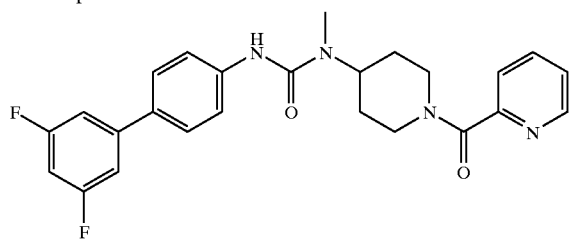
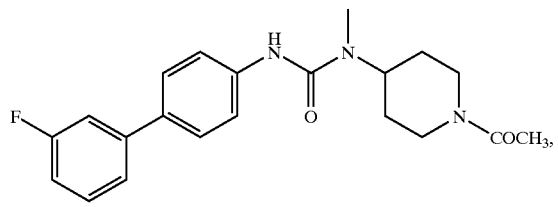
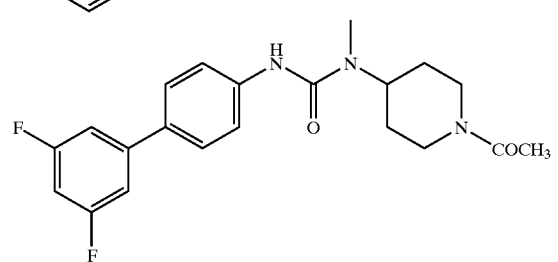
-continued
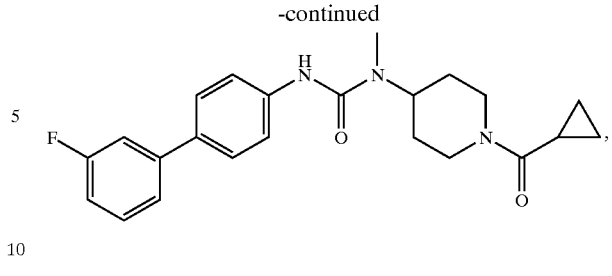
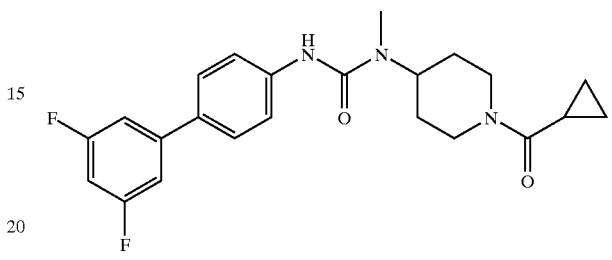
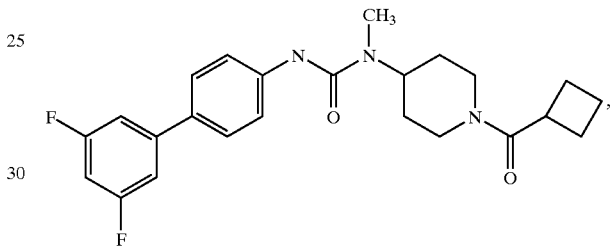
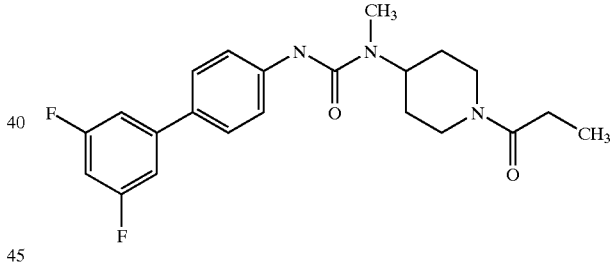
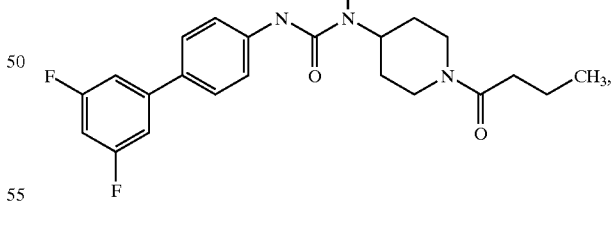
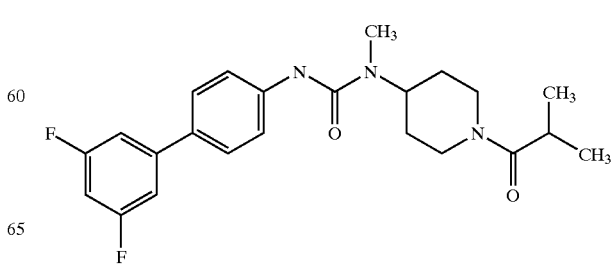

179

-continued

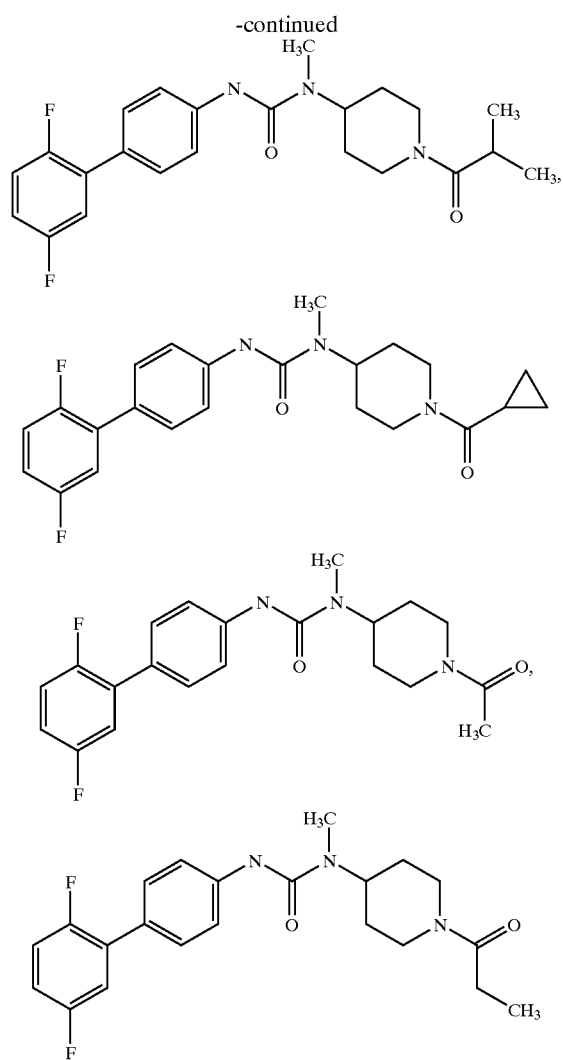

or a pharmaceutically acceptable salt and/or hydrate thereof.

9. A compound of claim 2 wherein $R^6$ is heteroaryl.

10. A compound of claim 1 selected from the group consisting of

180

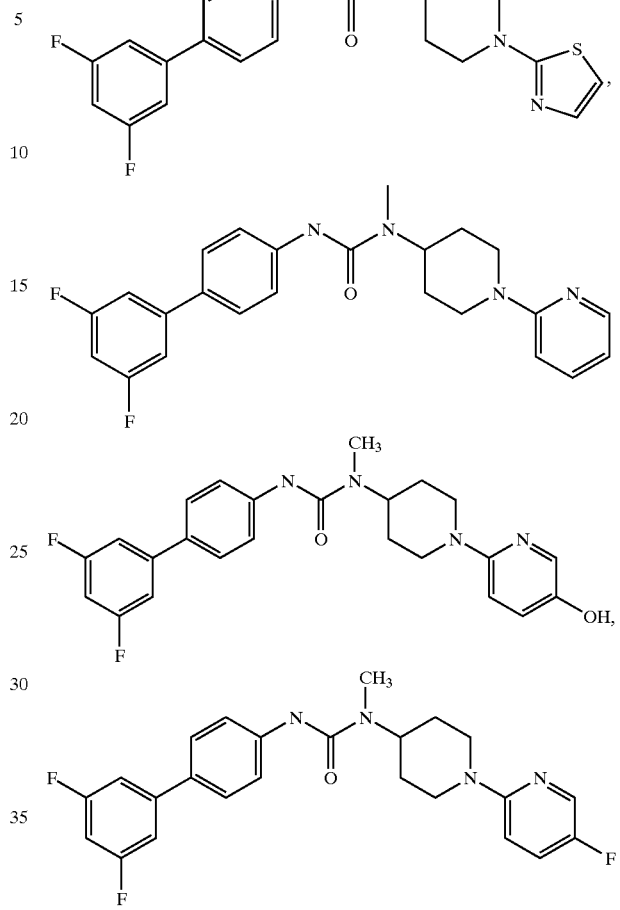

or a pharmaceutically acceptable salt and/or hydrate thereof.

11. A compound of claim 1 selected from the structural formulas set forth in the following table, and the pharmaceutically acceptable addition salts and/or hydrates thereof:

-continued

| Y | R¹ | R² | R³ | R⁴ |
|---|----|----|----|----|
| 2-F-C₆H₄- | —H | —CH₃ | 4-(iPrSO₂)-piperidin-1-yl | —H |
| 3-CF₃-C₆H₄- | —H | —CH₃ | 4-(MeSO₂)-piperidin-1-yl | —H |
| 2-CF₃-C₆H₄- | —H | —CH₃ | 4-(MeSO₂)-piperidin-1-yl | —H |
| 2-CF₃-C₆H₄- | —H | —CH₃ | 4-(iPrSO₂)-piperidin-1-yl | —H |
| 2-CF₃-C₆H₄- | —H | —CH₃ | 4-(CF₃SO₂)-piperidin-1-yl | —H |
| 4-F₃CO-C₆H₄- | —H | —CH₃ | 4-(MeSO₂)-piperidin-1-yl | —H |
| 3-F-C₆H₄- | —H | —CH₃ | 4-(CF₃SO₂)-piperidin-1-yl | —H |
| 4-CF₃-C₆H₄- | —H | —CH₃ | 4-(MeSO₂)-piperidin-1-yl | —H |
| 4-F₃CO-C₆H₄- | —H | —CH₃ | 1-(cyclopropylmethyl)-piperidin-4-yl | —H |

-continued

| Y | R¹ | R² | R³ | R⁴ |
|---|----|----|----|----|
| phenyl | —H | —CH₃ | 1-(cyclopropylmethyl)piperidin-4-yl | —H |
| 2-fluorophenyl | —H | —CH₃ | 1-(cyclopropylmethyl)piperidin-4-yl | —H |
| 3-(trifluoromethyl)phenyl | —H | —CH₃ | 1-(cyclopropylmethyl)piperidin-4-yl | —H |
| 3,5-difluorophenyl | —H | —CH₃ | 1-(cyclopropylmethyl)piperidin-4-yl | —H |
| 3-fluorophenyl | —H | —CH₃ | 1-(cyclopropylmethyl)piperidin-4-yl | —H |
| 3,5-difluorophenyl | —H | —CH₃ | 1-(pyridin-3-yl)piperidin-4-yl | —H |
| 3-fluorophenyl | —H | —CH₃ | 1-(pyridin-2-yl)piperidin-4-yl | —H |
| 3-(trifluoromethyl)phenyl | —H | —CH₃ | 1-(pyridin-2-yl)piperidin-4-yl | —H |

| Y | R¹ | R² | R³ | R⁴ |
|---|---|---|---|---|
| 3-Cl,4-F-phenyl | —H | —CH₃ | 4-(pyridin-2-yl)piperidin-4-yl | —H |
| 4-F-phenyl | —H | —CH₃ | 4-(pyridin-2-yl)piperidin-4-yl | —H |
| 3,5-diCl-phenyl | —H | —CH₃ | 4-(pyridin-2-yl)piperidin-4-yl | —H |
| 3-F-phenyl | —H | —CH₃ | 4-(pyridin-3-yl)piperidin-4-yl | —H |
| 3-Cl-phenyl | —H | —CH₃ | 4-(pyridin-3-yl)piperidin-4-yl | —H |
| 3-F-phenyl | —H | —CH₃ | 4-(thiazol-2-yl)piperidin-4-yl | —H |
| 3-F-phenyl | —H | —CH₃ | 4-(pyrimidin-2-yl)piperidin-4-yl | —H |

-continued

| Y | R¹ | R² | R³ | R⁴ |
|---|----|----|----|----|
| 3,5-difluorophenyl | —H | —CH₃ | 4-(pyrimidin-2-yl)piperidin-4-yl | —H |
| 3-fluorophenyl | —H | —CH₃ | 4-(pyridin-2-yl)piperidin-4-yl | 2-F |
| phenyl | —H | —CH₃ | 1-(pyridin-3-ylcarbonyl)piperidin-4-yl | —H |
| phenyl | —H | —CH₃ | 1-acetyl-4-methylpiperidin-4-yl | —H |
| phenyl | —H | —CH₃ | 1-(cyclopropylcarbonyl)-4-methylpiperidin-4-yl | —H |
| phenyl | —H | —CH₃ | 1-(cyclohexylcarbonyl)-4-methylpiperidin-4-yl | —H |
| phenyl | —H | —CH₃ | 1-benzoyl-4-methylpiperidin-4-yl | —H |
| phenyl | —H | —CH₃ | 1-(pyridin-2-ylcarbonyl)-4-methylpiperidin-4-yl | —H |
| phenyl | —H | —CH₃ | 1-(pyridin-4-ylcarbonyl)-4-methylpiperidin-4-yl | —H |

-continued

| Y | R¹ | R² | R³ | R⁴ |
|---|----|----|----|----|
| 3-F-phenyl | —H | —CH₃ | 4-(1-benzoyl)piperidinyl | —H |
| 3-F-phenyl | —H | —CH₃ | 4-[1-(pyridine-2-carbonyl)]piperidinyl | —H |
| 3-F-phenyl | —H | —CH₃ | 4-[1-(pyridine-3-carbonyl)]piperidinyl | —H |
| 3-F-phenyl | —H | —CH₃ | 4-[1-(pyridine-4-carbonyl)]piperidinyl | —H |
| 3-F-phenyl | —H | —CH₃ | 4-[1-(2-chloropyridine-4-carbonyl)]piperidinyl | —H |
| 3-F-phenyl | —H | —CH₃ | 4-[1-(2,6-dichloropyridine-4-carbonyl)]piperidinyl | —H |
| 3-F-phenyl | —H | —CH₃ | 4-[1-(2-chloro-6-methylpyridine-4-carbonyl)]piperidinyl | —H |

-continued

| Y | R¹ | R² | R³ | R⁴ |
|---|---|---|---|---|
| 3-F-phenyl | —H | —CH₃ | 4-piperidinyl-N-C(O)-(2-OCH₃, 6-Cl-pyridin-4-yl) | —H |
| 3,5-diF-phenyl | —H | —CH₃ | 4-piperidinyl-N-C(O)-phenyl | —H |
| 3,5-diF-phenyl | —H | —CH₃ | 4-piperidinyl-N-C(O)-(pyridin-4-yl) | —H |
| phenyl | —H | —CH₃ | 4-piperidinyl-N-C(O)-(pyridin-3-yl N-oxide) | —H |
| 3-F-phenyl | —H | —CH₃ | 4-piperidinyl-N-SO₂NH₂ | —H |
| phenyl | —H | —CH₃ | 4-piperidinyl-N-SO₂NH₂ | —H |
| 3-F-phenyl | —H | —CH₃ | 4-piperidinyl-N-SO₂NH₂ | —H |
| phenyl | —H | —CH₃ | 4-piperidinyl-N-SO₂NH₂ | —H |

-continued

| Y | R$^1$ | R$^2$ | R$^3$ | R$^4$ |
|---|---|---|---|---|
| 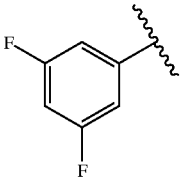 | —H | —CH$_3$ | 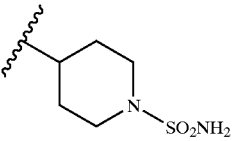 | —H. |

12. A pharmaceutical composition comprising a compound of formula I as defined in claim 1 and a pharmaceutically acceptable carrier.

13. A method of treating metabolic or eating disorders comprising administering to a mammal in need of such treatment a therapeutically effective amount of a compound of claim 1 of said compound.

14. The method of claim 13 wherein said metabolic disorder is obesity.

15. The method of claim 13 wherein said eating disorder is hyperphagia.

16. A method of treating disorders associated with obesity comprising administering to a mammal in need of such treatment a therapeutically effective amount of a compound of claim 1 or a pharmaceutically acceptable salt of said compound.

17. The method of claim 16 wherein said disorders associated with obesity are Type II Diabetes, insulin resistance, hyperlipidemia and hypertension.

\* \* \* \* \*